(12) United States Patent
Kim et al.

(10) Patent No.: US 11,603,346 B2
(45) Date of Patent: Mar. 14, 2023

(54) POLYETHYLENE GLYCOL DERIVATIVE AND USE THEREOF

(71) Applicant: HANMI PHARM. CO., LTD., Hwaseong-si (KR)

(72) Inventors: Dae Jin Kim, Hwaseong-si (KR); Jong Soo Lee, Hwaseong-si (KR); Sung Min Bae, Hwaseong-si (KR); Se Chang Kwon, Hwaseong-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 0 days.

(21) Appl. No.: 16/082,737

(22) PCT Filed: Mar. 7, 2017

(86) PCT No.: PCT/KR2017/002469
§ 371 (c)(1),
(2) Date: Sep. 6, 2018

(87) PCT Pub. No.: WO2017/155288
PCT Pub. Date: Sep. 14, 2017

(65) Prior Publication Data
US 2019/0071379 A1 Mar. 7, 2019

(30) Foreign Application Priority Data
Mar. 7, 2016 (KR) .................. 10-2016-0027317

(51) Int. Cl.
| | | |
|---|---|---|
| C07C 47/198 | (2006.01) | |
| A61K 39/395 | (2006.01) | |
| C07C 323/22 | (2006.01) | |
| C07C 323/39 | (2006.01) | |
| C07C 233/05 | (2006.01) | |
| A61K 47/50 | (2017.01) | |
| C07C 237/04 | (2006.01) | |
| A61K 38/18 | (2006.01) | |
| A61K 47/60 | (2017.01) | |
| C07C 233/18 | (2006.01) | |
| C07C 323/12 | (2006.01) | |
| C07D 213/71 | (2006.01) | |

(52) U.S. Cl.
CPC ............ *C07C 47/198* (2013.01); *A61K 38/18* (2013.01); *A61K 39/395* (2013.01); *A61K 47/50* (2017.08); *A61K 47/60* (2017.08); *C07C 233/05* (2013.01); *C07C 233/18* (2013.01); *C07C 237/04* (2013.01); *C07C 323/12* (2013.01); *C07C 323/22* (2013.01); *C07C 323/39* (2013.01); *C07D 213/71* (2013.01)

(58) Field of Classification Search
CPC .................................................. C07C 47/198
See application file for complete search history.

(56) References Cited

U.S. PATENT DOCUMENTS

2015/0182593 A1 7/2015 Jung et al.

FOREIGN PATENT DOCUMENTS

| CN | 102892420 A | 1/2013 | |
|---|---|---|---|
| KR | 10-2005-0025974 A | 3/2005 | |
| KR | 10-2011-0047169 A | 5/2011 | |
| KR | 10-2013-0040889 A | 4/2013 | |
| KR | 10-2014-0018462 A | 2/2014 | |
| WO | 96/032478 A1 | 10/1996 | |
| WO | 97/034631 A1 | 9/1997 | |
| WO | 01/002017 A2 | 1/2001 | |
| WO | WO-2002087497 A2 * | 11/2002 | |
| WO | 2009/134976 A1 | 11/2009 | |
| WO | 2010/021720 A1 | 2/2010 | |
| WO | 2010/138343 A1 | 12/2010 | |
| WO | WO-2011126974 A1 * | 10/2011 | ........... A61K 31/713 |
| WO | 2015/173824 A1 | 11/2015 | |
| WO | 2015/183054 A1 | 12/2015 | |

OTHER PUBLICATIONS

Chemical Abstract Services 2002:849372 Document No. 137:358119 2002, 2 pages.*
Allen "A new strategy for attachment of antibodies to sterically stabilized liposomes resulting in efficient targeting to cancer cells" Biochimica et Biophysica Acta 1237 (1995) 99-108.*
PEG (Succinimidyl Carboxymethyl Ester)2 Online "https://www.jenkemusa.com/product/peg-di-succinimidyl-carboxymethyl-ester" accessed Jan. 4, 2020.*
Vanderhooft Biomacromolecules (2007), 8(9), 2883-2889.*
Brinkley "A Brief Survey of Methods for Preparing Protein Conjugates with Dyes, Haptens, and Cross-Linking Reagents." Bioconjugate Chemistry 1992, 3, 2-13.*
Andre' M. Cantin, et al., "Polyethylene Glycol Conjugation at $Cys^{232}$ Prolongs the Half-Life of α1 Proteinase Inhibitor", American Journal of Respiratory Cell and Molecular Biology, 2002, pp. 659-665, vol. 27.
International Search Report for PCT/KR2017/002469 dated Jul. 13, 2017 [PCT/ISA/210].
Oba et al., "Cyclic RGD Peptide-Conjugated Polyplex Micelles as a Targetable Gene Delivery System Directed to Cells Possessing $α_vβ_3$ and $α_vβ_5$ Integrins", Bioconjugate Chem., 2007, vol. 18, pp. 1415-1423 (9 pages total).
STN on the Web Registry, Registry, Chemical Abstract RN, RN: 1294505-04-6, May 13, 2011 (1 page total).
Chattopadhyay et al., "Design and Characterization of HER-2-Targeted Gold Nanoparticles for Enhanced X-radiation Treatment of Locally Advanced Breast Cancer", Molecular Pharmaceutics, 2010, vol. 7, No. 6, pp. 2194-2206.
Noel et al., "Development of a Polyester Coating Combining Antithrombogenic and Cell Adhesive Properties: Influence of Sequence and Surface Density of Adhesion Peptides", Biomacromolecules, 2015, vol. 16, pp. 1682-1694.
Wang et al., "Synthesis of new dimeric-PEG-supported cinchona ammonium salts as chiral phase transfer catalysts for the alkylation of Schiff bases with water as the solvent", Asymmetry, 2007, vol. 18, pp. 108-114.

(Continued)

*Primary Examiner* — David K O'Dell
(74) *Attorney, Agent, or Firm* — Sughrue Mion, PLLC

(57) ABSTRACT

The present invention relates to polyethylene glycol derivatives and use thereof.

17 Claims, 22 Drawing Sheets

Specification includes a Sequence Listing.

(56) References Cited

OTHER PUBLICATIONS

Ohkawa H et al: "Synthesis of Multiacyl Poly(Ethylene Glycol) for the Conjugation of Cytochrome C To Phospholipid Vesicle", Bioconjugate Chemistry, American Chemical Society, US, vol. 11, No. 6, Nov. 1, 2000, pp. 815-821, XP001015727.

Fan Chen et al., "Understanding chemical reactivity for homo- and heterobifunctional protein cross-linking agents", Journal of Mass Spectrometry, vol. 48, Issue 7, Jun. 18, 2013, 1 page, Abstract only.

* cited by examiner

[FIG. 1a]
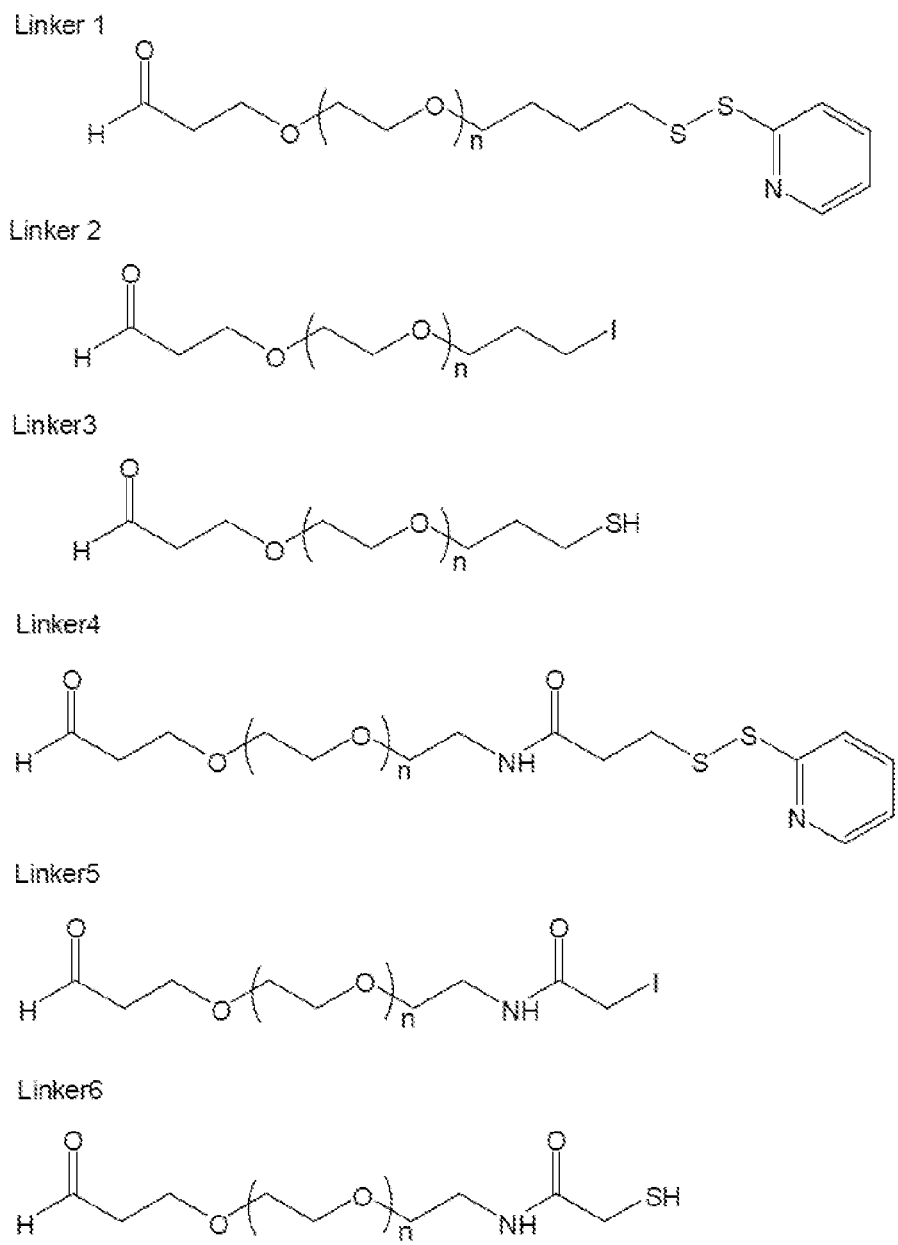

[FIG. 1b]
Linker7
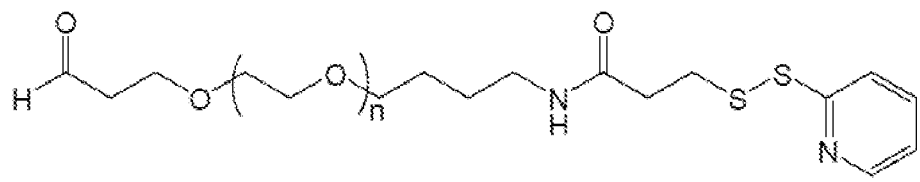
Linker8
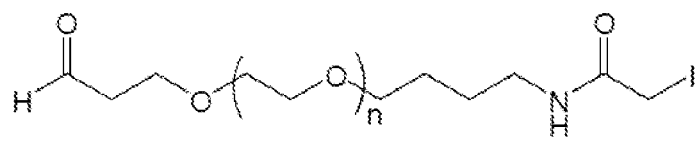
Linker9
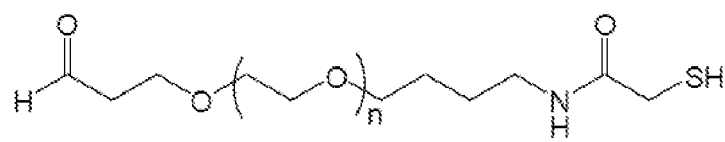
Linker 10
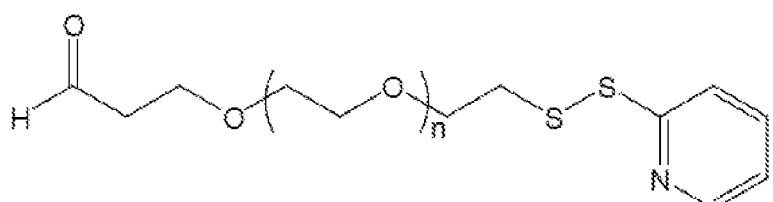
Linker 11
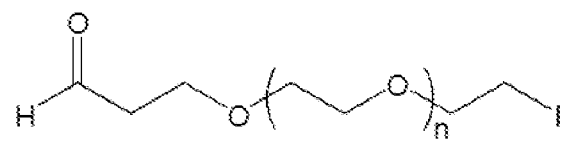
Linker 12
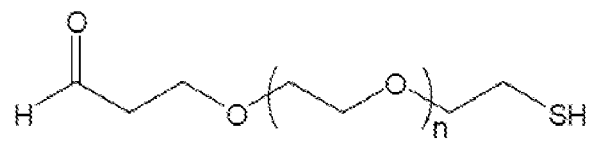

[FIG. 18]
Test of Reactivity Comparison of Thiol reactive group
| Linker No. | Thiol reactive group | Structure Presence of Amide (-CONH-) | Purity (RPC) | Reactivity (PEGylation @ General Condition *) |
|---|---|---|---|---|
| 3 | SH | x | 75.9% | 2.3% |
| 9 | SH | o | 75.9% | 14.5% |
| 11 | I | x | 88.7% | NA |
| 2 | I | x | 86.6% | NA |
| 2 | IA | o | 88.0% | 12.3% |
| 8 | IA | o | 78.2% | 39.2% |
*3mg/ml, 50mM HEPES (pH 7.5), 60% IPA, 2 hrs @ RT & Dark
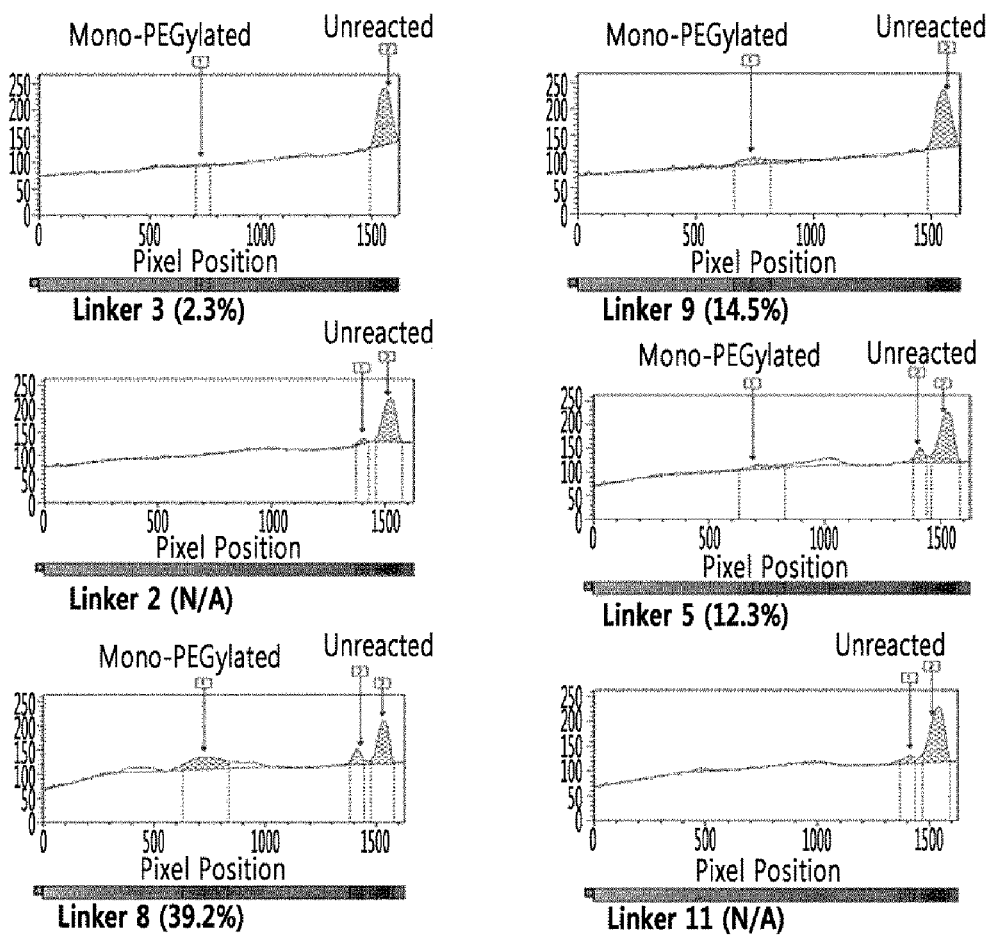

[FIG. 19]
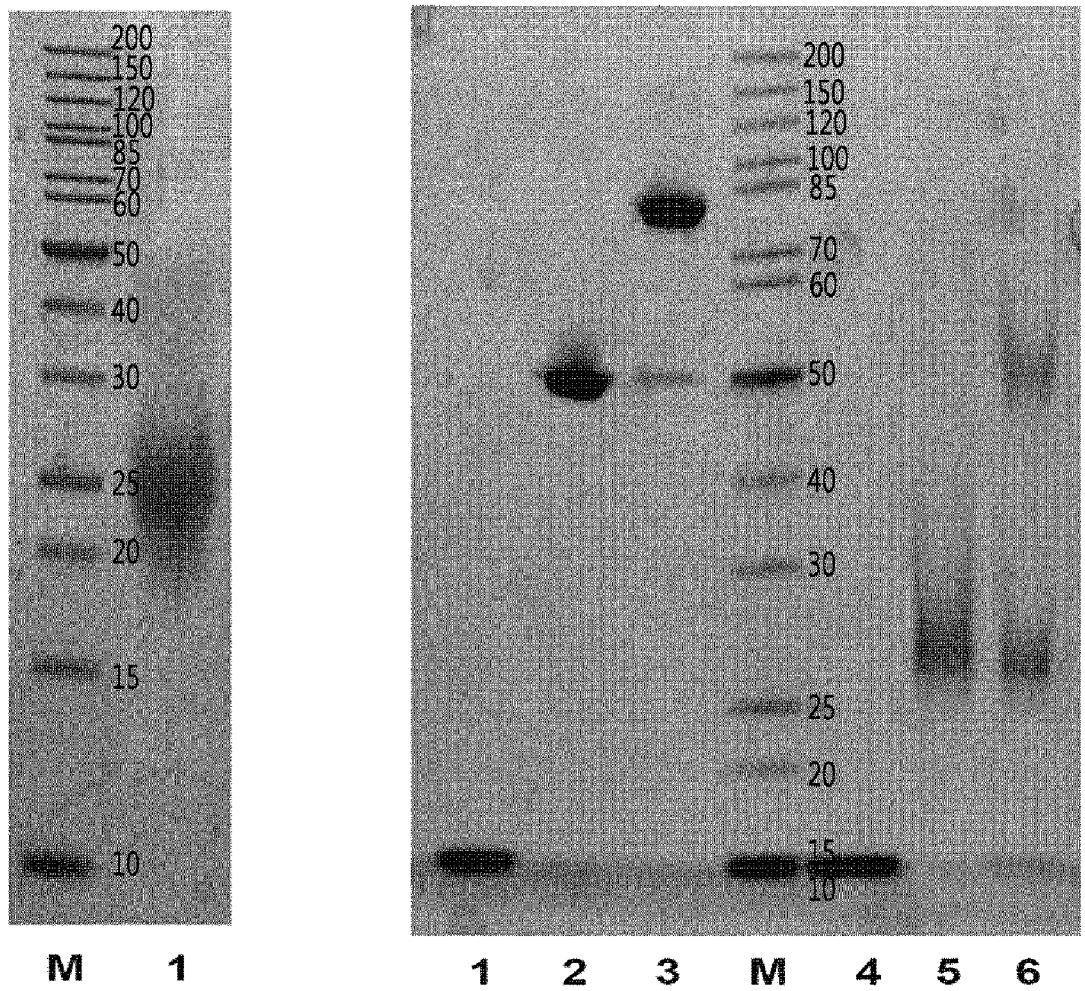

[FIG. 20]

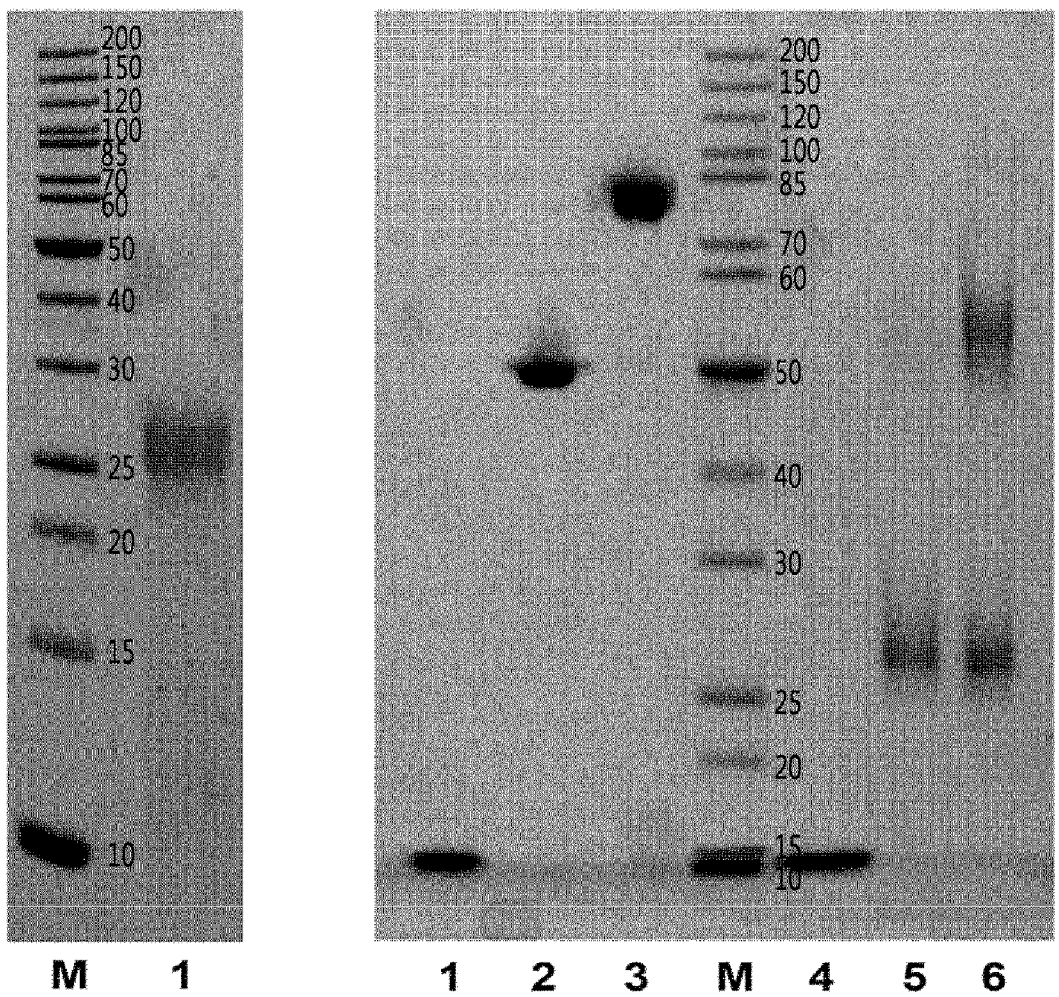

M: Marker
1: A conjugate where a linker #8 is linked to a triple agonist peptide (non-reducing)

1: Triple agonist peptides (non-reducing)
2: Immunoglobulin Fc (non-reducing)
3: A conjugate where a triple agonist peptide is linked with Immunoglobulin Fc by a linker #8 (non-reducing)
M: Marker
4: Triple agonist peptides (reducing)
5: Immunoglobulin Fc (reducing)
6: A conjugate where a triple agonist peptide is linked with Immunoglobulin Fc by a linker #8 (reducing)

[FIG. 21]
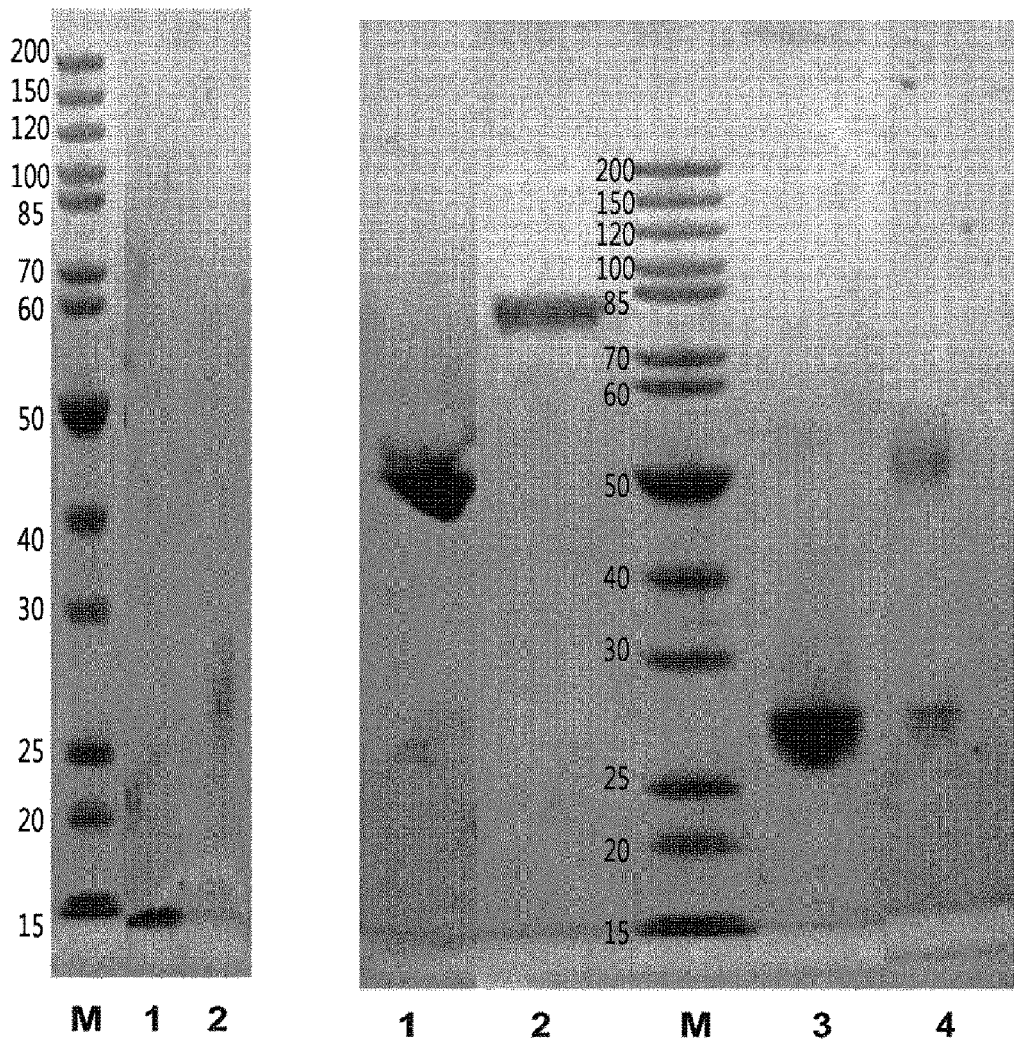

POLYETHYLENE GLYCOL DERIVATIVE AND USE THEREOF

CROSS REFERENCE TO RELATED APPLICATIONS

This application is a National Stage of International Application No. PCT/KR2017/002469 filed Mar. 7, 2017, claiming priority based on Korean Patent Application No. 10-2016-0027317 filed Mar. 7, 2016.

TECHNICAL FIELD

The present invention relates to polyethylene glycol derivatives and uses thereof.

BACKGROUND ART

Polyethylene glycol (PEG) is a material which has a high in vivo half-life but does not have antigenicity. PEG is a representative biocompatible material which is widely used pharmaceutically when bound to various physiologically active materials such as lipids, proteins, etc., and studies on the pharmaceutical use of PEG itself are underway.

In particular, PEG is widely used from the aspect of protein therapeutics because PEG can bind to protein therapeutics and thereby increase their blood half-life while reducing their antigenicity. Additionally, it was reported that PEGylation, which refers to the covalent linking of PEG molecules to proteins, can improve the stability of protein therapeutics (Cantin et al., *Am. J.* 27: 659-665 (2002)).

Meanwhile, during the manufacturing process, improving the manufacturing yield of these medicaments while maintaining the activities of the medicament requires sophisticated manufacturing technology. Accordingly, continuous studies have been made to develop methods for manufacturing protein therapeutics including PEG and the PEG used therein.

In preparing a physiologically active polypeptide conjugate using PEG, the present inventors used PEG having at least two reactive groups as a linker (Korean Patent Application Publication No. 10-2014-0018462).

The conventional PEG compounds are known to have, as reactive groups, aldehyde, succinimidyl, maleimide, vinylsulfone, halogenated acetamide, or ortho-pyridyl disulfide (OPSS), etc.

However, the conventionally-used PEG compounds have an inconvenience in that although they have a reactive group at their ends, their reactivity varies due to the structures of the PEG compounds.

Accordingly, there has been a need for the development of a novel polyethylene glycol derivative which not only includes reactive groups capable of binding to target materials but also more easily reacts with these materials.

DISCLOSURE

Technical Problem

An object of the present invention is to provide a polyethylene glycol, a stereoisomer thereof, or a pharmaceutically acceptable salt thereof.

Another object of the present invention is to provide a method for preparing a physiologically active polypeptide to which a polyethylene glycol compound is attached, including reacting the polyethylene glycol compound with a physiologically active polypeptide.

Still another object of the present invention is to provide a method for preparing a conjugate in which a physiologically active polypeptide and a carrier protein are linked by a polyethylene glycol compound.

Still another object of the present invention is to provide a physiologically active polypeptide to which the polyethylene glycol compound is attached.

Still another object of the present invention is to provide a conjugate in which each of a physiologically active polypeptide and a carrier protein is independently attached to reactive groups at both ends of the polyethylene glycol compound.

Still another object of the present invention is to provide a method for preparing the polyethylene glycol compound.

Still another object of the present invention is to provide a use of the polyethylene glycol compound for linking a carrier, which is capable of increasing an in vivo half-life of a physiologically active polypeptide, to a physiologically active polypeptide.

Still another object of the present invention is to provide a composition containing the physiologically active polypeptide to which the polyethylene glycol compound is attached or the conjugate.

Still another object of the present invention is to provide a polyethylene glycol compound linker for linking a carrier, which is capable of increasing an in vivo half-life of a physiologically active polypeptide, to a physiologically active polypeptide.

Technical Solution

An aspect of the present invention provides a polyethylene glycol compound, a stereoisomer thereof, or a pharmaceutically acceptable salt thereof.

In a specific embodiment, the compound is a compound represented by Formula 1 below:

[Formula 1]

$$R_1 {-} L_1 {-} O {-}(CH_2CH_2O)_n {-} L_2 {-} \overset{H}{\underset{\parallel}{N}} {-} \underset{O}{C} {-} L_3 {-} R_2$$

wherein, in Formula 1 above, $R_1$ is selected from the group consisting of 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In another specific embodiment, $R_2$ is ortho-pyridyl disulfide, thiol, or iodine.

In still another specific embodiment, $R_1$ is aldehyde.

In still another specific embodiment, $R_1$ and $R_2$ have mutually different functional groups.

In still another specific embodiment, the compound is represented by Formula 2 below:

CHO—$(CH_2)_j$—O—$(CH_2CH_2O)_n$—H$(CH_2)_m$—NH(CO)—$(CH_2)_k$—$R_2$    [Formula 2]

wherein, in Formula 2 above;

n is an integer of 10 to 2400;

each of j, m, and k is independently an integer of 1 to 6; and $R_2$ is ortho-pyridyl disulfide (OPSS), thiol, or halogen.

In still another specific embodiment, the compound is selected from the group consisting of Formulas 3 to 11:

[Formula 3]

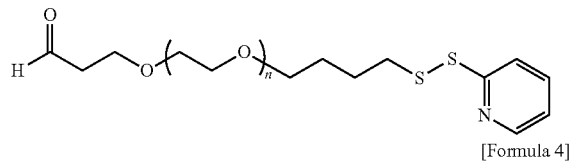

[Formula 4]

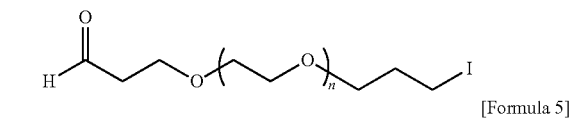

[Formula 5]

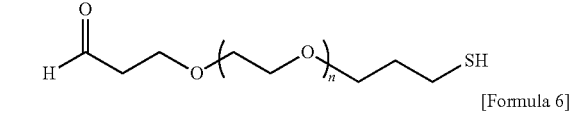

[Formula 6]

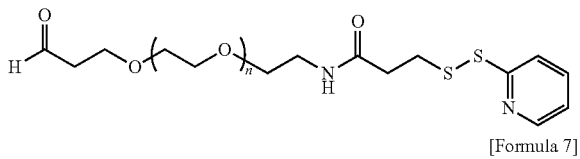

[Formula 7]

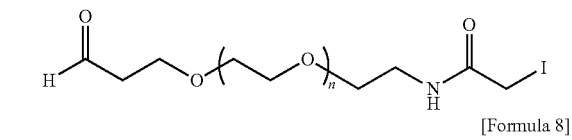

[Formula 8]

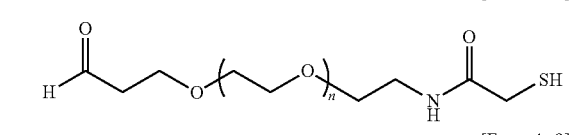

[Formula 9]

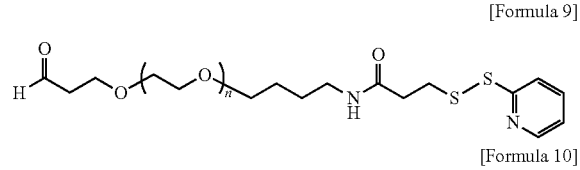

[Formula 10]

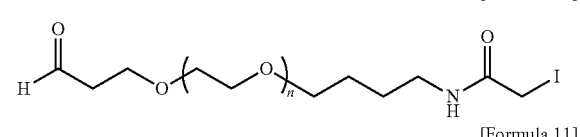

[Formula 11]

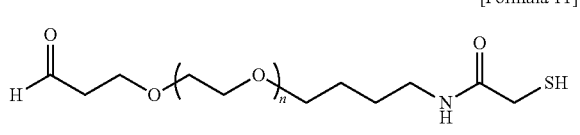

In Formulas 3 to 11, n is an integer of 10 to 2400.

Another aspect of the present invention provides a method for preparing a physiologically active polypeptide to which a polyethylene glycol compound is attached, which includes reacting a polyethylene glycol compound with a physiologically active polypeptide to prepare a physiologically active polypeptide to which a polyethylene glycol compound is attached.

In a specific embodiment of the method, ortho-pyridyl disulfide (OPSS), thiol, or halogen located at $R_2$ reacts with a thiol group located at the cysteine residue of the physiologically active polypeptide.

In another specific embodiment, the method further includes purifying the physiologically active polypeptide to which a polyethylene glycol compound is attached.

In still another specific embodiment, the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

In still another specific embodiment, the physiologically active polypeptide is selected from the group consisting of glucagon; insulin; somatostatin; peptide YY (PYY); neuropeptide Y (NPY); glucagon-like peptides including glucagon-like peptide-1 (GLP-1) and glucagon-like peptide-2 (GLP-2); exendin-3; exendin-4; oxyntomodulin; peptides having an activity on glucagon receptors, GLP-1 receptors, and GIP receptors; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); growth hormone-releasing peptides; granulocyte-colony-stimulating factors (GCSF); interferons (IFNs); interleukins; prolactin-releasing peptides; orexin; thyroid-releasing peptides; cholecystokinin; gastrin inhibitory peptides; calmodulin; gastric-releasing peptides; motilin; vasoactive intestinal peptides; atrial natriuretic peptides (ANPs); B-type natriuretic peptides (BNPs); C-type natriuretic peptides (CNPs); neurokinin A; neuromedin; renin; endothelin; sarafotoxin peptide; carsomorphin peptide; dermorphin; dynorphin; endorphin; enkepalin; T cell factors; tumor necrosis factor; tumor necrosis factor receptors; urokinase receptors; tumor inhibitory factors; collagenase inhibitors; thymopoietin; thymulin; thymopentin; thymosin; thymic humoral factor; adrenomedullin; allatostatin; amyloid β-protein fragments; antibacterial peptides; antioxidant peptides; bombesin; osteocalcin; CART peptides; E-selectin; ICAM-1; VCAM-1; leucokine; kringle-5; laminin; inhibin; galanin; fibronectin; pancreastatin; fuzeon; interferon receptors; G protein-coupled receptors; interleukin receptors; enzymes; interleukin-binding proteins; cytokine-binding proteins; macrophage-activating factors; macrophage peptides; B cell factor; protein A; inhibitors; cell necrosis glycoprotein; immunotoxin; lymphotoxin; tumor inhibitory factors; metastasis growth factors; α-1-antitrypsin; albumin; α-lactalbumin; apolipoprotein-E; erythropoietin; highly glycosylated erythropoietin; angiopoietins; hemoglobin; thrombin; thrombin receptor-activating peptides; thrombomodulin; blood factors VII, VIIa, VIII, IX, and XIII; plasminogen-activating factors; fibrin-binding peptides; urokinase; streptokinase; hirudin; protein C; C-reactive protein; renin inhibitors; superoxide dismutase; platelet-derived growth factors; epidermal growth factors; epithelial cell growth factors; angiostatin; angiotensin; osteogenic growth factors; osteogenesis-promoting proteins; atriopeptin; cartilage-inducing factors; elcatonin; connective tissue-activating factors; tissue factor pathway inhibitors; luteinizing hormone-releasing hormone; nerve growth factors; relaxin; somatomedin; insulin-like growth factor; adrenocortical hormone; pancreatic polypeptides; gastrin-releasing peptides; corticotropin-releasing factor; thyroid-stimulating hormone; autotoxin; lactoferrin; myostatin; cell surface antigens; virus-derived vaccine antigens; monoclonal antibody; polyclonal antibody; antibody fragments; erythropoietic growth factors; leukopoietin; amylin; and analogs thereof.

Still another aspect of the present invention provides a method for preparing a conjugate, in which a physiologically active polypeptide and a carrier protein are linked by a polyethylene glycol compound.

In a specific embodiment, the method includes:

(a) reacting the polyethylene glycol compound with any one of a physiologically active polypeptide or carrier protein, thereby preparing a polyethylene glycol compound, wherein the physiologically active polypeptide or carrier protein is attached to one end of the polyethylene glycol compound and the other end of the polyethylene glycol compound has a reactive end group; and (b) reacting the polyethylene glycol compound prepared in step (a) above, wherein the physiologically active polypeptide or carrier protein is attached to one end of the polyethylene glycol compound and the other end of the polyethylene glycol compound has a reactive end group, with the other one between the physiologically active polypeptide or carrier protein, so as to link the carrier protein or physiologically active polypeptide to the reactive end group of the polyethylene glycol compound, thereby preparing a conjugate in which the physiologically active polypeptide and the carrier protein are linked by a polyethylene glycol compound.

In another specific embodiment, the method includes:

(a) reacting the polyethylene glycol compound with a physiologically active polypeptide, thereby preparing a polyethylene glycol compound, wherein the physiologically active polypeptide is attached to one end of the polyethylene glycol compound and the other end of the polyethylene glycol compound has a reactive end group; and (b) reacting the polyethylene glycol compound prepared in step (a) above, wherein the physiologically active polypeptide is attached to one end of the polyethylene glycol compound and the other end of the polyethylene glycol compound has a reactive end group, with a carrier protein, so as to link the carrier protein to the reactive end group of the polyethylene glycol compound.

In still another specific embodiment, the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

In still another specific embodiment, the polyethylene glycol compound in step (a) has the structure of Formula 1 above.

In still another specific embodiment, step (a) of the method is characterized in that $R_2$ of the polyethylene glycol compound having the structure of Formula 1 above is reacted with a thiol group located at the cysteine residue of the physiologically active polypeptide.

In still another specific embodiment, step (b) of the method is characterized in that an aldehyde end group of the polyethylene glycol compound is reacted with an amine group of an immunoglobulin Fc fragment.

In still another specific embodiment, the method further includes purifying the conjugate, wherein the physiologically active polypeptide and the carrier protein are linked by a polyethylene glycol compound.

In still another specific embodiment, the carrier protein is albumin and a fragment thereof, a polymer of a repeating unit of a particular amino acid sequence, antibody, an antibody fragment, an FcRn-binding material, fibronectin, transferrin, saccharide, or elastin.

In still another specific embodiment, the FcRn-binding material is an immunoglobulin Fc fragment.

Still another aspect of the present invention provides a physiologically active polypeptide to which the polyethylene glycol compound is attached.

In a specific embodiment, the physiologically active polypeptide, to which the above compound is attached, includes the structure represented by any one of Formulas 15 to 17 below:

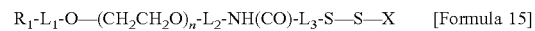

$R_1$-$L_1$-O—$(CH_2CH_2O)_n$-$L_2$-NH(CO)-$L_3$-S—S—X    [Formula 15]

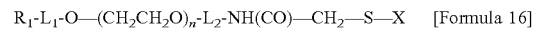

$R_1$-$L_1$-O—$(CH_2CH_2O)_n$-$L_2$-NH(CO)—$CH_2$—S—X    [Formula 16]

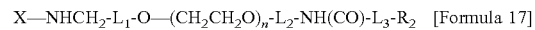

X—NHCH$_2$-$L_1$-O—$(CH_2CH_2O)_n$-$L_2$-NH(CO)-$L_3$-$R_2$    [Formula 17]

In Formulas 15 to 17 above, $R_1$ is selected from 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched $C_{1-6}$ alkylene;

n is an integer of 10 to 2400;

$R_2$ is ortho-pyridyl disulfide (OPSS), thiol, or halogen; and

X is a physiologically active polypeptide moiety.

Still another aspect of the present invention provides a conjugate, wherein each of a physiologically active polypeptide and a carrier protein is independently attached to reactive groups at both ends of the polyethylene glycol compound.

In a specific embodiment, the conjugate is a conjugate having the structure represented by Formula 18 or 19 below:

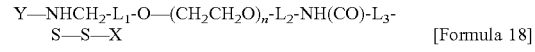

Y—NHCH$_2$-$L_1$-O—$(CH_2CH_2O)_n$-$L_2$-NH(CO)-$L_3$-
S—S—X    [Formula 18]

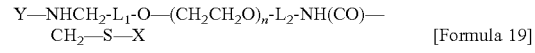

Y—NHCH$_2$-$L_1$-O—$(CH_2CH_2O)_n$-$L_2$-NH(CO)—
CH$_2$—S—X    [Formula 19]

In Formulas 18 and 19 above, each of $L_1$ to $L_3$ is independently a linear or branched $C_{1-6}$ alkylene, n is an integer of 10 to 2400, X is a physiologically active polypeptide moiety; and Y is a carrier protein moiety.

In another specific embodiment, the carrier protein is albumin and a fragment thereof, a polymer of a repeating unit of a particular amino acid sequence, antibody, an antibody fragment, an FcRn-binding material, fibronectin, transferrin, saccharide, or elastin.

In still another specific embodiment, the FcRn-binding material is an immunoglobulin Fc fragment.

Still another aspect of the present invention provides a method for preparing the polyethylene glycol compound.

In a specific embodiment, the method includes:

(a) introducing $R_1$ selected from the group consisting of 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof, to one end of a polyethylene glycol; and (b) introducing the structure of —NH(CO)L$_3$-R$_2$ to the other end of the polyethylene glycol, wherein R$_2$ is orthopyridyl disulfide (OPSS), thiol, or halogen.

In another specific embodiment, the method includes:

a first step for preparing a compound represented by Formula 21 below from a compound represented by Formula 20 below;

a second step for preparing a compound represented by Formula 22 below from a compound represented by Formula 21 below; and a third step for converting the diethoxy methyl at an end of a compound represented by Formula 22 below into aldehyde by treating the compound represented by Formula 22 with an acid solution:

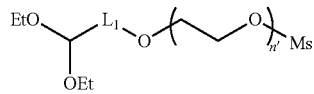

[Formula 20]

wherein, in Formula 20 above, n' is n or n+1; and

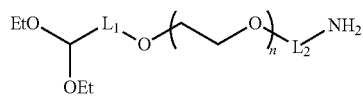

[Formula 21]

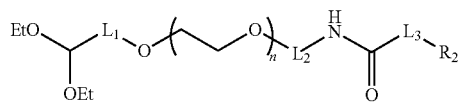

[Formula 22]

wherein L$_1$, L$_2$, L$_3$, n, and R$_2$ are the same as described above.

In still another specific embodiment, the compound represented by Formula 20 of the first step is prepared by reacting the compound represented by Formula 23 below with methanesulfonyl chloride:

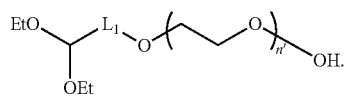

[Formula 23]

In still another specific embodiment, the first step is performed by reacting the compound represented by Formula 20 with an aqueous ammonia solution and ammonium chloride.

In still another specific embodiment, the first step includes:

step 1-1, which is to react a compound represented by Formula 20 with hydroxyalkyl tetrahydropyranyl ether, thereby preparing a compound represented by Formula 24;

step 1-2, which is to react a compound represented by Formula 24 with p-toluenesulfonic acid, thereby substituting the tetrahydropyranyloxy group at an end thereof with a hydroxy group;

step 1-3, which is to react the compound obtained in step 1-2 with methanesulfonyl chloride, thereby substituting the hydroxy group with a methanesulfonic acid group; and step 1-4, which is to react the compound obtained in step 1-3 with an aqueous ammonia solution and ammonium chloride.

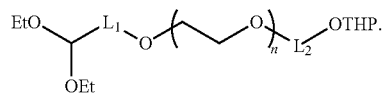

[Formula 24]

In still another specific embodiment, the second step is performed by reacting a compound represented by Formula 21 with a compound represented by Formula 25:

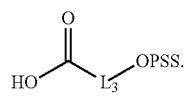

[Formula 25]

In still another specific embodiment, the second step includes: reacting a compound represented by Formula 21 with chloro(C$_{2-7}$ alkanoyl) chloride, thereby synthesizing a compound comprising a chloro group at an end thereof, which is represented by Formula 26 below, as an intermediate product; and reacting the compound represented by Formula 26 with a halogen metal salt in the presence or absence of hydrogen sulfide, thereby converting the chloro group into thiol or halogen:

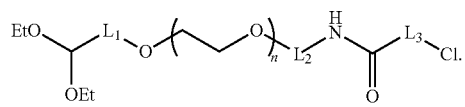

[Formula 26]

Still another aspect of the present invention provides a use of the polyethylene glycol compound for linking a carrier, which is capable of increasing an in vivo half-life of a physiologically active polypeptide, to a physiologically active polypeptide.

Still another aspect of the present invention provides a composition containing a physiologically active polypeptide to which the polyethylene glycol compound is attached or the conjugate.

Still another aspect of the present invention provides a linker for linking a carrier capable of increasing an in vivo half-life of a physiologically active polypeptide to a physiologically active polypeptide, wherein the linker includes a polyethylene glycol compound, a stereoisomer thereof, or a pharmaceutically acceptable salt thereof.

Advantageous Effects

The polyethylene glycol derivatives of the present invention have advantages in that they include desired reactive end groups at an end thereof, and at the same time, they can easily react with target materials (e.g., proteins) to be linked thereto. Accordingly, the polyethylene glycol derivatives of the present invention can be effectively used in the field of manufacturing medicaments with regard to conjugated drugs such as protein conjugates, etc.

BRIEF DESCRIPTION OF DRAWINGS

FIGS. 1a and 1b show exemplary embodiments of novel polyethylene glycol compounds of the present invention, illustrating the chemical structures of the compounds having an aldehyde group and an ortho-pyridyl disulfide group (linkers #1, #4, and #7), 2) the chemical structures of the compounds having an aldehyde group and an iodoacetamide group or iodine group (linkers #2, #5, and #8), and 3) the chemical structures of the compounds having an aldehyde group and a sulfhydryl group (linkers #3, #6, and #9). In FIG. 1b, linkers #10 to #12 correspond to comparative groups.

FIG. 18 shows the results of comparative experiments with regard to the reactivity of the thiol reactive groups of the polyethylene glycol compounds according to the present invention.

FIGS. 19 to 21 show the results of SDS-PAGE analyses with regard to the conjugates of triple agonist-PEG-Fc prepared using the polyethylene glycol compounds according to the present invention as a linker, in which FIG. 19 shows the result of SDS-PAGE analysis using linker #7 according to the present invention, FIG. 20 using linker #8, and FIG. 21 using linker #9, respectively.

DETAILED DESCRIPTION OF THE INVENTION

Figure 2:
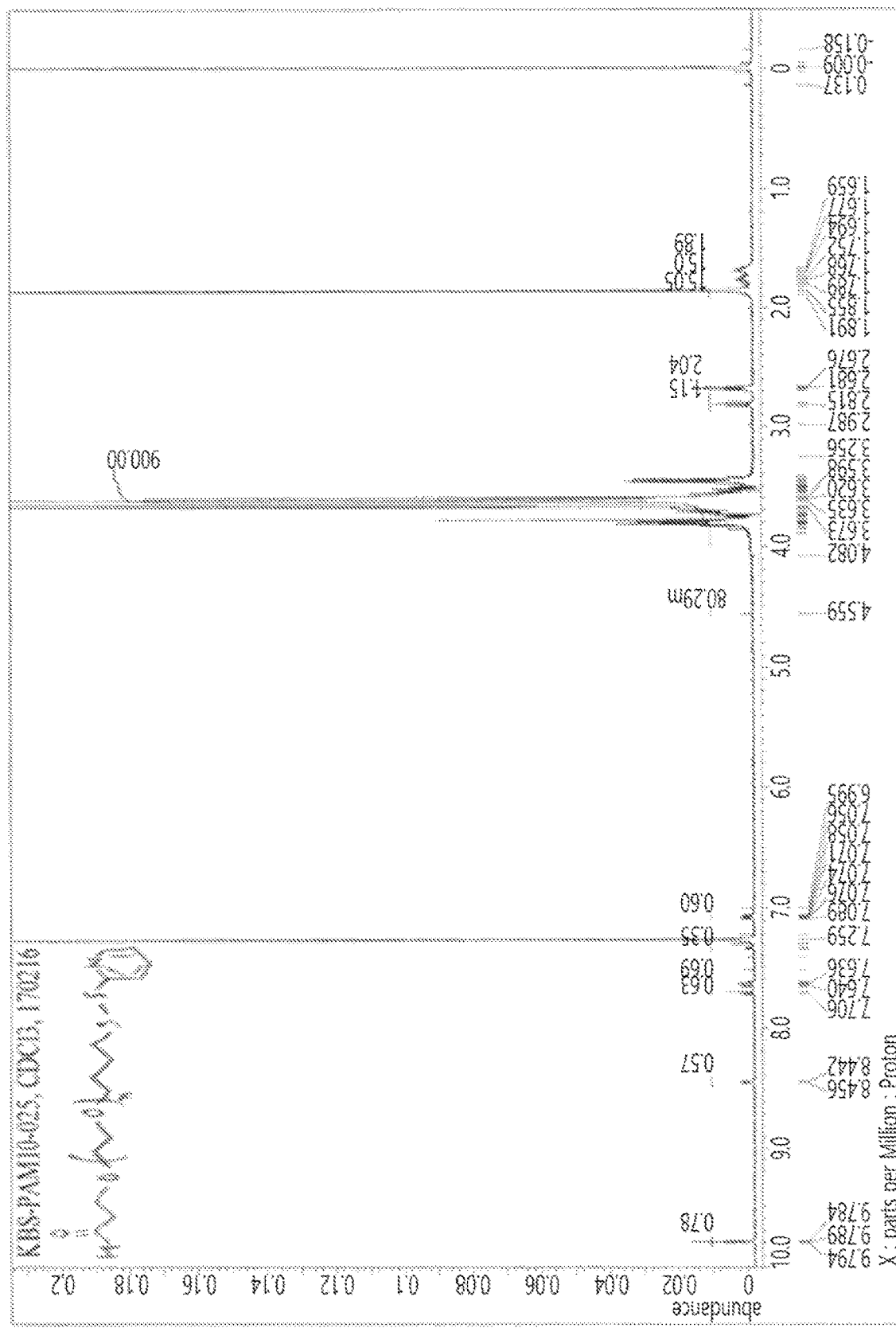
FIG. 2 shows the result of nuclear magnetic resonance (hereinafter, NMR) analysis confirming linker #1 after its preparation.
Figure 3:
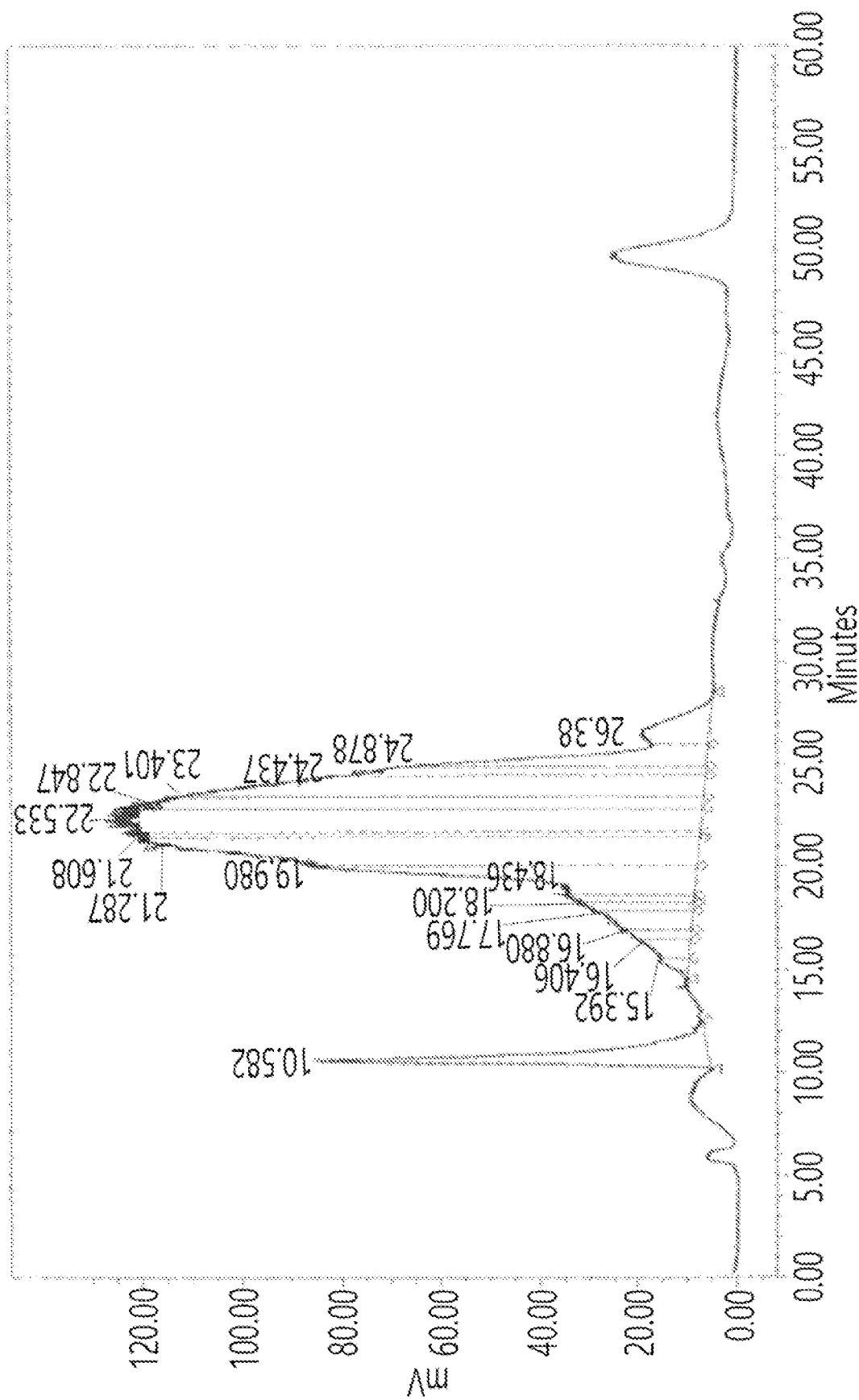
FIG. 3 shows the result of reversed phase chromatography (hereinafter, RPC) analysis of linker #1 after its preparation.
Figure 4:
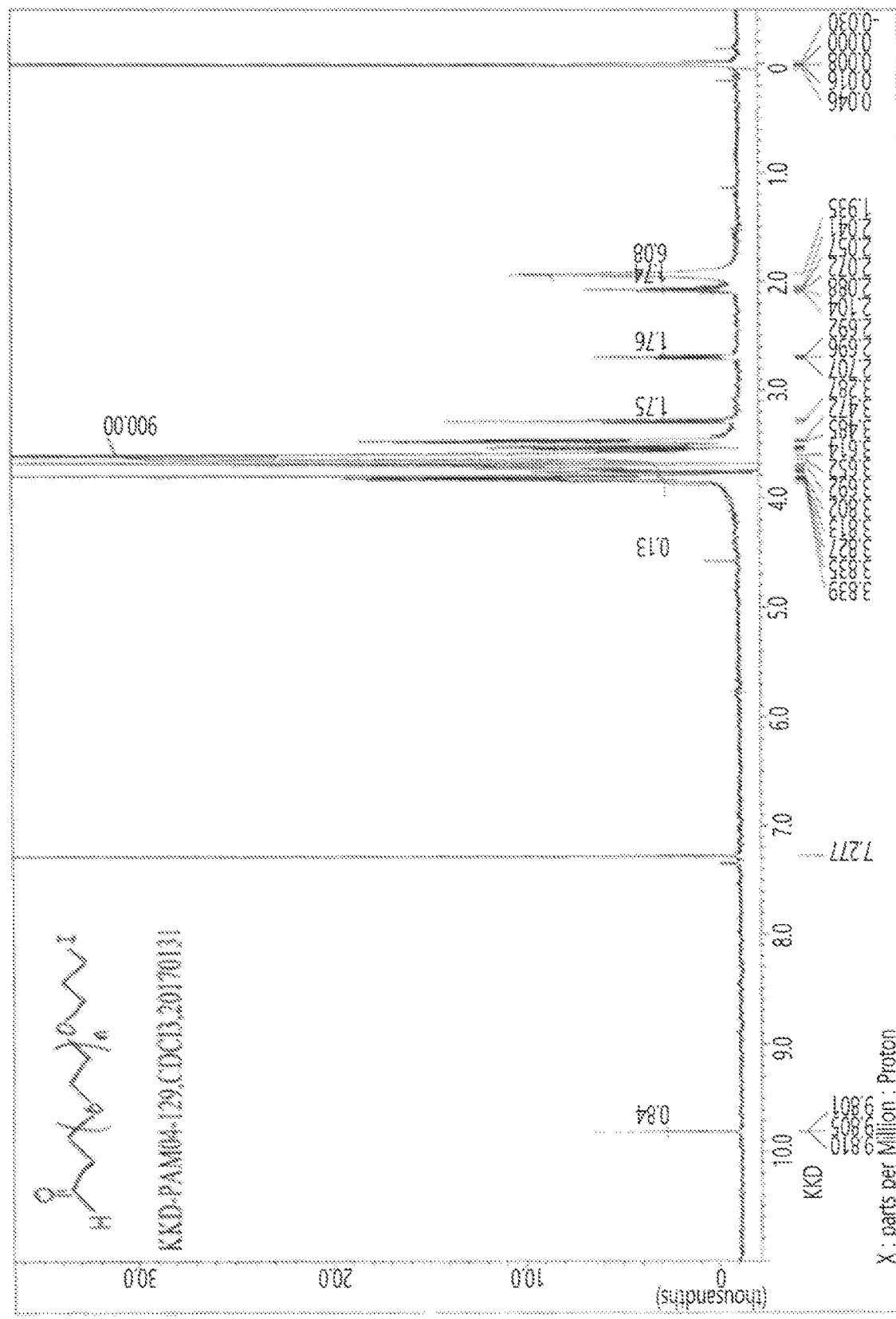
FIG. 4 shows the result of NMR analysis confirming linker #2 after its preparation.
Figure 5:
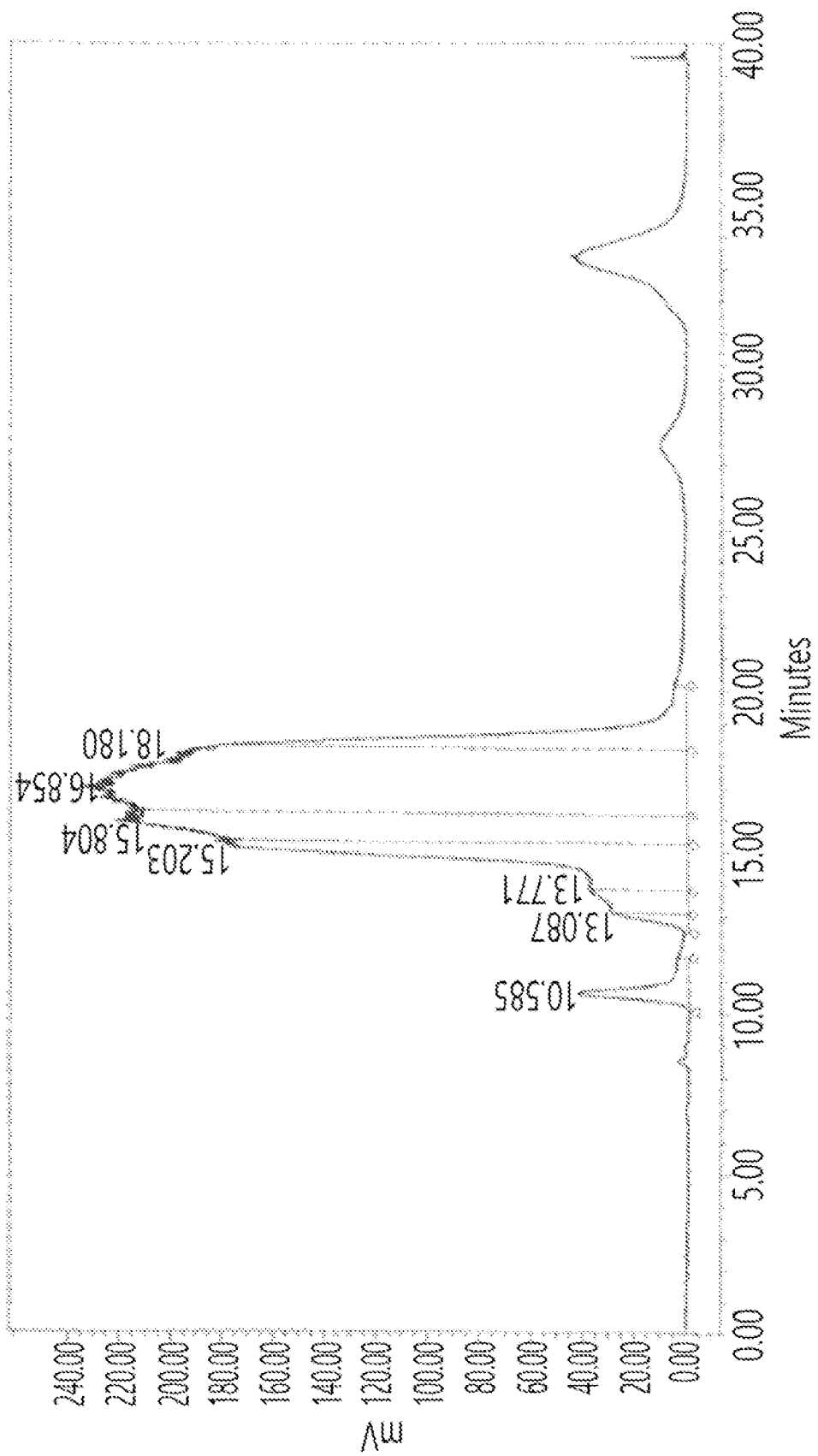
FIG. 5 shows the result of RPC analysis of linker #2 after its preparation.
Figure 6:
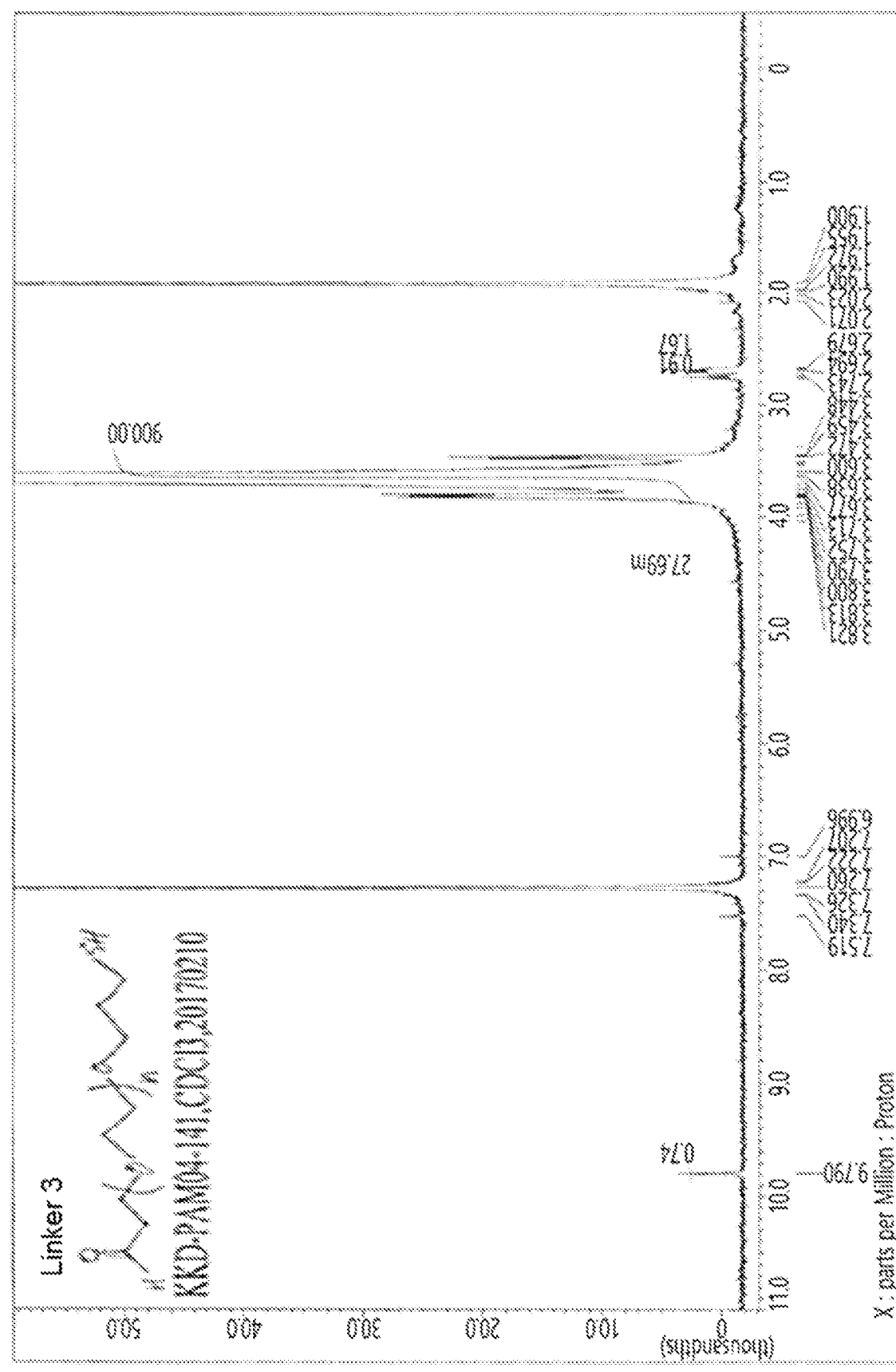
FIG. 6 shows the result of NMR analysis confirming linker #3 after its preparation.
Figure 7:
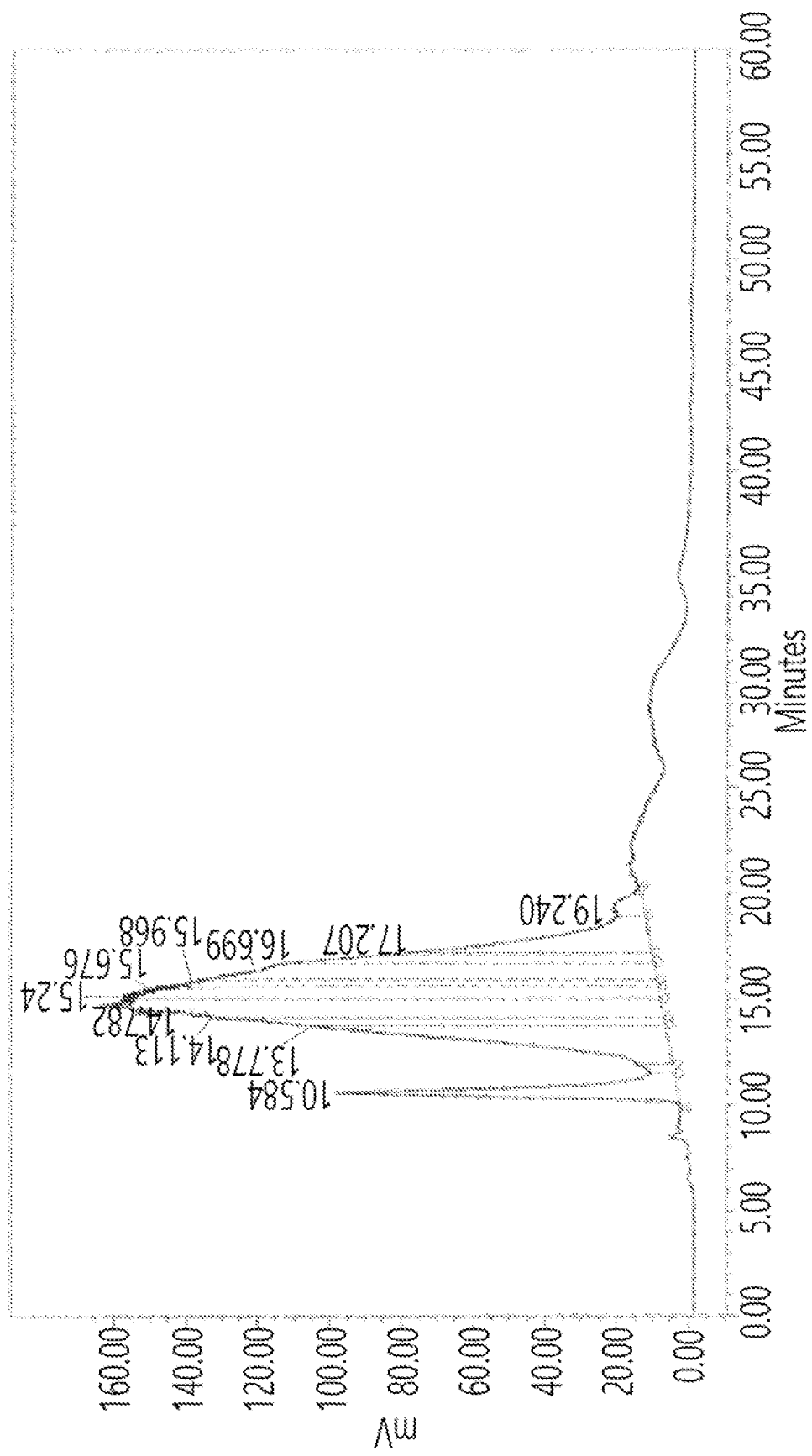
FIG. 7 shows the result of RPC analysis of linker #3 after its preparation.
Figure 8:
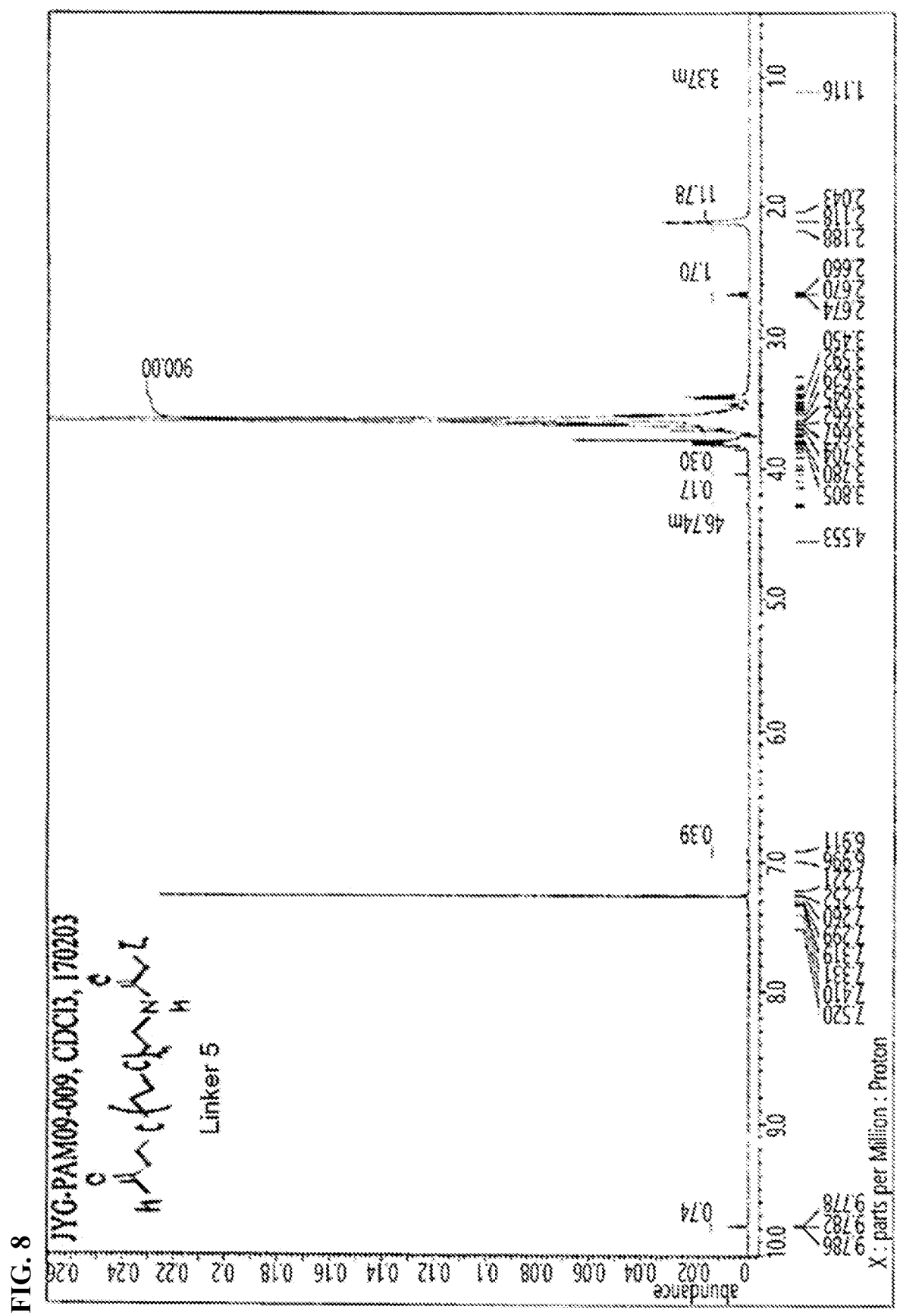
FIG. 8 shows the result of NMR analysis confirming linker #5 after its preparation.
Figure 9:
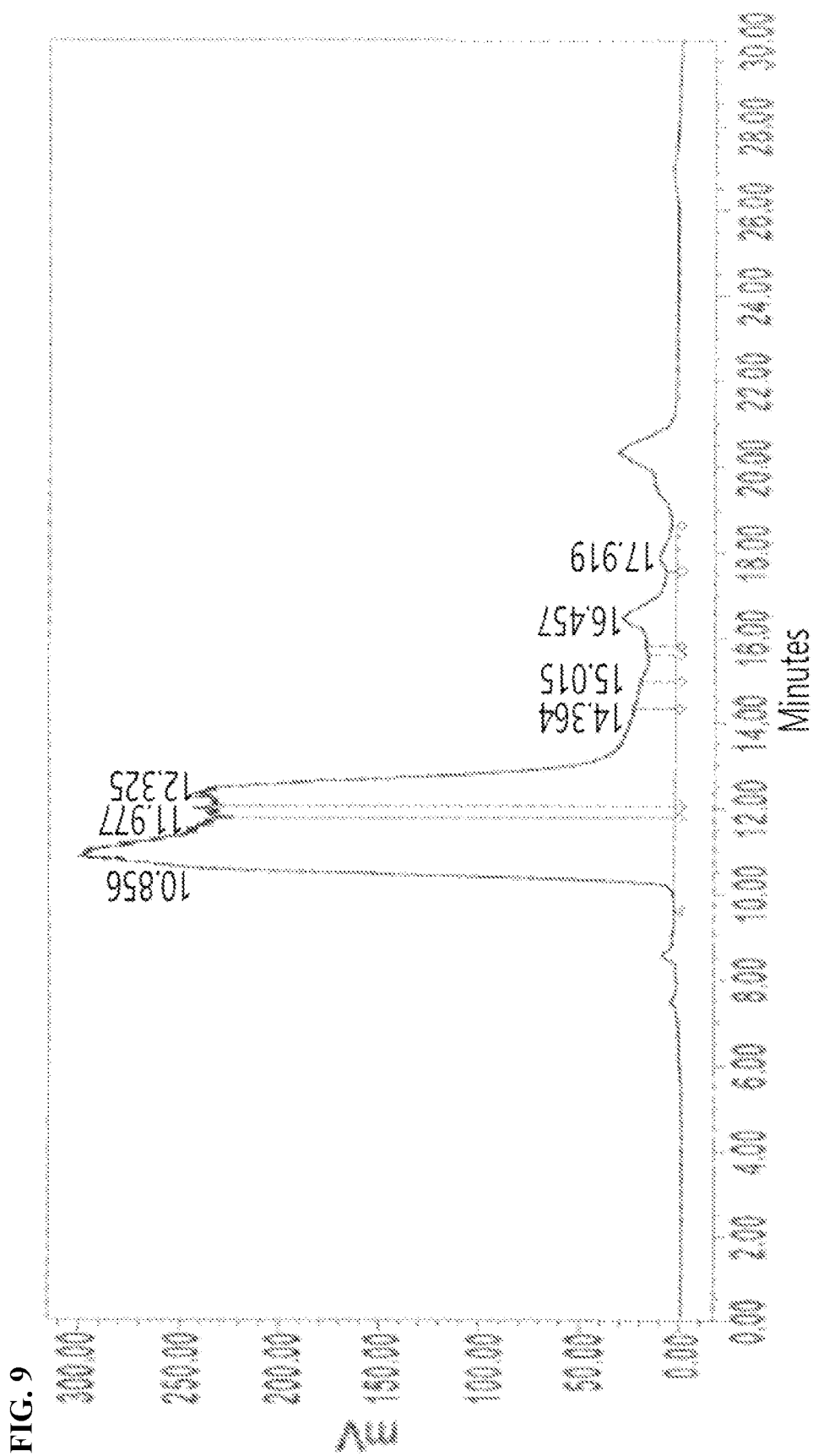
FIG. 9 shows the result of RPC analysis of linker #5 after its preparation.
Figure 10:
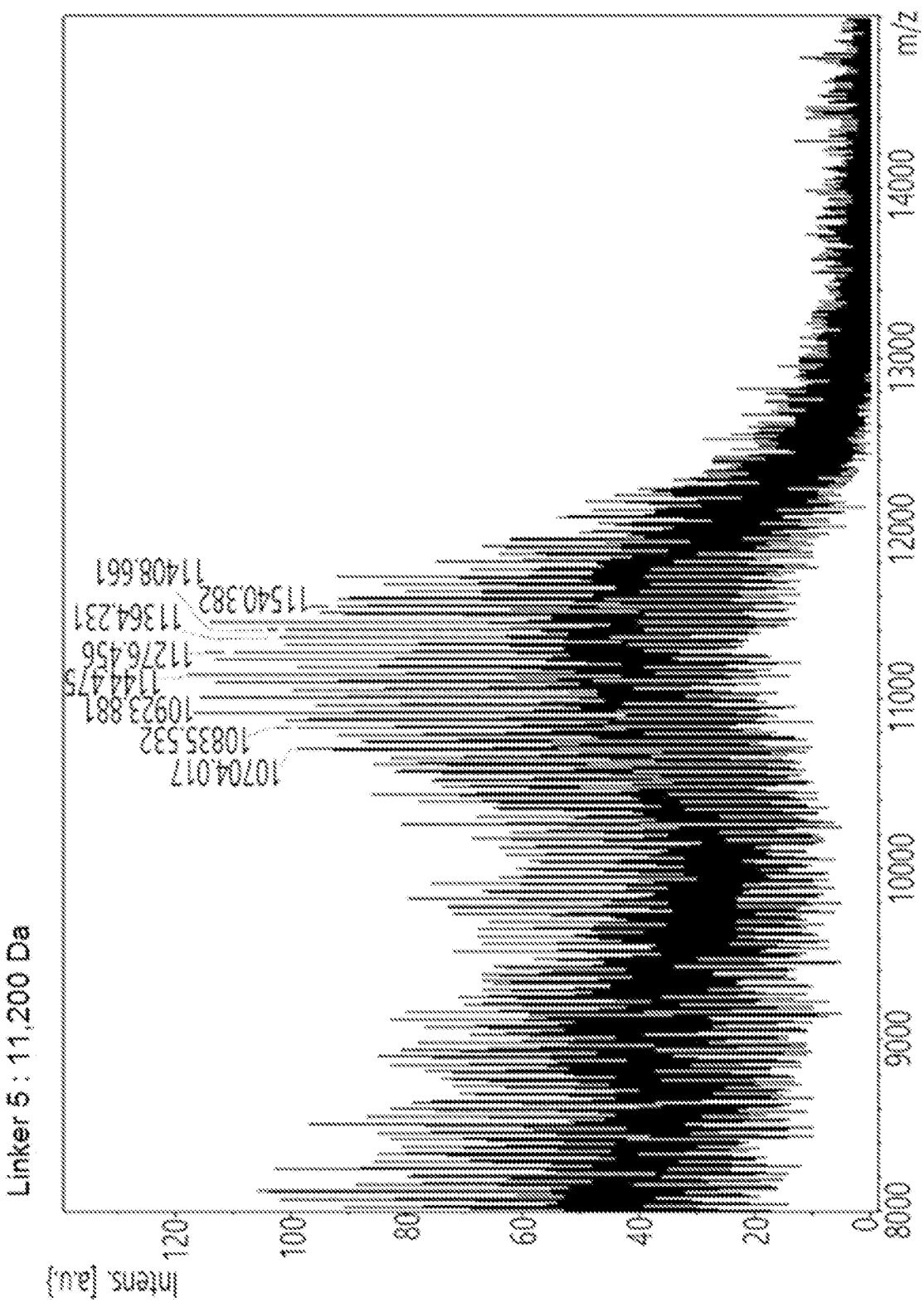
FIG. 10 shows the result of MALDI-TOF analysis of the molecular weight of linker #5 after its preparation.
Figure 11:
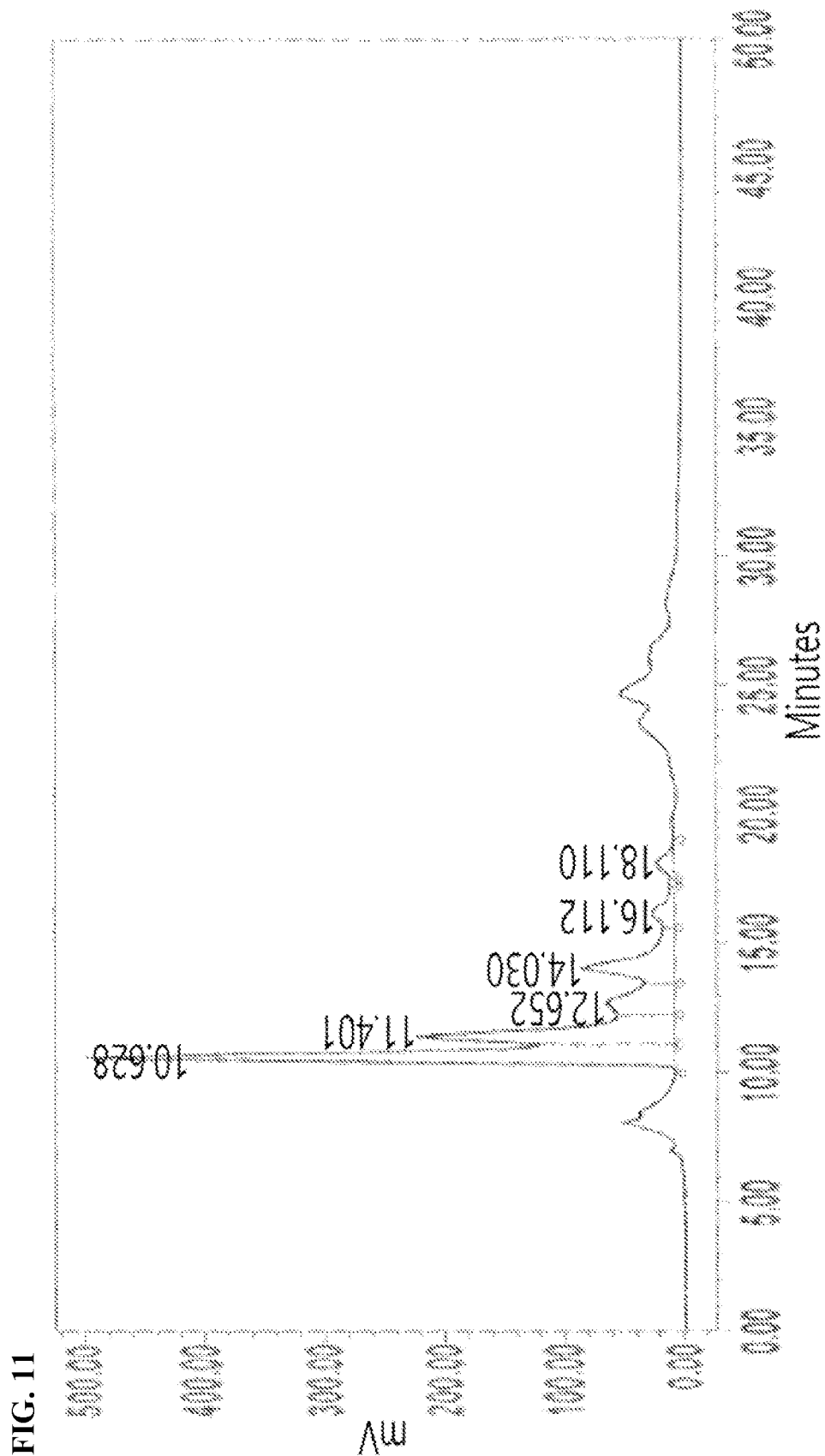
FIG. 11 shows the result of RPC analysis of linker #7 after its preparation.
Figure 12:
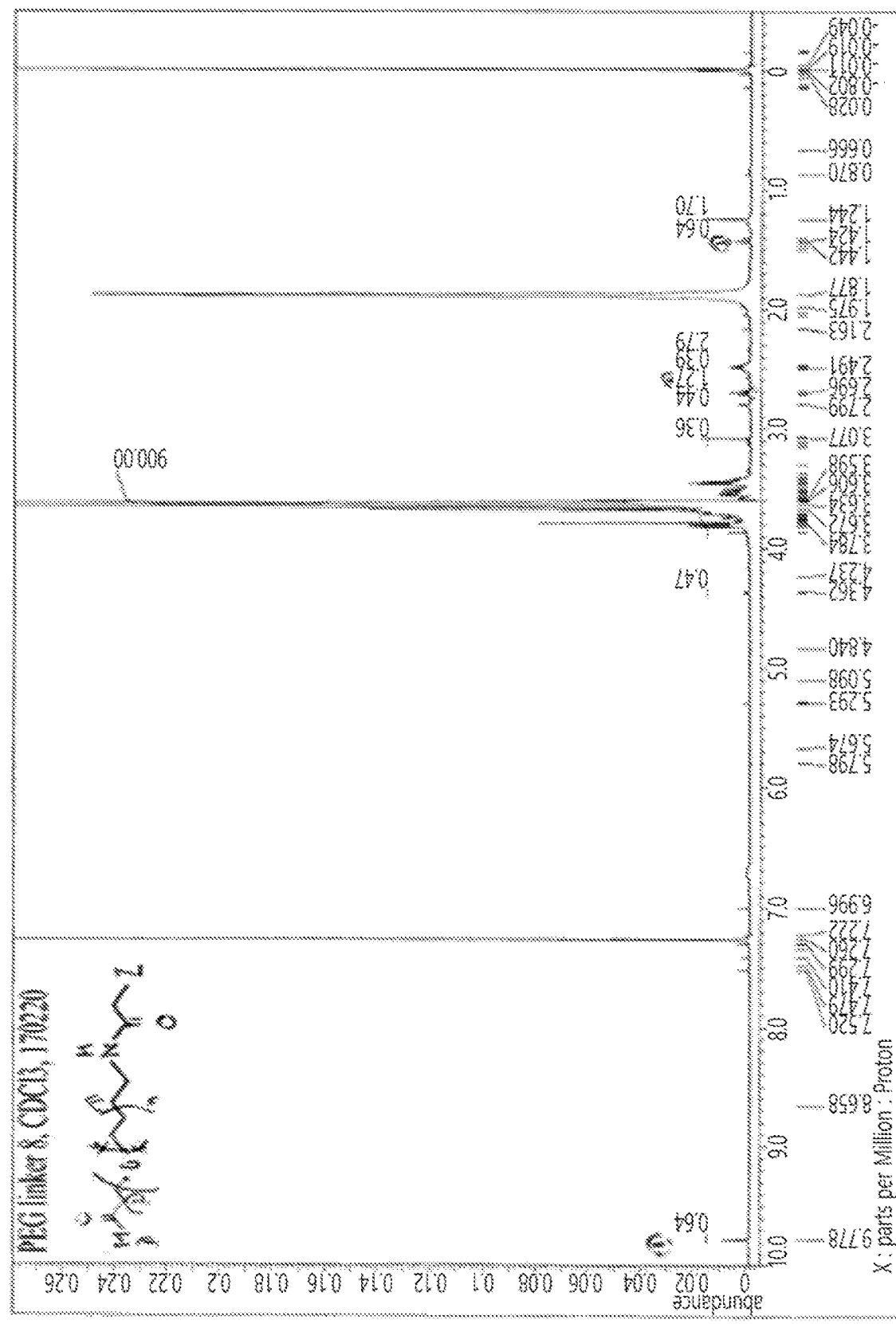
FIG. 12 shows the result of NMR analysis confirming linker #8 after its preparation.
Figure 13:
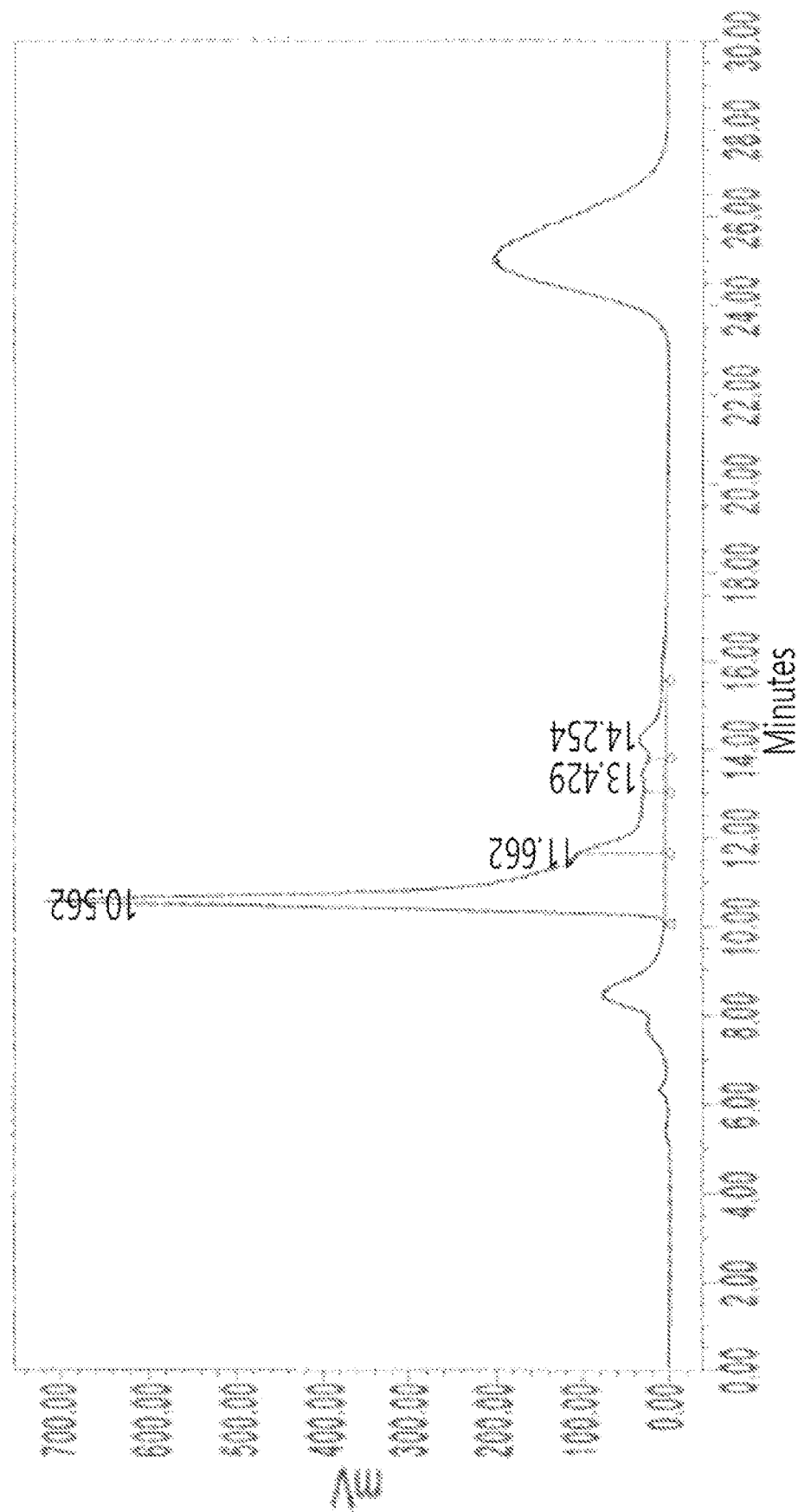
FIG. 13 shows the result of RPC analysis of linker #8 after its preparation.
Figure 14:
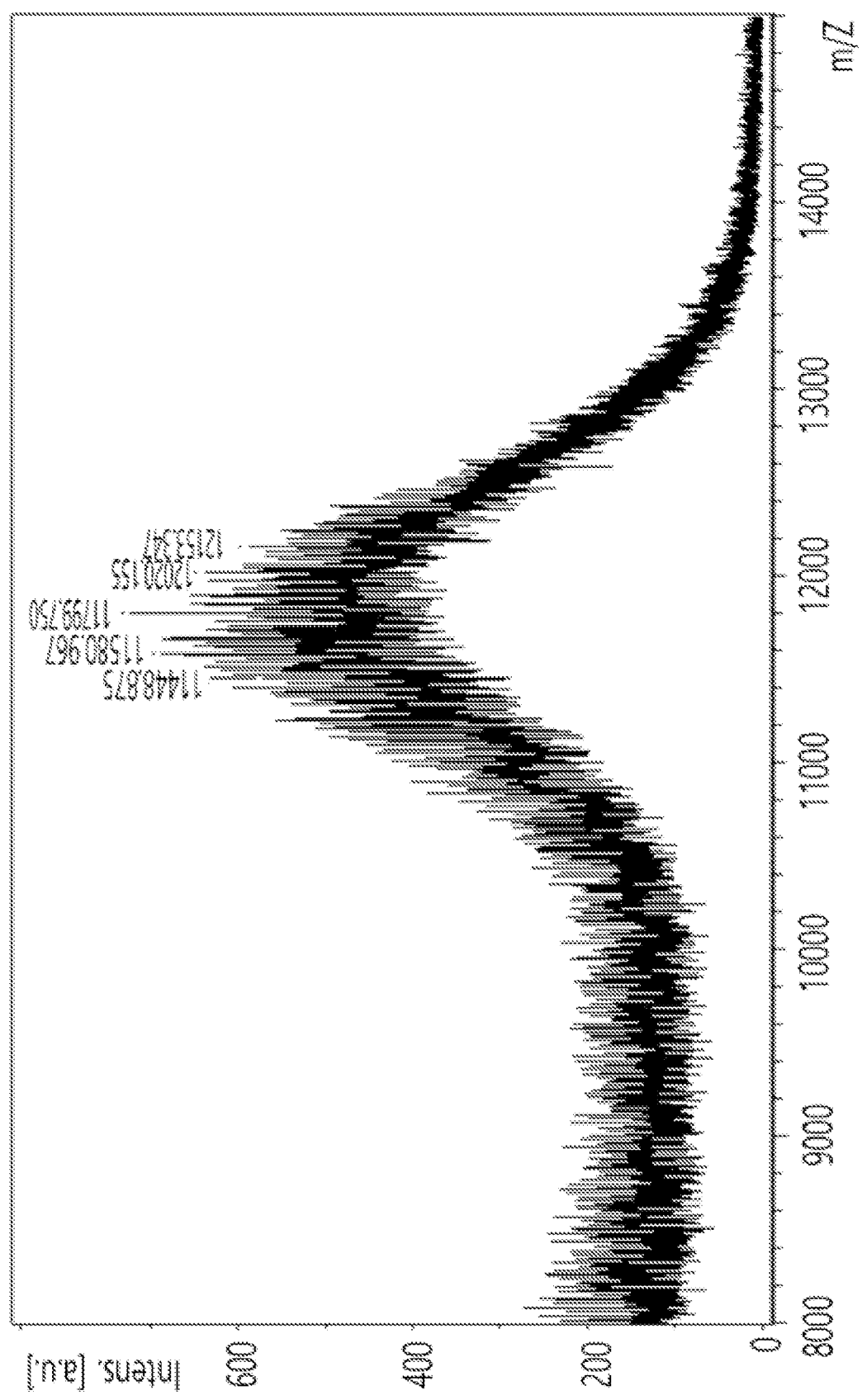
FIG. 14 shows the result of MALDI-TOF analysis of the molecular weight of linker #8 after its preparation.
Figure 15:
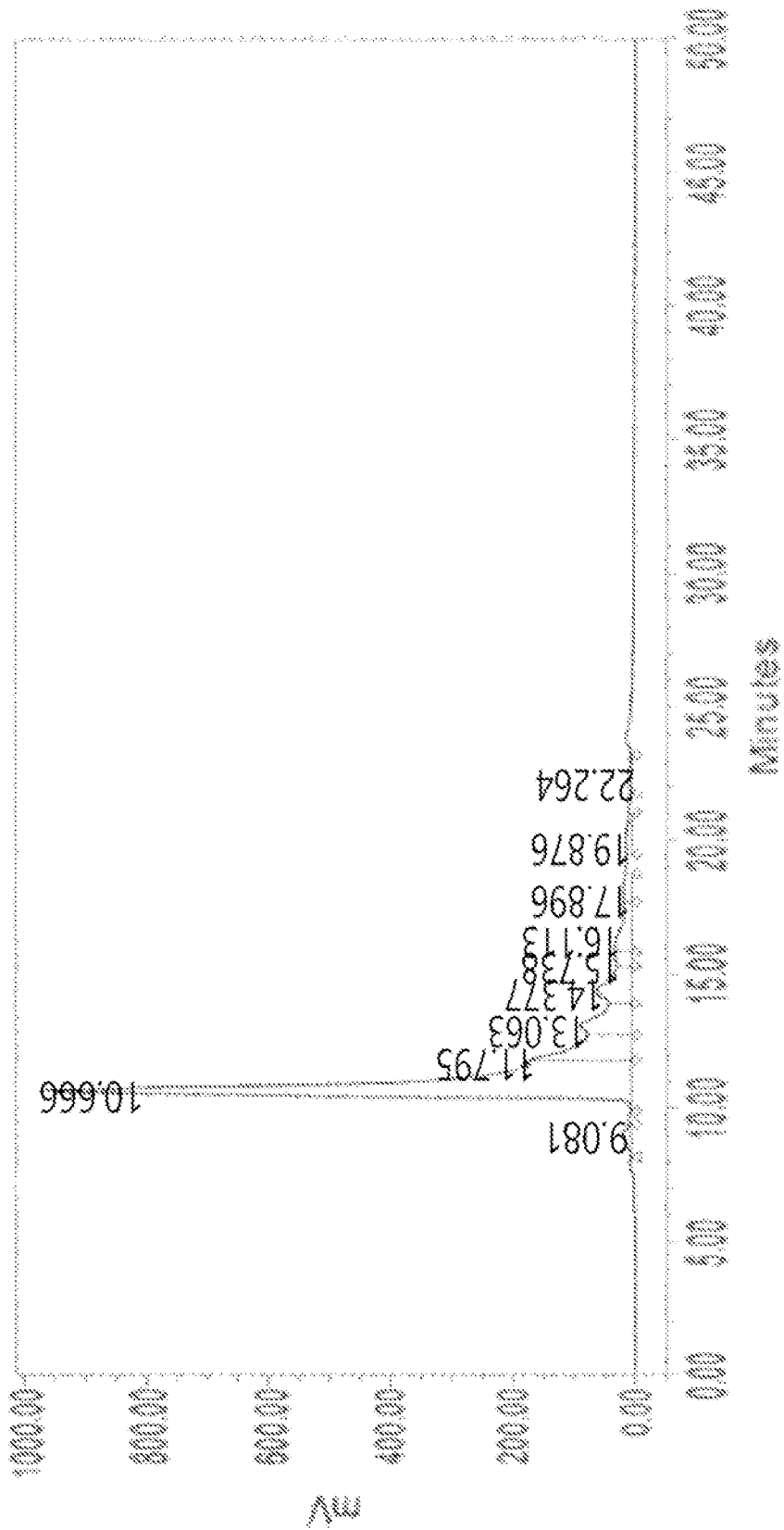
FIG. 15 shows the result of RPC analysis of linker #9 after its preparation.
Figure 16:
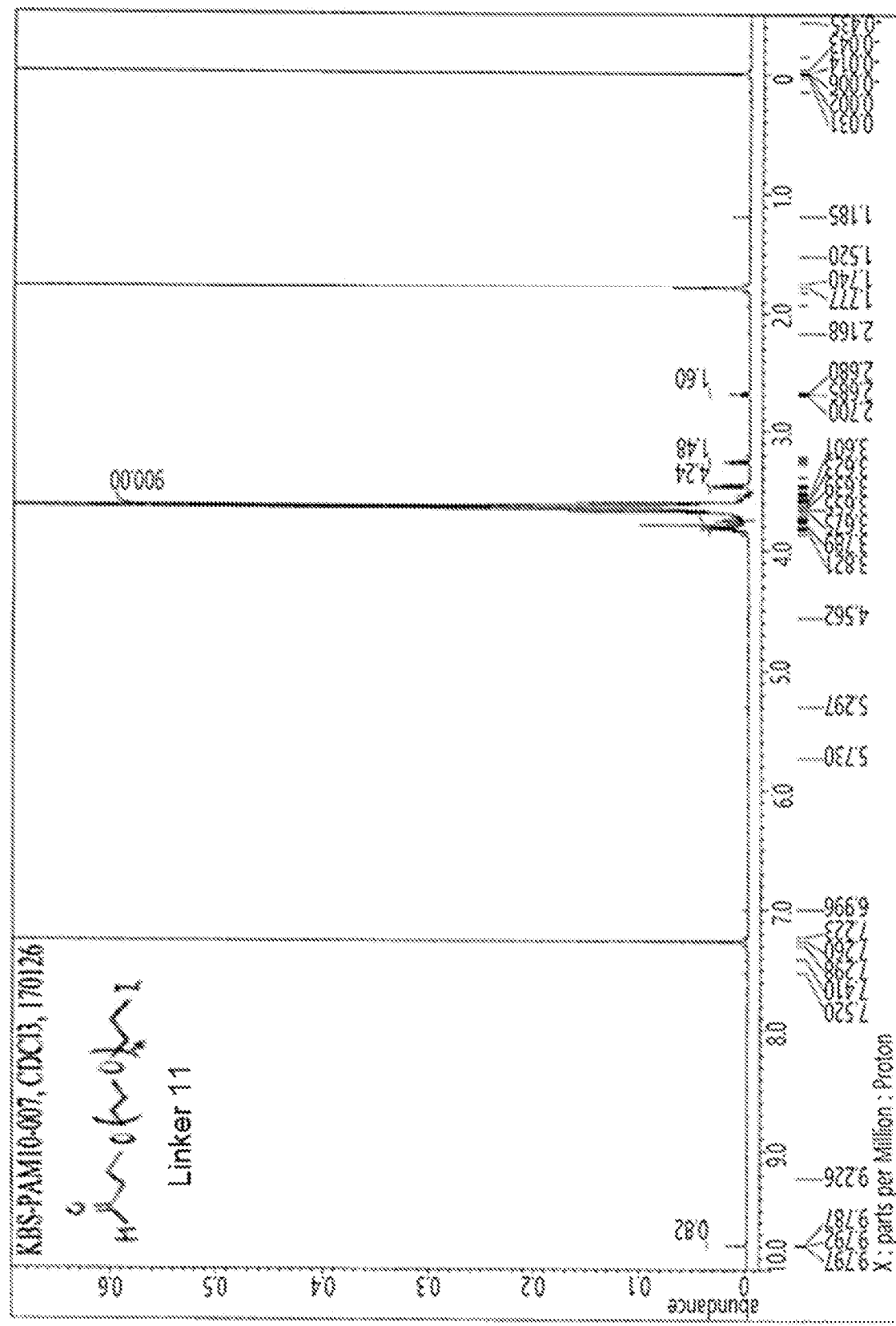
FIG. 16 shows the result of NMR analysis confirming linker #11 after its preparation.
Figure 17:
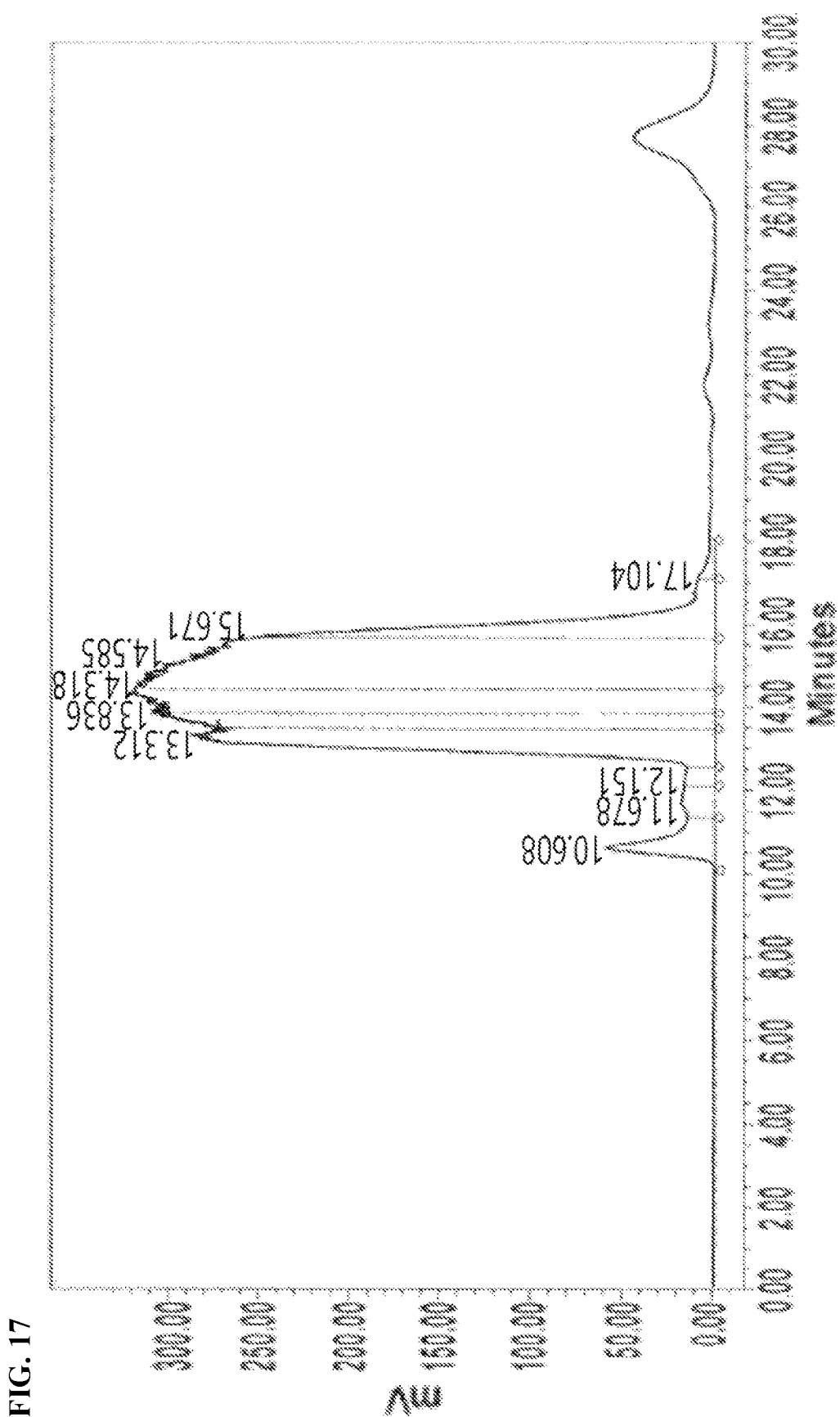
FIG. 17 shows the result of RPC analysis of linker #11 after its preparation.

An aspect of the present invention provides a polyethylene glycol compound, a stereoisomer thereof, or a pharmaceutically acceptable salt thereof.

Hereinafter, the present invention is described in detail. Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided hereinbelow.

As used herein, the term "polyethylene glycol compound" refers to a compound including the structure of a polyethylene glycol, $[-(OCH_2CH_2)_n-]$. More specifically, in the present invention, the polyethylene glycol compound may include two reactive end groups.

In particular, the two or more reactive end groups present in the polyethylene glycol compound may be the same or different with each other. More specifically, the polyethylene glycol compound may be a heterofunctional linker that acts on mutually different reactive end groups. For example, one end of the compound may have a functionality on the amine group while the other end may have a functionality on the thiol group, but the polyethylene glycol compounds are not particularly limited thereto.

Additionally, the polyethylene glycol compound may be used as a linker for linking a carrier to a physiologically active polypeptide. Accordingly, one end of the polyethylene glycol compound, which has two or more reactive end groups, may be linked to a physiologically active polypeptide while the other end of the polyethylene glycol compound may be linked to a carrier.

Meanwhile, the polyethylene glycol compound and polyethylene glycol derivatives may be used interchangeably in the present invention.

In a specific embodiment, the polyethylene glycol compound according to the present invention may be one which includes the structure of —NHCO— between a thiol reactive group and the structure of a polyethylene glycol as shown below.

Specifically, the compound may be a compound represented by Formula 1 below:

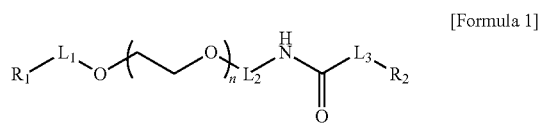

[Formula 1]

wherein, in Formula 1 above, $R_1$ is selected from 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In Formula 1 above, $R_2$ may be ortho-pyridyl disulfide, thiol, F, Br, Cl, or I, and more specifically, ortho-pyridyl disulfide or I, but is not particularly limited thereto.

In Formula 1 above, $R_1$ may be aldehyde, but is not particularly limited thereto.

In Formula 1 above, $R_1$ may be a succinimide derivative, and the kinds of the succinimide derivative may include succinimidyl propionate, hydroxy succinimidyl, succinimidyl carboxymethyl, and succinimidyl carbonate, but are not particularly limited thereto.

Additionally, the compound may be heterofunctional, acting on mutually different reactive end groups, and specifically, $R_1$ and $R_2$ may have mutually different functional groups, but the compound is not particularly limited thereto.

Specifically, $R_1$ may be aldehyde and $R_2$ may be ortho-pyridyl disulfide (OPSS), thiol, or halogen, but the compound is not particularly limited thereto.

In the above compound, each of $L_1$ to $L_3$ may be independently a linear or branched $C_{1-6}$ alkylene, and more specifically, $C_{1-4}$ alkylene, but is not particularly limited thereto.

For example, $L_1$ may be an integer of 1, 2, 3, 4, 5, or 6; $L_2$ may be an integer of 1, 2, 3, 4, 5, or 6; and $L_3$ may be an integer of 1, 2, 3, 4, 5, or 6.

In an embodiment, $L_2$ may be 2, 4, or 6, whereas $L_1$ and $L_3$ may be 1, 2, 3, 4, 5, or 6.

In the above compound, $R_1$-$L_1$- may be alkyl aldehyde, e.g., $C_{2-6}$ alkyl aldehyde, and specifically, propionaldehyde, butyraldehyde, etc., but is not particularly limited thereto.

Additionally, the polyethylene glycol compound of the present invention may have a molecular weight of about 100 dalton to about 110,000 dalton, specifically about 400 dalton to about 110,000 dalton, more specifically about 1,000 dalton to about 100,000 dalton, and even more specifically about 1,000 dalton to about 20,000 dalton, but is not particularly limited thereto.

In Formula 1 above, n may be an integer of 10 to 2400, and specifically an integer of 20 to 460, but is not particularly limited thereto.

Specifically, the compound may be a compound represented by Formula 2 below:

$$CHO(CH_2)_j\text{—}O\text{—}(CH_2CH_2O)_n\text{—}(CH_2)CH_n\text{—}(C_m\text{—}NH(CO)\text{—}(CH_2)_k\text{—}R_2 \quad \text{[Formula 2]}$$

Wherein, in Formula 2 above, n is an integer of 10 to 2400, each of j, m, and k is independently an integer of 1 to 6, and $R_2$ is ortho-pyridyl disulfide, thiol, or halogen.

More specifically, in Formula 2 above, n may be an integer of 10 to 2400, and even more specifically an integer of 20 to 460, but is not particularly limited thereto.

In a specific embodiment, each of j, m, and k may be independently an integer of 1 to 6, and specifically an integer of 1 to 4.

For example, j may be an integer of 1, 2, 3, 4, 5, or 6; m may be an integer of 1, 2, 3, 4, 5, or 6; and k may be an integer of 1, 2, 3, 4, 5, or 6.

In an embodiment, j may be 2, 3, 4, 5, or 6; whereas m may be 2, 4, or 6; and k may be 1, 2, 3, 4, 5, or 6.

Additionally, $R_2$ may be ortho-pyridyl disulfide, thiol, or halogen; specifically ortho-pyridyl disulfide, thiol, or F, Br, Cl, or I; and more specifically ortho-pyridyl disulfide or I, but is not particularly limited thereto.

Specifically, the compound may be a compound selected from Formulas 6 to 11 below.

[Formula 6]

[Formula 7]

[Formula 8]

[Formula 9]

[Formula 10]

[Formula 11]

In Formulas 6 to 11, n is the same as defined above.

In Examples of the present invention, the compound represented by Formula 6 was named as linker #4; the compound represented by Formula 7 was named as linker #5; the compound represented by Formula 8 was named as linker #6; the compound represented by Formula 9 was named as linker #7; the compound represented by Formula 10 was named as linker #8; and the compound represented by Formula 11 was named as linker #9, respectively.

In an embodiment of the present invention, it was confirmed that the compounds belonging to Formula 1 above can exhibit a higher reactivity to a thiol group compared to the above compound which do not include —NHCO— structure. Therefore, the compounds belonging to Formula 1 above can be effectively used for attaching to materials including a thiol group.

Meanwhile, the compound may specifically have any one structure selected from Formulas 3 to 5 below:

[Formula 3]

[Formula 4]

[Formula 5]

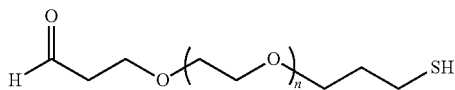

wherein n is the same as defined above.

Meanwhile, the compound may be present in the form of a pharmaceutically acceptable salt. As a salt, an acid addition salt formed by a pharmaceutically acceptable free acid is useful.

The kind of the salt is not particularly limited. However, the salt is preferably one that is safe and effective to a subject, e.g., a mammal, but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

Acid addition salts may be prepared by a conventional method, for example, a method of dissolving a compound in an excess aqueous acid solution followed by precipitating the resulting salt using a water-miscible organic solvent (e.g., methanol, ethanol, acetone, or acetonitrile). An equimolar amount of the compound and the acid or alcohol in water (e.g., glycol monomethyl ether) may be heated, and subsequently, the mixture may be evaporated and dried or the educed salt may be subjected to suction filtration.

Additionally, a pharmaceutically acceptable metal salt may be prepared using a base. An alkali metal salt or alkali earth metal salt may be prepared, for example, by dissolving a compound in an excess amount of an alkali metal hydroxide or alkali earth metal hydroxide solution, filtering the non-dissolved compound salt, and evaporating the filtrate, followed by drying.

Additionally, the compound of the present invention and a pharmaceutically acceptable salt thereof is a concept which includes solvates that can be prepared therefrom.

As used herein, the term "solvate" refers to a complex which is formed between the compound according to the present invention or a salt thereof and a solvent molecule.

Furthermore, when the compound of the present invention has an asymmetric carbon center in its substituent, the compound may exist as an (R) or (S) isomer, a racemate, a mixture of a diastereomer, and an individual diastereomer, and all of these isomers and mixtures thereof belong to the scope of the present invention.

Still another aspect of the present invention provides a method for preparing a physiologically active polypeptide to which a polyethylene glycol compound is attached, which includes reacting a polyethylene glycol compound with a physiologically active polypeptide to prepare a physiologically active polypeptide to which a polyethylene glycol compound is attached.

The polyethylene glycol compounds are the same as explained above.

The above method may include linking any one of the reactive end groups, which are located at both ends of the polyethylene glycol compound, to a physiologically active polypeptide. More specifically, the reactive end group located at $R_1$ may be linked to the physiologically active polypeptide; or the reactive end group located at $R_2$ may be linked to the physiologically active polypeptide, but the method is not limited thereto.

More specifically, the method may include reacting orthopyridyl disulfide, thiol, or halogen, which are located at $R_2$, with a thiol group located at the cysteine residue of the physiologically active polypeptide, but the method is not limited thereto.

The reaction between the polyethylene glycol compound and physiologically active polypeptide may be appropriately determined by one of ordinary skill in the art, in consideration of the characteristics of the reactive end group of polyethylene glycol compound and the characteristics of the reactive groups of the physiologically active polypeptide, to which polyethylene glycol compound is to be linked.

For example, the reaction may be performed in the presence of a citrate buffer or HEPES buffer or an organic solvent such as $C_{1-6}$ alcohol, but is not particularly limited thereto.

Additionally, the method may further include purifying the physiologically active polypeptide to which a polyethylene glycol compound is attached.

For the purification, any known method in the art may be used without limitation, and specifically chromatography may be used, but the purification method is not particularly limited thereto.

As used herein, the term "physiologically active polypeptide" refers to a concept including peptides or proteins capable of exhibiting physiological activities, and preferably refers to materials whose physiological activities are to be exhibited in a subject.

The physiologically active polypeptide is to be selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

Examples of the physiologically active polypeptide may include GLP-1 receptor agonist, leptin receptor agonist, DPP-IV inhibitor, Y5 receptor antagonist, melanin-concentrating hormone (MCH) receptor antagonist, Y2/3 receptor agonist, MC3/4 receptor agonist, gastric/pancreatic lipase inhibitor, 5HT2c agonist, β3A receptor agonist, amylin receptor agonist, ghrelin antagonist, ghrelin receptor antagonist, etc., but are not particularly limited thereto.

Additionally, the physiologically active polypeptide may be a peptide which includes the amino acid sequence represented by the sequences below, or essentially consists of the sequences thereof, or consists of the sequences thereof. The peptide may have an activity on glucagon receptors, GLP-1 receptors, and GIP receptors, and these peptides are named as triple agonists.

Xaa1-Xaa2-Xaa3-Gly-Thr-Phe-Xaa7-Ser-Asp-Xaa10-Ser-Xaa12-Xaa13-Xaa14-Xaa15-Xaa16-Xaa17-Xaa18-Xaa19-Xaa20-Xaa21-Phe-Xaa23-Xaa24-Trp-Leu-Xaa27-Xaa28-Xaa29-Xaa30-$R_1$ (SEQ ID NO: 103)

In the Formula above,
Xaa1 is histidine, 4-imidazoacetyl, or tyrosine,
Xaa2 is glycine, α-methyl-glutamic acid, or Aib,
Xaa3 is glutamic acid or glutamine,
Xaa7 is threonine or isoleucine,
Xaa10 is leucine, tyrosine, lysine, cysteine, or valine,
Xaa12 is lysine, serine, or isoleucine,
Xaa13 is glutamine, tyrosine, alanine, or cysteine,
Xaa14 is leucine, methionine, or tyrosine,
Xaa15 is cysteine, aspartic acid, glutamic acid, or leucine,
Xaa16 is glycine, glutamic acid, or serine,
Xaa17 is glutamine, arginine, isoleucine, glutamic acid, cysteine, or lysine,
Xaa18 is alanine, glutamine, arginine, or histidine,
Xaa19 is alanine, glutamine, cysteine, or valine,
Xaa20 is lysine, glutamine, or arginine,
Xaa21 is glutamic acid, glutamine, leucine, cysteine, or aspartic acid,
Xaa23 is isoleucine or valine,
Xaa24 is alanine, glutamine, cysteine, asparagine, aspartic acid, or glutamic acid,
Xaa27 is valine, leucine, lysine, or methionine,
Xaa28 is cysteine, lysine, alanine, asparagine, or aspartic acid,
Xaa29 is cysteine, glycine, glutamine, threonine, glutamic acid, or histidine,
Xaa30 is cysteine, glycine, lysine, or histidine, or is absent, and
$R_1$ is cysteine, GKKNDWKHNIT (SEQ ID NO: 104), m-SSGAPPPS-n (SEQ ID NO: 105), or m-SSGQPPPS-n (SEQ ID NO: 106), or is absent,
wherein:
m is -Cys-, -Pro-, or -Gly-Pro-, and
n is -Cys-, -Gly-, -Ser-, or -His-Gly-, or is absent.

Examples of the triple agonists may include a peptide including the amino acid sequence selected from SEQ ID NOS: 1 to 102, but are not particularly limited thereto.

Additionally, the physiologically active polypeptide may be selected from selected from the group consisting of glucagon; insulin; somatostatin; peptide YY (PYY); neuropeptide Y (NPY); glucagon-like peptides including glucagon-like peptide-1 (GLP-1) and glucagon-like peptide-2 (GLP-2); exendin-3; exendin-4; oxyntomodulin; peptides having an activity on glucagon receptors, GLP-1 receptors, and GIP receptors; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); growth hormone-releasing peptides; granulocyte-colony-stimulating factors (GCSF); interferons (IFNs); interleukins; prolactin-releasing peptides; orexin; thyroid-releasing peptides; cholecystokinin; gastrin inhibitory peptides; calmodulin; gastric-releasing peptides; motilin; vasoactive intestinal peptides; atrial natriuretic peptides (ANPs); B-type natriuretic peptides (BNPs); C-type natriuretic peptides (CNPs); neurokinin A; neuromedin; renin; endothelin; sarafotoxin peptide; carsomorphin peptide; dermorphin; dynorphin; endorphin; enkepalin; T cell factors; tumor necrosis factor; tumor necrosis factor receptors; urokinase receptors; tumor inhibitory factors; collagenase inhibitors; thymopoietin; thymulin; thymopentin; thymosin; thymic humoral factor; adrenomedullin; allatostatin; amyloid β-protein fragments; antibacterial peptides; antioxidant peptides; bombesin; osteocalcin; CART peptides; E-selectin; ICAM-1; VCAM-1; leucokine; kringle-5; laminin; inhibin; galanin; fibronectin; pancreastatin; fuzeon; interferon receptors; G protein-coupled receptors; interleukin receptors; enzymes; interleukin-binding proteins; cytokine-binding proteins; macrophage-activating factors; macrophage peptides; B cell factor; protein A; allergy inhibitors; cell necrosis glycoprotein; immunotoxin; lymphotoxin; tumor inhibitory factors; metastasis growth factors; α-1-antitrypsin; albumin; α-lactalbumin; apolipoprotein-E; erythropoietin; highly glycosylated erythropoietin; angiopoietins; hemoglobin; thrombin; thrombin receptor-activating peptides; thrombomodulin; blood factors VII, VIIa, VIII, IX, and XIII; plasminogen-activating factors; fibrin-binding peptides; urokinase; streptokinase; hirudin; protein C; C-reactive protein; renin inhibitors; superoxide dismutase; platelet-derived growth factors; epidermal growth factors; epithelial cell growth factors; angiostatin; angiotensin; osteogenic growth factors; osteogenesis-promoting proteins; atriopeptin; cartilage-inducing factors; elcatonin; connective tissue-activating factors; tissue factor pathway inhibitors; luteinizing hormone-releasing hormone; nerve growth factors; relaxin; somatomedin; insulin-like growth factor; adrenocortical hormone; pancreatic polypeptides; gastrin-releasing peptides; corticotropin-releasing factor; thyroid-stimulating hormone; autotoxin; lactoferrin; myostatin; cell surface antigens; virus-derived vaccine antigens; monoclonal antibody; polyclonal antibody; antibody fragments; erythropoietic growth factors; leukopoietin; amylin; and analogs thereof, but is not particularly limited thereto.

Still another aspect of the present invention provides a method for preparing a conjugate, in which a physiologically active polypeptide and a carrier protein are linked by a polyethylene glycol compound.

The physiologically active polypeptide and polyethylene glycol compound are the same as explained above.

Specifically, the method may include:

(a) reacting the polyethylene glycol compound with any one of a physiologically active polypeptide or carrier protein, thereby preparing a polyethylene glycol compound, wherein the physiologically active polypeptide or carrier protein is attached to one end of the polyethylene glycol compound and the other end of the polyethylene glycol compound has a reactive end group; and (b) reacting the polyethylene glycol compound prepared in step (a) above, wherein the physiologically active polypeptide or carrier protein is attached to one end of the polyethylene glycol compound and the other end of the polyethylene glycol compound has a reactive end group, with the other one of the physiologically active polypeptide or carrier protein, so as to link the carrier protein or physiologically active polypeptide to the reactive end group of the polyethylene glycol compound, thereby preparing a conjugate in which the physiologically active polypeptide and the carrier protein are linked by a polyethylene glycol compound.

More specifically, the method may include:

(a) reacting the polyethylene glycol compound with a physiologically active polypeptide, thereby preparing a polyethylene glycol compound, wherein the physiologically active polypeptide is attached to one end of the polyethylene glycol compound and the other end of the polyethylene glycol compound has a reactive end group; and (b) reacting the polyethylene glycol compound prepared in step (a) above, wherein the physiologically active polypeptide is attached to one end of the polyethylene glycol compound and the other end of the polyethylene glycol compound has a reactive end group, with a carrier protein, so as to link the carrier protein to the reactive end group of the polyethylene glycol compound.

Specifically, the polyethylene glycol compound in step (a) may have a structure of Formula 1 below.

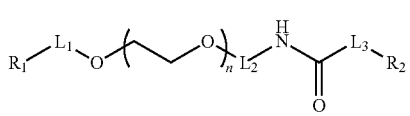

[Formula 1]

In Formula 1 above, $R_1$ is aldehyde;

each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In the above method, the reaction between the polyethylene glycol compound and the physiologically active polypeptide may include a reaction between the $R_2$ of the polyethylene glycol compound with the thiol group located at the cysteine residue of the physiologically active polypeptide, and the reaction between the polyethylene glycol compound and the carrier protein may include a reaction between the aldehyde end group of the polyethylene glycol compound and the amine group of the carrier protein, although the reactions are not particularly limited thereto.

Specifically, in the above method, step (a) may be reacting $R_2$ of the polyethylene glycol compound having the structure of Formula 1 above with the thiol group located at the cysteine residue of the physiologically active polypeptide, whereas step (b) may be reacting the aldehyde end group of the polyethylene glycol compound with the amine group of the carrier protein.

The reaction between the polyethylene glycol compound and the physiologically active polypeptide or the carrier protein may be appropriately determined by one of ordinary skill in the art, in consideration of the characteristics of the reactive groups of the polyethylene glycol compound and the characteristics of the reactive groups of the physiologically active polypeptide or the carrier protein, to which the polyethylene glycol compound is to be linked.

For example, the PEGylation reaction may be performed in the presence of an appropriate buffer such as citrate buffer or HEPES or an organic solvent such as $C_{1-6}$ alcohol, but the buffer and the solvent are not particularly limited thereto.

Additionally, the aldehyde reactive group selectively reacts with the amino terminal in a low pH condition, and may form a covalent bond with a lysine residue in a high pH condition, (e.g., pH 9.0).

Meanwhile, the carrier protein may be a material which is linked to the physiologically active polypeptide by the polyethylene glycol compound for the purpose of increasing the in vivo half-life of the physiologically active polypeptide.

The carrier protein may be albumin and a fragment thereof, a polymer of a repeating unit of a particular amino acid sequence, antibody, an antibody fragment, an FcRn-binding material, fibronectin, transferrin, saccharide, or elastin, and the FcRn-binding material may be an immunoglobulin Fc fragment, but is not particularly limited thereto.

In a specific embodiment, the end aldehyde group of the polyethylene glycol compound may be one which reacts with the amine group of an immunoglobulin Fc fragment, and specifically the amine group of the N-terminus, but is not particularly limited thereto.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of a protein conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in a specific embodiment, the immunoglobulin Fc region may be in a dimeric form and one molecule of X may be covalently linked to one Fc region in a dimer form, where the immunoglobulin Fc and X may be linked to each other by a polyethylene glycol compound. Meanwhile, it is also possible that two molecules of X are symmetrically linked to one Fc region in a dimeric form, where the immunoglobulin Fc and X may be linked to each other by a polyethylene glycol compound. However, the linkage is not limited thereto.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be important in the conjugation of an immunoglobulin Fc, may be used as suitable sites for modification.

Additionally, other various derivatives are possible, including one that has a deletion of a region capable of forming a disulfide bond, or a deletion of some amino acid residues at the N-terminus of native Fc or an addition of a methionine residue at the N-terminus of native Fc, etc. Furthermore, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not entirely alter the activities of molecules, are known in the art (H. Neurath, R. L. Hill, *The Proteins*, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. Depending on the cases, the Fc region may be modified by phosphorylation, sulfation, acrylation, glycosylation, methylation, farnesylation, acetylation, amidation, etc.

The above-described Fc derivatives show a biological activity identical to that of the Fc region of the present invention and they may have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinants or derivatives thereof obtained from transformed animal cells or microorganisms. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size-exclusion chromatography, etc. In a more specific embodiment, a human-derived Fc region is a recombinant immunoglobulin Fc region obtained from a microorganism.

Additionally, the immunoglobulin Fc region may be in the form of a natural glycan, increased or decreased glycan compared to the natural type, or in a deglycosylated form. The increase, decrease, or removal of the immunoglobulin Fc glycan may be achieved by conventional methods such as a chemical method, enzymatic method, and genetic engineering method using a microorganism. The immunoglobulin Fc region obtained by removal of a glycan from the Fc region shows a significant decrease in binding affinity to the C1q part and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier.

As used herein, the term "deglycosylation" refers to enzymatically removing sugar moieties from an Fc region, and the term "aglycosylation" refers to an unglycosylated Fc region produced in prokaryotes, in a more specific embodiment, *E. coli*.

Meanwhile, the immunoglobulin Fc region may be derived from humans or other animals including cows, goats, pigs, mice, rabbits, hamsters, rats, and guinea pigs. In a more specific embodiment, it is of human origin.

Additionally, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Additionally, the above method may further include purifying a conjugate, in which a physiologically active polypeptide and a carrier protein are linked by a polyethylene glycol compound.

For the purification, any known method in the art may be used without limitation, and specifically chromatography may be used, but the purification method is not particularly limited thereto.

Still another aspect of the present invention provides a physiologically active polypeptide, to which the polyethylene glycol compound is attached.

The polyethylene glycol compound and physiologically active polypeptide are the same as explained above.

In a specific embodiment, the physiologically active polypeptide may be one which includes the structure represented by any of Formulas 15 to 17:

$R_1$-$L_1$-O—(CH$_2$CH$_2$O)$_n$-$L_2$-NH(CO)-$L_3$-S—S—X [Formula 15]

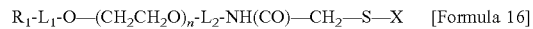

$R_1$-$L_1$-O—(CH$_2$CH$_2$O)$_n$-$L_2$-NH(CO)—CH$_2$—S—X [Formula 16]

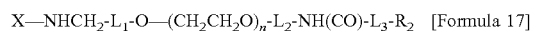

X—NHCH$_2$-$L_1$-O—(CH$_2$CH$_2$O)$_n$-$L_2$-NH(CO)-$L_3$-$R_2$ [Formula 17]

wherein, in Formulas 15 to 17, $R_1$ is selected from 2,5-dioxopyrrolidinyl, 2,5-dioxopyrrolyl, aldehyde, maleimide, C$_{6-20}$ aryl disulfide, C$_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched C$_{1-6}$ alkylene;

n is an integer of 10 to 2400;

$R_2$ is ortho-pyridyl disulfide (OPSS), thiol, or halogen; and

X corresponds to a physiologically active polypeptide moiety.

All of the explanations provided previously will apply to the specific features and combinations of the variables described above.

The "—S—S—X" in Formula 15 above may be a structure formed by the reaction between the thiol group located at X and the ortho-pyridyl disulfide or thiol group; and the "—CH$_2$—S—X" in Formula 16 may be a structure formed by the reaction between the thiol group located at X and a halogen, and specifically iodoacetamide (IA); and the "X—NHCH$_2$—" in Formula 16 may be a structure formed by the reaction between the amine group located at X and an aldehyde group through reductive alkylation, but the structures are not particularly limited thereto.

Still another aspect of the present invention provides a conjugate, in which each of a physiologically active polypeptide and a carrier protein is independently attached to reactive groups at both ends of the polyethylene glycol compound.

The polyethylene glycol compound, physiologically active polypeptide, and carrier protein are the same as explained above.

In a specific embodiment, the conjugate has a structure represented by Formula 18 or 19 below:

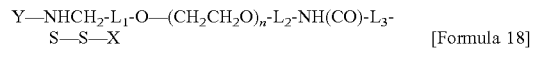

Y—NHCH$_2$-$L_1$-O—(CH$_2$CH$_2$O)$_n$-$L_2$-NH(CO)-$L_3$-S—S—X [Formula 18]

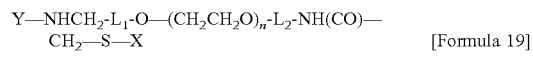

Y—NHCH$_2$-$L_1$-O—(CH$_2$CH$_2$O)$_n$-$L_2$-NH(CO)—CH$_2$—S—X [Formula 19]

wherein, in Formulas 18 and 19 above,
each of $L_1$ to $L_3$ is independently a linear or branched $C_{1-6}$ alkylene;
n is an integer of 10 to 2400;
X is a physiologically active polypeptide moiety; and
Y is a carrier protein moiety.

Still another aspect of the present invention provides a method for preparing the polyethylene glycol compound.

The polyethylene glycol compound is the same as explained above.

Specifically, the method may include:
(a) introducing $R_1$ selected from the group consisting of 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof, to one end of a polyethylene glycol; and
(b) introducing the structure of —NH(CO)$L_3$-$R_2$ to the other end of the polyethylene glycol, wherein $R_2$ is ortho-pyridyl disulfide (OPSS), thiol, or halogen.

As a non-limiting method, the method may include:
a first step for preparing a compound represented by Formula 21 below from a compound represented by Formula 20 below;
a second step for preparing a compound represented by Formula 22 below from a compound represented by Formula 21 below; and
a third step for converting the diethoxy methyl at an end of a compound represented by Formula 22 below into aldehyde by treating the compound represented by Formula 22 with an acid solution:

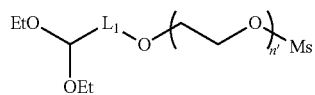
[Formula 20]

wherein, in Formula 20 above, n' is n or n+1; and

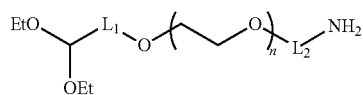
[Formula 21]

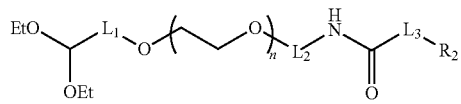
[Formula 22]

wherein $L_1$, $L_2$, $L_3$, n, and $R_2$ are the same as described above.

In a case where a polyethylene glycol compound, where $L_2$ is 2 as in linker #5 (Formula 7), n' may be n+1.

In the above method, the compound represented by Formula 20 of the first step may be one which is prepared by reacting the compound represented by Formula 23 with methanesulfonyl chloride:

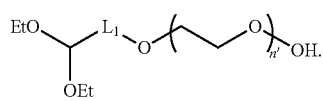
[Formula 23]

In a case where a polyethylene glycol compound, where $L_2$ is 2 as in linker #5 (Formula 7), the first step may be performed by reacting the compound represented by Formula 20 with an aqueous ammonia solution and ammonium chloride.

Meanwhile, in cases where a polyethylene glycol compound, where $L_2$ is 3 or higher as in linkers #7 to #9 (Formulas 9 to 11), etc., the method may include:
step 1-1, which is to react a compound represented by Formula 20 with hydroxyalkyl tetrahydropyranyl ether, thereby preparing a compound represented by Formula 24;
step 1-2, which is to react a compound represented by Formula 24 with p-toluenesulfonic acid, thereby substituting the tetrahydropyranyloxy group at an end thereof with a hydroxy group;
step 1-3, which is to react the compound obtained in step 1-2 with methanesulfonyl chloride, thereby substituting the hydroxy group with a methanesulfonic acid group; and
step 1-4, which is to react the compound obtained in step 1-3 with an aqueous ammonia solution and ammonium chloride:

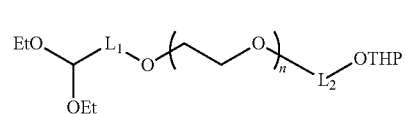
[Formula 24]

wherein step 1-1 may be performed in the presence of potassium t-pentoxide.

Additionally, in a case where OPSS is introduced as a reactive end group, the second step may be performed by reacting a compound represented by Formula 21 with a compound represented by Formula 25.

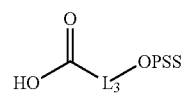
[Formula 25]

Meanwhile, in a case where —I or —SH is introduced as a reactive end group, the second step may be performed by reacting a compound represented by Formula 21 with chloro ($C_2$ to $C_7$ alkanoyl) chloride, thereby synthesizing a compound comprising a chloro group at an end thereof, which is represented by Formula 26 below, as an intermediate product; and reacting the compound represented by Formula 26 with a halogen metal salt in the presence or absence of hydrogen sulfide, thereby converting the chloro group into thiol or halogen.

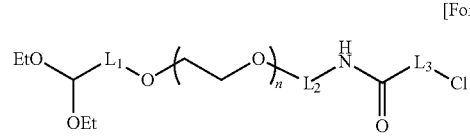
[Formula 26]

Still another aspect of the present invention provides a use of the polyethylene glycol compound for linking a carrier, which is capable of increasing an in vivo half-life of a physiologically active polypeptide, to a physiologically active polypeptide.

The physiologically active polypeptide, carrier, and polyethylene glycol compound are the same as explained above.

Still another aspect of the present invention provides a composition containing a physiologically active polypeptide to which the polyethylene glycol compound is attached or the conjugate.

The physiologically active polypeptide, conjugate, and polyethylene glycol compound are the same as explained above.

The composition may be a pharmaceutically acceptable composition and may contain a pharmaceutically acceptable carrier. The pharmaceutically acceptable carrier may include, for oral administration, a binder, a lubricant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined for use; and for topical administrations, a base, an excipient, a lubricant, a preserving agent, etc. The formulation type of the pharmaceutical composition of the present invention may be prepared variously by combining with a pharmaceutically acceptable carrier described above. For example, for oral administration, the composition may be formulated into tablets, troches, capsules, elixirs, suspensions, syrups, wafers, etc. For injections, the composition may be formulated into unit-dose ampoules or multi-dose forms. The composition may also be formulated into solutions, suspensions, tablets, pills, capsules, sustained-release formulations, etc.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preserving agent, etc.

Still another aspect of the present invention provides a polyethylene glycol compound linker for linking a carrier, which is capable of increasing an in vivo half-life of a physiologically active polypeptide, to a physiologically active polypeptide.

The physiologically active polypeptide, carrier, and polyethylene glycol compound are the same as explained above.

The compounds of the present invention may be synthesized by a series of reactions represented by Reaction Scheme below. However, the Formulas below are merely illustrative examples of the methods for preparing the compounds of the present invention, and thus the compounds of the present invention should not be limited by these methods and the preparation of these compounds may be prepared by a method known in the art or may be performed after an appropriate modification thereof.

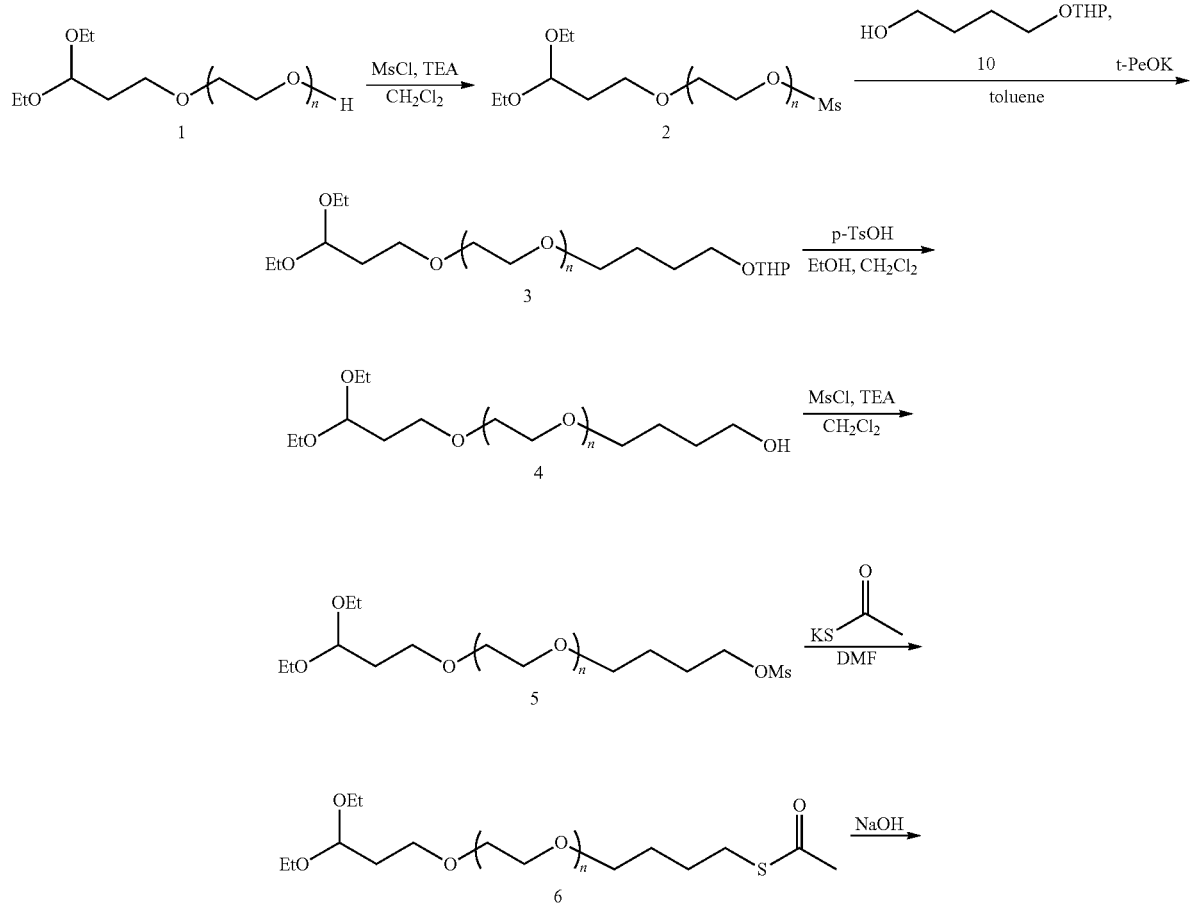

[Reaction Scheme]

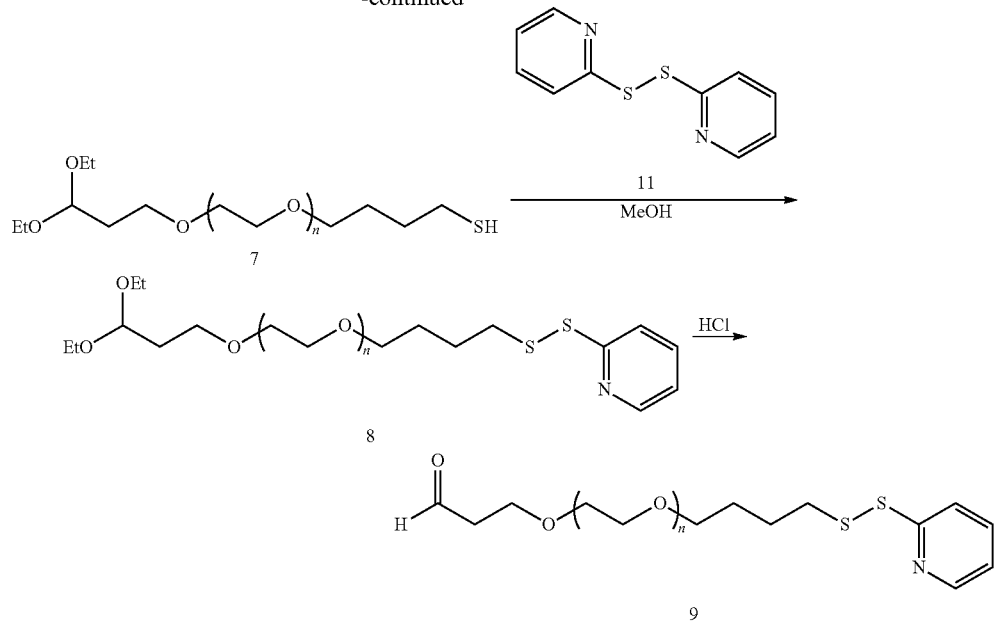

<Reaction Example 1> Preparation of Compound No. 2

Compound No. 1 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the resulting organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 2.

<Reaction Example 2> Preparation of Compound No. 3

Toluene and Compound No. 10 are added into a reaction container. After adding potassium t-pentoxide thereto, the mixture is heated to about 50° C. and stirred at 50° C. for 1 hour (an activation solution). Compound No. 2 and toluene are added into another container. The activation solution is cooled to room temperature and added dropwise to the mixed solution at 30° C. for 1 hour. After stirring at 30° C. for 3 hours, water is added to the reaction solution and the extraction is performed. After separation of layers, dichloromethane is added to the resulting aqueous layer and the mixture is extracted. Dichloromethane is again added to the aqueous layer and the mixture is extracted once more. The resulting organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 3.

<Reaction Example 3> Preparation of Compound No. 4

Compound No. 3, ethanol, and dichloromethane are added into a reaction container. p-Toluene sulfonic acid (p-TsOH) is added thereto and stirred at room temperature for 20 hours. Sodium hydroxide is added thereto and the solvent is concentrated under reduced pressure. Dichloromethane and water are added thereto and stirred for 5 minutes. The organic layer is extracted therefrom and washed with water. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 4.

<Reaction Example 4> Preparation of Compound No. 5

Compound No. 4 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the organic layer, dichloromethane is again added to the resulting aqueous layer and extracted once more. The organic layers are combined, washed with distilled water (60 mL), dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 5.

<Reaction Example 5> Preparation of Compound No. 6

Dimethylformamide and Compound No. 5 are added into a reaction container. After heating the mixture to about 30° C., potassium thioacetate is added thereto and stirred at 30° C. for 5 hours. After cooling the mixture to room temperature, dichloromethane and water are added thereto and extracted. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 6.

<Reaction Example 6> Preparation of Compound No. 7

Water and Compound No. 6 are added into a container. The reaction solution is adjusted to pH 14 by adding a 0.1 M sodium hydroxide solution dropwise thereto. After stirring the mixture at room temperature for 12 hours, the mixture is adjusted to pH 6 to 7 using a 1 N HCl solution. After neutralization, dichloromethane is added thereto and the mixture is extracted. After separation of layers, the resulting aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 7.

<Reaction Example 7> Preparation of Compound No. 8

Compound No. 7 and methanol are added into a reaction container. Compound No. 11 is added dropwise thereto and stirred at room temperature for 3 days. The reaction solvent is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 8.

<Reaction Example 8> Preparation of Compound No. 9 [Linker #1]

Compound No. 8 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The mixture is adjusted to pH 6 using 5% sodium bicarbonate. Dichloromethane is added thereto and extraction is performed. Sodium sulfate is added to the resulting organic layer and stirred for 30 minutes. The mixed solution is filtered and the filtrate is concentrated under reduced pressure. The concentrate is dissolved by adding dichloromethane (1 mL) thereto and methyl t-butyl ether is added dropwise thereto for 20 minutes. The thus-produced crystals are filtered, washed with methyl t-butyl ether, and dried under nitrogen at room temperature to obtain the target compound, Compound No. 9.

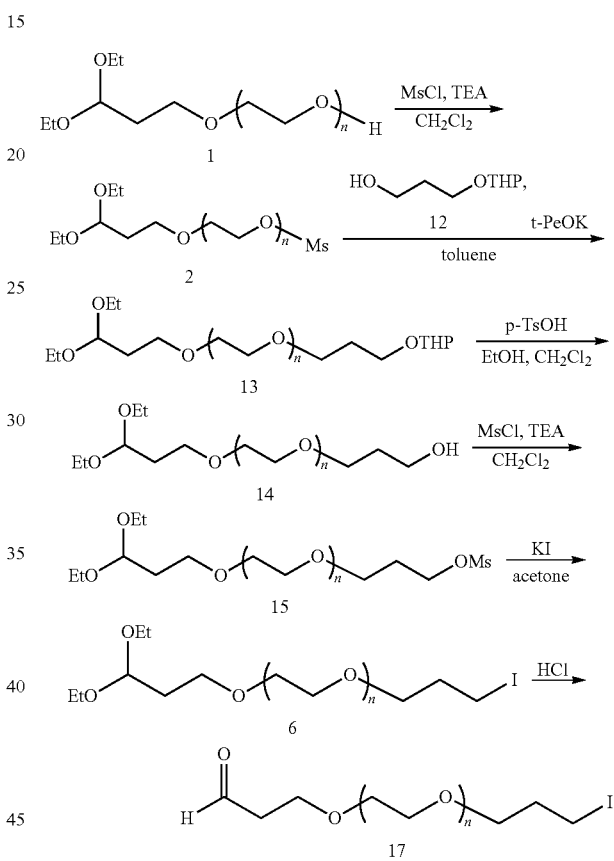

<Reaction Example 9> Preparation of Compound No. 13

Toluene and Compound No. 12 are added into a reaction container. After adding potassium t-pentoxide thereto, the mixture is heated to about 50° C. and stirred at 50° C. for 1 hour (an activation solution). Compound No. 2 and toluene are added into another container. The activation solution is cooled to room temperature and added dropwise to the mixed solution at 30° C. for 1 hour. After stirring the mixture at 30° C. for 3 hours, water is added to the reaction solution and extraction is performed. After separation of layers, dichloromethane is added to the aqueous layer and extracted. Dichloromethane is again added to the aqueous layer and the mixture is extracted once more. The resulting organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 13.

<Reaction Example 10> Preparation of Compound No. 14

Compound No. 13, ethanol, and dichloromethane are added into a reaction container. p-Toluene sulfonic acid (p-TsOH) is added thereto and stirred at room temperature for 20 hours. Sodium hydroxide is added thereto and the solvent is concentrated under reduced pressure. Dichloromethane and water are added thereto and stirred for 5 minutes. The organic layer is extracted therefrom and washed with water. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. minutes. The thus-produced crystals are filtered, washed with methyl t-butyl ether, and dried under nitrogen at room temperature to obtain the target compound, Compound No. 14.

<Reaction Example 11> Preparation of Compound No. 15

Compound No. 14 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 15.

<Reaction Example 12> Preparation of Compound No. 16

Acetone and Compound No. 15 are added into a reaction container. After heating the mixture to 30° C., potassium iodide is added thereto, and heated to about 50° C. and stirred at 50° C. for 15 hours. The reaction solution is concentrated under reduced pressure and washed with dichloromethane and water. After separation of layers, the resulting organic layer is washed again with water. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether (30 mL) is added dropwise thereto for 5 minutes. The thus-produced crystals are filtered, washed with methyl t-butyl ether, and dried under nitrogen at room temperature to obtain the target compound, Compound No. 16.

<Reaction Example 13> Preparation of Compound No. 17 [Linker #2]

Compound No. 16 and water are added into a container. The reaction solution is adjusted to pH 1.0 by adding a 1 N HCl solution dropwise thereto. After stirring at room temperature for 1 hour, the reaction solution is adjusted to pH 6 to 7 using a 5% sodium bicarbonate solution. After neutralization, dichloromethane is added thereto and the extraction is performed. After separation of layers, the aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 17.

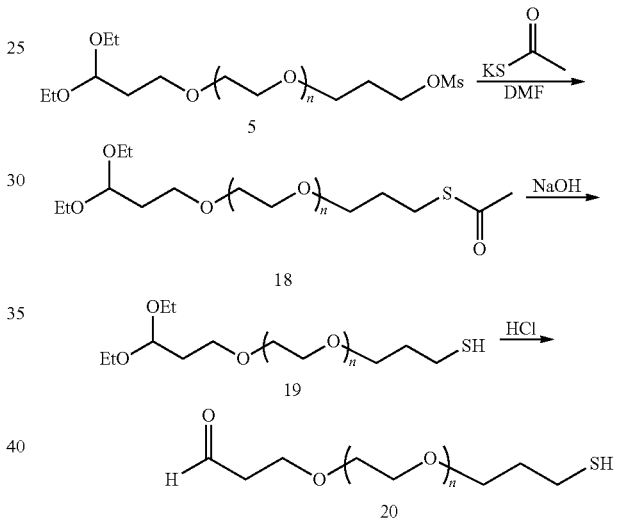

<Reaction Example 14> Preparation of Compound No. 18

Dimethylformamide and Compound No. 15 are added into a container. After heating the mixture to about 30° C., potassium thioacetate is added thereto and stirred at 30° C. for 5 hours. After cooling the mixture to room temperature, dichloromethane and water are added thereto and the extraction is performed. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 18.

<Reaction Example 15> Preparation of Compound No. 19

Compound No. 18 and water are added into a reaction container. The reaction solution is adjusted to pH 14 by adding a 0.1 M NaOH solution dropwise thereto. After stirring at room temperature for 12 hours, the reaction solution is adjusted to pH 6 to 7 using a 1 N HCl solution. After neutralization, dichloromethane is added thereto and the extraction is performed. After separation of layers, the aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 19.

<Reaction Example 16> Preparation of Compound No. 20 [Linker #3]

Compound No. 19 and water are added into a reaction container. The reaction solution is adjusted to pH 1.0 by adding a 1 N HCl solution dropwise thereto. After stirring at room temperature for 1 hour, the reaction solution is adjusted to pH 6 to 7 using a 5% sodium bicarbonate solution. After neutralization, dichloromethane is added thereto and the extraction is performed. After separation of layers, the aqueous layer is re-extracted with dichloromethane (5 mL). The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 20.

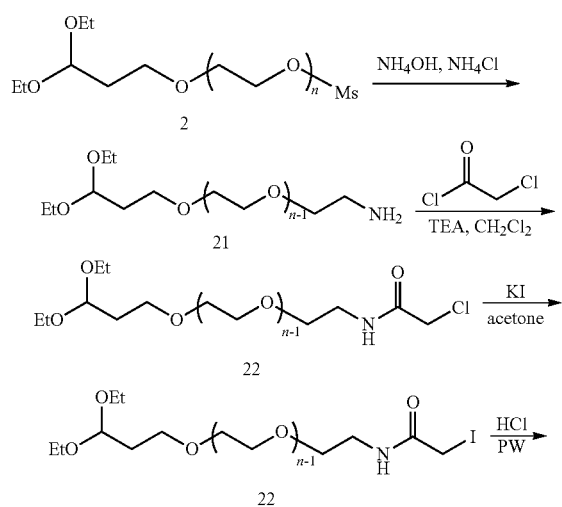

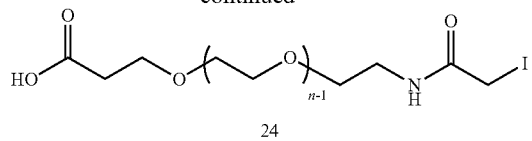

<Reaction Example 17> Preparation of Compound No. 21

An aqueous ammonia solution and ammonium chloride are added into a reaction container. Compound No. 5 is added thereto and stirred at room temperature for 4 days. Dichloromethane is added thereto and stirred for 5 minutes. After extracting an organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 21.

<Reaction Example 18> Preparation of Compound No. 22

Compound No. 21 and dichloromethane are added into a reaction container. Triethylamine and chloroacetyl chloride are added dropwise thereto and stirred at room temperature for 16 hours. Upon completion of the reaction, the reaction solution is washed with water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 22.

<Reaction Example 19> Preparation of Compound No. 23

Compound No. 22 and acetone are added into a reaction container. KI is added thereto and stirred at 55° C. for 6 hours. After cooling the reaction solution to room temperature, the reaction solvent is concentrated under reduced pressure. Then, dichloromethane and water are added thereto and stirred for 5 minutes. After extracting the organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 23.

<Reaction Example 20> Preparation of Compound No. 24 [Linker #5]

Compound No. 23 and distilled water are added into a reaction container. The reaction solution is adjusted to pH 1.0 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer and stirred for 30 minutes. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 24.

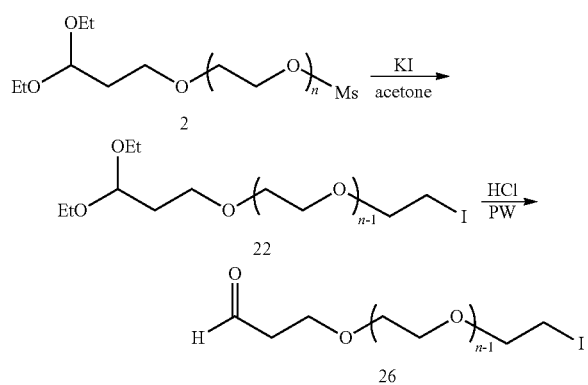

<Reaction Example 21> Preparation of Compound No. 25

Compound No. 5 and acetone are added into a reaction container. KI is added thereto and stirred at 55° C. for 20 hours. After cooling the reaction solution to room temperature, the reaction solvent is concentrated under reduced pressure. Then, dichloromethane and water are added thereto and stirred for 5 minutes. After extracting the organic layer, dichloromethane is again added to the resulting aqueous layer and extracted once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 25.

<Reaction Example 22> Preparation of Compound No. 26 [Linker #11]

Compound No. 25 and distilled water are added into a reaction container. The reaction solution is adjusted to pH 1.0 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer and stirred for 30 minutes. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 26.

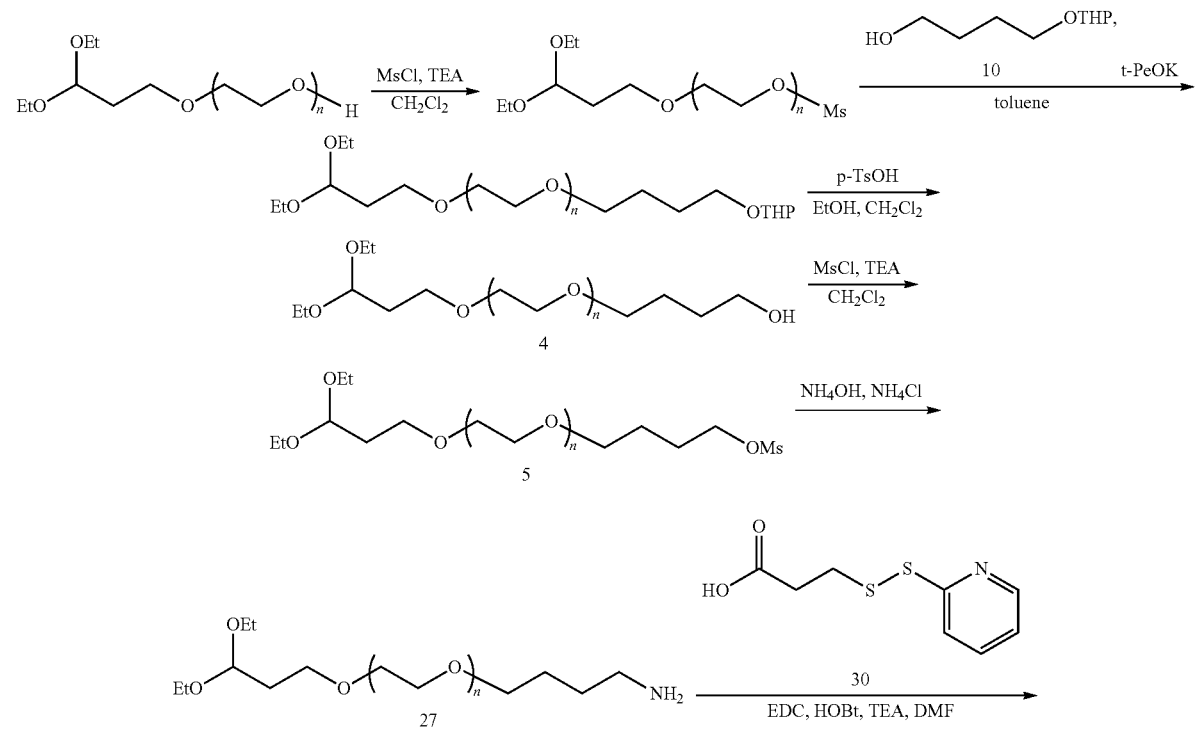

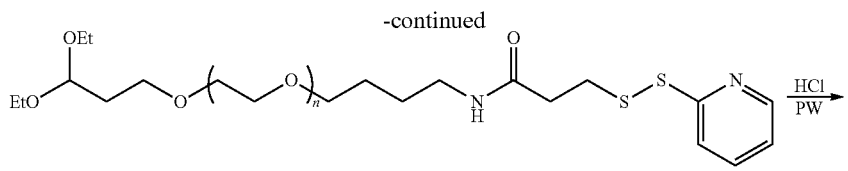

28

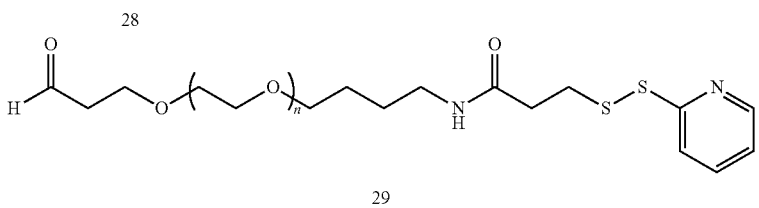

29

<Reaction Example 23> Preparation of Compound No. 27

An aqueous ammonia solution and ammonium chloride are added into a reaction container. Compound No. 5 is added thereto and stirred at room temperature for 4 days. Dichloromethane is added thereto and the organic layer is extracted therefrom and dichloromethane is again added and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 27.

<Reaction Example 24> Preparation of Compound No. 28

Compound No. 27, Compound No. 30, 1-ethyl-3-(3-dimethylaminopropyl)carbodiimide (EDC), hydroxybenzotriazole (HOBt), triethylamine, and dimethylformamide are added into a reaction container, and stirred at room temperature for 16 hours. Dichloromethane and water are added thereto and the extraction is performed. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 28.

<Reaction Example 25> Preparation of Compound No. 29 [Linker #7]

Compound No. 28 and distilled water are added into a reaction container. The reaction solution is adjusted to pH 1.0 using a 1 N HCl solution and stirred at room temperature for 1 hour. Upon completion of the reaction, water and dichloromethane are added thereto and stirred. The resultant is adjusted to pH 6 using 5% sodium bicarbonate. The resultant is extracted by adding dichloromethane thereto and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 29.

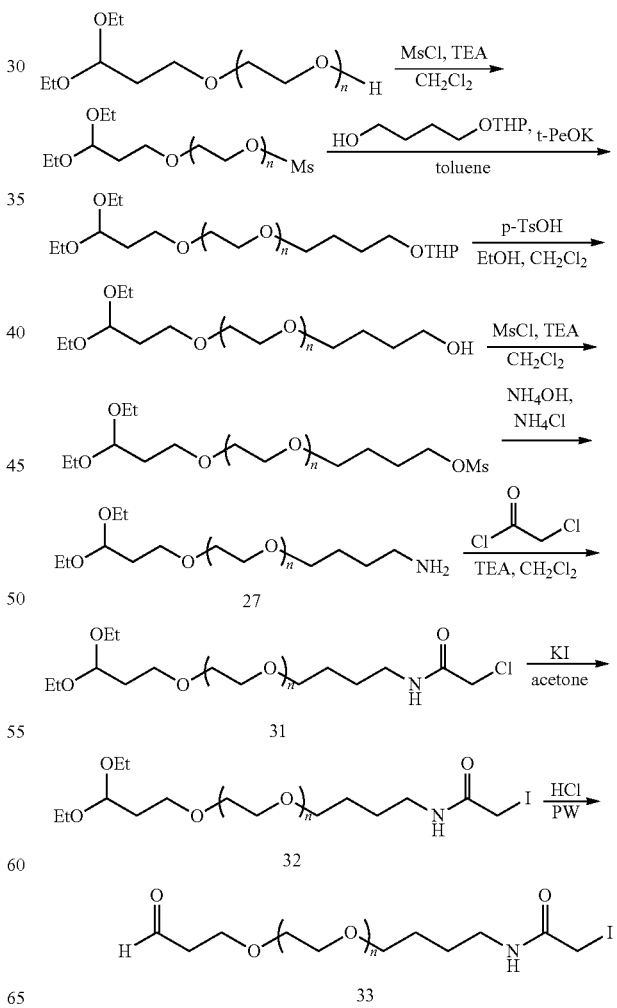

\<Reaction Example 26\> Preparation of Compound No. 31

Compound No. 27 and dichloromethane are added into a reaction container. Triethylamine and chloroacetyl chloride are added dropwise thereto and stirred at room temperature for 16 hours. Upon completion of the reaction, the reaction solution is washed with water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 31.

\<Reaction Example 27\> Preparation of Compound No. 32

Compound No. 31 and acetone are added into a reaction container. KI is added thereto and stirred at 55° C. for 6 hours. After cooling the reaction solution to room temperature, the reaction solvent is concentrated under reduced pressure. Then, dichloromethane and water are added thereto. After extracting the organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 32.

\<Reaction Example 28\> Preparation of Compound No. 33 [Linker #8]

Compound No. 32 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 33.

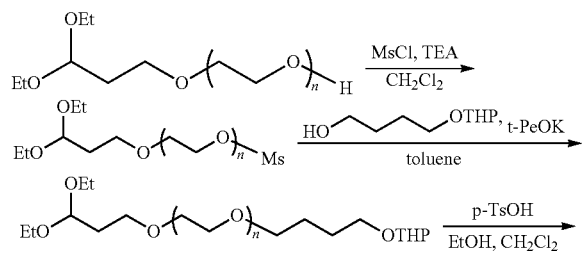

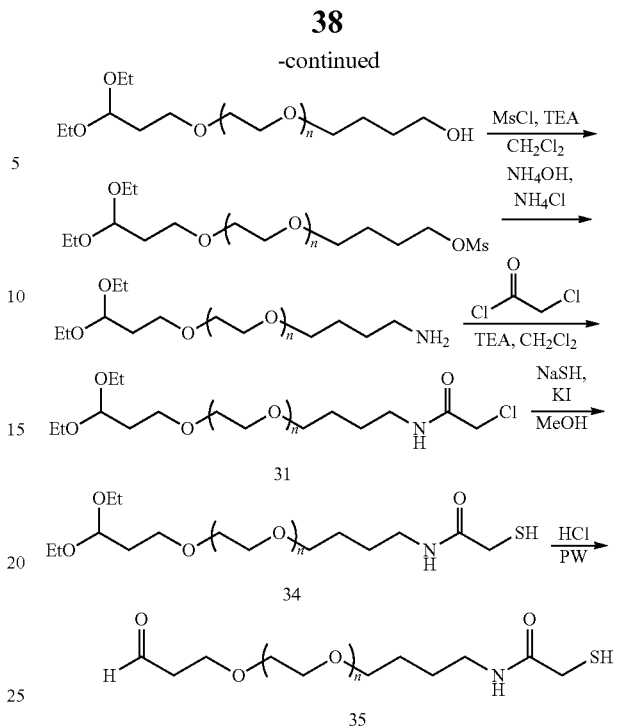

\<Reaction Example 29\> Preparation of Compound No. 34

Compound No. 31 and methanol are added into a reaction container. KI and NaSH are added thereto and stirred at room temperature for 6 hours. After cooling the reaction solution to room temperature, the reaction solvent is concentrated under reduced pressure. Then, dichloromethane and water are added thereto. After extracting an organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 34.

\<Reaction Example 30\> Preparation of Compound No. 35 [Linker #9]

Compound No. 34 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 35.

Hereinafter, the present invention will be described in more detail with reference to the following embodiments, etc., to aid in the understanding of the present invention.

However, these embodiments can be modified in various other forms and the scope of the present invention should not be interpreted to be limited by these embodiments.

The embodiments are provided to more fully illustrate the present invention to those who have an average knowledge in the art.

Example 1: Preparation of Polyethylene Glycol Derivatives

The present inventors have prepared polyethylene glycol derivatives in which desired reactive groups are introduced at both ends thereof. The methods for preparing the derivatives are described in Reaction Examples 1 to 25.

Representatively, heterofunctional PEG compounds, in which a propionaldehyde group is added to one end of the polyethylene glycol backbone while ortho-pyridyl disulfide (OPSS), iodoacetamide (IA), an iodine group, or sulfhydryl group (SH—) is added to the other end, were prepared [FIG. 1].

The purity of each of the thus-prepared PEG compounds was analyzed by NMR and reversed phase chromatography (RPC), respectively.

The details of the representative polyethylene glycol derivatives are as follows.

(1) Linker #1: pALD-PEG-Ortho-Pyridyl Disulfide

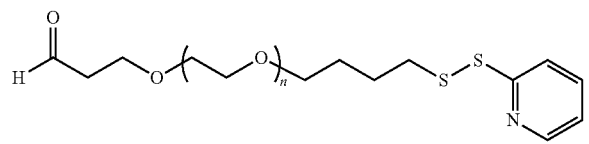

[Formula 3]

Here, n is an integer of 200 to 300.

The molecular weight of the thus-prepared polyethylene glycol linker was about 10 kDa, and its structure was confirmed by NMR analysis. The purity was confirmed to be about 80% by RPC analysis.

$^1$H-NMR (CDCl$_3$, 400 MHz): δ 9.79 (t, 1H, J=2.0 Hz), 8.50 (d, 1H, J=5.6 Hz), 7.71-7.64 (m, 2H), 7.09-6.70 (m, 1H), 3.87-3.40 (m, 908H), 2.82 (t, 2H, J=5.6 Hz), 2.68 (t, 2H, J=2.0 Hz), 1.86-1.66 (m, 4H)

(2) Linker #2: pALD-PEG-Iodide

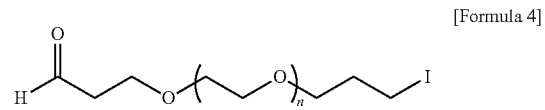

[Formula 4]

Here, n is an integer of 200 to 300.

The molecular weight of the thus-prepared polyethylene glycol linker was about 10 kDa, and its structure was confirmed by NMR analysis. The purity was confirmed to be about 87% by RPC analysis.

$^1$H-NMR (CDCl$_3$, 400 MHz): δ 9.81 (s, 1H), 3.84-3.47 (m, 910H), 3.29 (t, 2H, J=6.8 Hz), 2.71-2.69 (m, 2H), 2.10-2.06 (m, 2H)

(3) Linker #3: pALD-PEG-Sulfhydryl Group

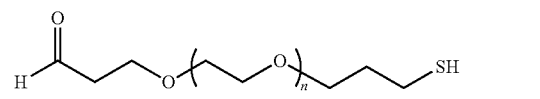

[Formula 5]

Here, n is an integer of 200 to 300.

The molecular weight of the thus-prepared polyethylene glycol linker was about 10 kDa, and its structure was confirmed by NMR analysis. The purity was confirmed to be about 76% by RPC analysis.

$^1$H-NMR (CDCl$_3$, 400 MHz): δ 9.79 (s, 1H), 3.82-3.45 (m, 910H), 2.74 (t, 2H, J=6.8 Hz), 2.69-2.67 (m, 2H), 1.99-1.95 (m, 2H)

(4) Linker #5: pALD-PEG-Iodide

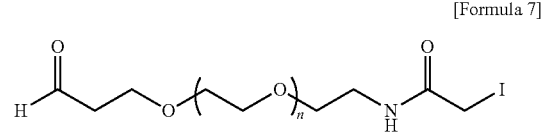

[Formula 7]

Here, n is an integer of 200 to 300.

The molecular weight of the thus-prepared polyethylene glycol linker was about 10 kDa, and its structure was confirmed by NMR analysis. The purity was confirmed to be about 88% by RPC analysis.

$^1$H-NMR (CDCl$_3$, 400 MHz): δ 9.78 (t, 1H, J=1.6 Hz), 3.82-3.41 (m, 912H), 2.67 (t, 2H, J=2.0 Hz)

(5) Linker #7: pALD-PEG-Ortho-Pyridyl Disulfide

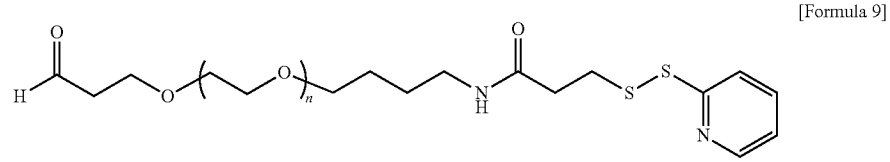

[Formula 9]

Here, n is an integer of 200 to 300.

The molecular weight of the thus-prepared polyethylene glycol linker was about 10 kDa, and the purity was confirmed to be about 81% by RPC analysis.

(6) Linker #8: pALD-PEG-Iodide

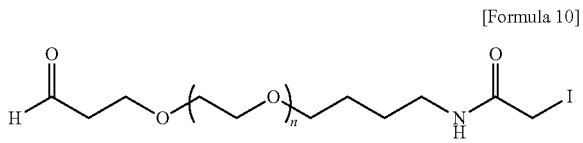

[Formula 10]

Here, n is an integer of 200 to 300.

The molecular weight of the thus-prepared polyethylene glycol linker was about 10 kDa, and its structure was confirmed by NMR analysis. The purity was confirmed to be about 78% by RPC analysis.

$^1$H-NMR (CDCl$_3$, 400 MHz): δ 9.78 (s, 1H), 3.82-3.41 (m, 912H), 2.70 (t, 2H, J=2.0 Hz), 1.44-1.24 (m, 4H)

(7) Linker #9: pALD-PEG-Sulfhydryl Group

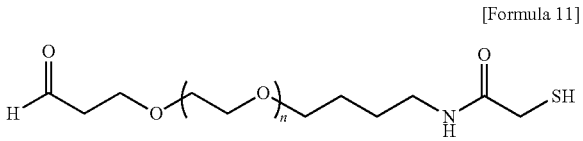

[Formula 11]

Here, n is an integer of 200 to 300.

The molecular weight of the thus-prepared polyethylene glycol linker was about 10 kDa, and the purity was confirmed to be about 76% by RPC analysis.

(8) Linker #11: pALD-PEG-Iodide (Comparative Example)

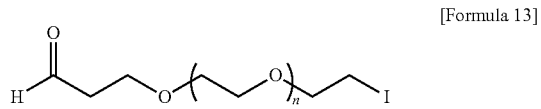

[Formula 13]

Here, n is an integer of 200 to 300.

The molecular weight of the thus-prepared polyethylene glycol linker was about 10 kDa, and its structure was confirmed by NMR analysis. The purity was confirmed to be about 89% RPC analysis.

$^1$H-NMR (CDCl$_3$, 400 MHz): δ 9.79 (t, 1H, J=2.0 Hz), 3.82-3.41 (m, 908H), 3.29-3.22 (m, 2H), 2.69 (t, 2H, J=2.0 Hz)

Example 2: Comparison of Reactivity Between Novel Polyethylene Glycol Derivatives In order to prepare a physiologically active polypeptide conjugate using the polyethylene glycol derivatives prepared in Example 1, a conjugate was prepared using a triple agonist peptide, GLP-1/Glucagon/GIP, as a representative physiologically active peptide. The triple agonist peptide consists of 30 amino acids and it corresponds to a peptide including a cysteine residue. Accordingly, the triple agonist peptide was used for the comparison of reactivity of the thiol reactive group of the polyethylene glycol derivatives according to the present invention.

Additionally, linkers #2, #3, #5, #8, #9, and #11 having a molecular weight of about 10K (10,000 Da) were used as polyethylene glycol derivatives. In particular, although linkers #3 and #9 correspond to 10K pALD-PEG-SH (PEG which has a propionaldehyde group and a sulfhydryl group at each end), linker #9 is characterized in that it has an amide structure in front of a thiol reactive group, unlike linker #3. Additionally, linkers #2, #5, #8, and #11 correspond to 10K pALD-PEG-I (PEG which has a propionaldehyde group and an iodine group at each end), linkers #5 and #8 are characterized in that they have an amide structure in front of a thiol reactive group, unlike linkers #2 and #11.

After dissolving peptide powder in 10 mM HCl, for the PEGylation of 10K pALD-PEG-I and 10K pALD-PEG-SH to the cysteine residue of the peptide, the peptide and PEG were reacted at a molar ratio of 1:3 to 1:5 with a reaction concentration of 3 mg/mL at room temperature for about 2 hours. In particular, the reaction was performed in the presence of 50 mM sodium citrate (pH 5.0) or 50 mM HEPES (pH 7.5) and 60% isopropanol (IPA). Upon completion of SDS-PAGE analysis, the reactivity of each thiol reactive group was compared by a band integration method (FIG. 18). Upon confirmation of the reactivity, it was confirmed that the PEG which is characterized by having an having an amide structure in front of the thiol group has superior reactivity to the PEG which does not have an amide structure in front of the thiol group.

Example 3: Preparation of a Conjugate Between a Physiologically Active Polypeptide and an Immunoglobulin Fc Using a Novel Polyethylene Glycol Derivative In order to prepare a conjugate between a physiologically active polypeptide and an immunoglobulin Fc using the polyethylene glycol derivatives prepared in Example 1, a conjugate was prepared using the peptide mentioned in Example 2.

First, linker #7 having a molecular weight of about 10K (10,000 Da) was used as the polyethylene glycol derivative. In particular, linker #7 corresponds to pALD-PEG-OPSS with a molecular weight of about 10K (PEG which has a propionaldehyde group and ortho-pyridyl disulfide group at each end). After dissolving peptide powder in 10 mM HCl, for the PEGylation of 10K pALD-PEG-OPSS to the cysteine residue of the peptide, the peptide and PEG were reacted at a molar ratio of 1:1 to 1:3 with a reaction concentration of 1 mg/mL or 3 mg/mL at room temperature for about 2 hours. In particular, the reaction was performed in the presence of 50 mM sodium citrate (pH 3.0 to pH 5.0) or 50 mM Tris (pH 8.0) and 60% isopropanol.

Additionally, linkers #8, and #9 having a molecular weight of about 10K (10,000 Da) were used as polyethylene glycol derivatives. In particular, linker #8 corresponds to 10K pALD-PEG-IA with a molecular weight of about 10K (PEG which has a propionaldehyde group and iodoacetamide (IA) at each end) and linker #9 corresponds to 10K pALD-PEG-SH with a molecular weight of about 10K (PEG which has a propionaldehyde group and a sulfhydryl group at each end).

For the preparation of a conjugate using the pALD-PEG-IA and pALD-PEG-SH as linkers, the PEGylation reaction was performed in the same condition as in Example 2 and the reaction solution was purified using the SP-HP (GE Healthcare, USA) column which utilized a buffer containing sodium citrate (pH 3.0) and a 45% EtOH and KCl concentration gradient.

Then, after being conjugated to each reactive group, the purified mono-PEGylated peptide and immunoglobulin Fc were reacted at a molar ratio of 1:5 with the total protein concentration of 20 mg/mL at 4° C. for 15 hours. In particular, 20% isopropanol and 20 mM sodium cyanoborohydride, as a reducing agent, were added to 100 mM potassium phosphate buffer as the reaction solution.

Upon completion of the reaction, the reaction solution was applied to a Source 15Q (GE Healthcare, USA) column using a NaCl concentration gradient in a Bis-Tris (pH 6.5) buffer and then applied to a Source ISO (GE Healthcare, USA) column using a concentration gradient of $(NH_4)_2SO_4$ and Tris (pH 7.5) buffer, and thereby the triple agonist-10K PEG-IgFc conjugate was purified. The purity of the thus-prepared conjugate sample was confirmed by SDS-PAGE analysis, and the molecular weight of the conjugate of the triple agonist and PEG was confirmed. Then, the molecular weight of the triple agonist-10K PEG-IgFc conjugate, in which an IgFc was linked to the PEG conjugated to the triple agonist, was confirmed in a non-reducing condition. The experimental results thereof are shown in FIGS. 19 to 21.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

---

SEQUENCE LISTING

```
<160> NUMBER OF SEQ ID NOS: 106

<210> SEQ ID NO 1
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 1

His Xaa Gln Gly Thr Phe Thr Ser Asp Val Ser Ser Tyr Leu Asp Gly
1               5                   10                  15

Gln Ala Ala Lys Glu Phe Ile Ala Trp Leu Val Lys Gly Cys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 2

His Xaa Gln Gly Thr Phe Thr Ser Asp Val Ser Ser Tyr Leu Asp Gly
1               5                   10                  15

Gln Ala Gln Lys Glu Phe Ile Ala Trp Leu Val Lys Gly Cys
            20                  25                  30

<210> SEQ ID NO 3
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 3

His Xaa Gln Gly Thr Phe Thr Ser Asp Val Ser Ser Tyr Leu Leu Gly
```

```
1               5                   10                  15
Gln Ala Ala Lys Gln Phe Ile Ala Trp Leu Val Lys Gly Gly Gly Pro
            20                  25                  30

Ser Ser Gly Ala Pro Pro Ser Cys
            35                  40

<210> SEQ ID NO 4
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 4

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Cys
            20                  25                  30

<210> SEQ ID NO 5
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 5

His Xaa Gln Gly Thr Phe Thr Ser Asp Val Ser Ser Tyr Leu Leu Gly
1               5                   10                  15

Gln Gln Gln Lys Glu Phe Ile Ala Trp Leu Val Lys Gly Gly Gly Pro
            20                  25                  30

Ser Ser Gly Ala Pro Pro Ser Cys
            35                  40

<210> SEQ ID NO 6
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 6

His Xaa Gln Gly Thr Phe Thr Ser Asp Val Ser Ser Tyr Leu Asp Gly
1               5                   10                  15

Gln Ala Ala Lys Glu Phe Val Ala Trp Leu Leu Lys Gly Cys
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Trigonal agonist
<220> FEATURE:
```

```
<221> NAME/KEY: MISC_FEATURE
<222> LOCATION: (2)
<223> OTHER INFORMATION: Xaa is aminoisobutyric acid (Aib)

<400> SEQUENCE: 7

His Xaa Gln Gly Thr Phe Thr Ser Asp Val Ser Lys Tyr Leu Asp Gly
1               5                   10                  15

Gln Ala Ala Lys Glu Phe Val Ala Trp Leu Leu Lys Gly Cys
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 8

His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Lys Gly Cys
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 9

His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Cys
            20                  25                  30

<210> SEQ ID NO 10
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 10

His Xaa Gln Gly Thr Phe Thr Ser Asp Val Ser Lys Tyr Leu Asp Gly
1               5                   10                  15

Gln Ala Ala Gln Glu Phe Val Ala Trp Leu Leu Ala Gly Gly Gly Pro
            20                  25                  30

Ser Ser Gly Ala Pro Pro Pro Ser Cys
            35                  40

<210> SEQ ID NO 11
<211> LENGTH: 41
<212> TYPE: PRT
```

-continued

<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 11

Xaa Gly Glu Gly Thr Phe Thr Ser Asp Leu Ser Lys Tyr Leu Asp Ser
1               5                   10                  15

Arg Arg Gln Gln Leu Phe Val Gln Trp Leu Lys Ala Gly Gly Pro Ser
            20                  25                  30

Ser Gly Ala Pro Pro Pro Ser His Gly
        35                  40

<210> SEQ ID NO 12
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 12

Xaa Gly Glu Gly Thr Phe Ile Ser Asp Leu Ser Lys Tyr Met Asp Glu
1               5                   10                  15

Gln Ala Val Gln Leu Phe Val Glu Trp Leu Met Ala Gly Gly Pro Ser
            20                  25                  30

Ser Gly Ala Pro Pro Pro Ser His Gly
        35                  40

<210> SEQ ID NO 13
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 13

Xaa Gly Glu Gly Thr Phe Ile Ser Asp Tyr Ser Ile Gln Leu Asp Glu
1               5                   10                  15

Ile Ala Val Gln Asp Phe Val Glu Trp Leu Leu Ala Gln Lys Pro Ser
            20                  25                  30

Ser Gly Ala Pro Pro Pro Ser His Gly
        35                  40

<210> SEQ ID NO 14
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 14

```
Xaa Gly Gln Gly Thr Phe Thr Ser Asp Tyr Ser Ile Gln Leu Asp Glu
1               5                   10                  15

Ile Ala Val Arg Asp Phe Val Glu Trp Leu Lys Asn Gly Gly Pro Ser
            20                  25                  30

Ser Gly Ala Pro Pro Pro Ser His Gly
        35                  40
```

<210> SEQ ID NO 15
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 15

```
Xaa Gly Gln Gly Thr Phe Thr Ser Asp Leu Ser Lys Gln Met Asp Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser His Gly
        35                  40
```

<210> SEQ ID NO 16
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 16

```
Xaa Gly Gln Gly Thr Phe Thr Ser Asp Leu Ser Lys Gln Met Asp Ser
1               5                   10                  15

Glu Ala Gln Gln Leu Phe Ile Glu Trp Leu Lys Asn Gly Gly Pro Ser
            20                  25                  30

Ser Gly Ala Pro Pro Pro Ser His Gly
        35                  40
```

<210> SEQ ID NO 17
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 17

```
Xaa Gly Gln Gly Thr Phe Thr Ser Asp Leu Ser Lys Gln Met Asp Glu
1               5                   10                  15

Glu Arg Ala Arg Glu Phe Ile Glu Trp Leu Leu Ala Gln Lys Pro Ser
            20                  25                  30

Ser Gly Ala Pro Pro Pro Ser His Gly
        35                  40
```

```
<210> SEQ ID NO 18
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 18

Xaa Gly Gln Gly Thr Phe Thr Ser Asp Leu Ser Lys Gln Met Asp Ser
1               5                   10                  15

Glu Arg Ala Arg Glu Phe Ile Glu Trp Leu Lys Asn Thr Gly Pro Ser
            20                  25                  30

Ser Gly Ala Pro Pro Pro Ser His Gly
        35                  40

<210> SEQ ID NO 19
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 19

Xaa Gly Gln Gly Thr Phe Thr Ser Asp Leu Ser Ile Gln Tyr Asp Ser
1               5                   10                  15

Glu His Gln Arg Asp Phe Ile Glu Trp Leu Lys Asp Thr Gly Pro Ser
            20                  25                  30

Ser Gly Ala Pro Pro Pro Ser His Gly
        35                  40

<210> SEQ ID NO 20
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)

<400> SEQUENCE: 20

Xaa Gly Gln Gly Thr Phe Thr Ser Asp Leu Ser Ile Gln Tyr Glu Glu
1               5                   10                  15

Glu Ala Gln Gln Asp Phe Val Glu Trp Leu Lys Asp Thr Gly Pro Ser
            20                  25                  30

Ser Gly Ala Pro Pro Pro Ser His Gly
        35                  40

<210> SEQ ID NO 21
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
```

-continued

```
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 21

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
            20                  25                  30

Ser Gly Gln Pro Pro Pro Ser
            35

<210> SEQ ID NO 22
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 22

Tyr Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
            35

<210> SEQ ID NO 23
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 23

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Ala Gln Lys Gly Lys
            20                  25                  30

Lys Asn Asp Trp Lys His Asn Ile Thr
            35                  40

<210> SEQ ID NO 24
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
```

```
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 24

Tyr Xaa Gln Gly Thr Phe Thr Ser Asp Tyr Ser Lys Tyr Leu Asp Glu
1               5                   10                  15

Cys Arg Ala Lys Glu Phe Val Gln Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 25

His Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 26

His Xaa Gln Gly Thr Phe Thr Ser Asp Cys Ser Lys Tyr Leu Asp Ser
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 27
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 27

His Xaa Gln Gly Thr Phe Thr Ser Asp Tyr Ser Lys Tyr Leu Asp Glu
```

```
1               5                   10                  15
Arg Ala Cys Gln Asp Phe Val Gln Trp Leu Leu Asp Gln Gly Gly Pro
            20                  25                  30

Ser Ser Gly Ala Pro Pro Ser
            35                  40

<210> SEQ ID NO 28
<211> LENGTH: 41
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 28

His Xaa Gln Gly Thr Phe Thr Ser Asp Tyr Ser Lys Tyr Leu Asp Glu
1               5                   10                  15

Lys Arg Ala Gln Glu Phe Val Cys Trp Leu Leu Ala Gln Lys Gly Lys
            20                  25                  30

Lys Asn Asp Trp Lys His Asn Ile Thr
            35                  40

<210> SEQ ID NO 29
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 29

His Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asn Thr Cys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 30

His Xaa Gln Gly Thr Phe Thr Ser Asp Tyr Ser Lys Tyr Leu Asp Glu
1               5                   10                  15

Lys Ala Gln Lys Glu Phe Val Gln Trp Leu Leu Asp Thr Cys
            20                  25                  30
```

```
<210> SEQ ID NO 31
<211> LENGTH: 29
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 31

His Xaa Gln Gly Thr Phe Thr Ser Asp Tyr Ser Lys Tyr Leu Asp Glu
1               5                   10                  15

Lys Ala Cys Lys Glu Phe Val Gln Trp Leu Leu Ala Gln
            20                  25

<210> SEQ ID NO 32
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 32

His Xaa Gln Gly Thr Phe Thr Ser Asp Tyr Ser Lys Tyr Leu Asp Glu
1               5                   10                  15

Lys Ala Cys Lys Asp Phe Val Gln Trp Leu Leu Asp Gly Gly Pro Ser
            20                  25                  30

Ser Gly Ala Pro Pro Pro Ser
        35

<210> SEQ ID NO 33
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 33

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30

<210> SEQ ID NO 34
<211> LENGTH: 31
<212> TYPE: PRT
```

```
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 34

His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 35

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
            20                  25                  30

<210> SEQ ID NO 36
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 36

His Xaa Gln Gly Thr Phe Thr Ser Asp Tyr Ser Lys Tyr Leu Cys Glu
1               5                   10                  15

Lys Arg Gln Lys Glu Phe Val Gln Trp Leu Leu Asn Gly Gly Pro Ser
            20                  25                  30

Ser Gly Ala Pro Pro Pro Ser Gly
            35                  40

<210> SEQ ID NO 37
<211> LENGTH: 40
<212> TYPE: PRT
<213> ORGANISM: Artificial Sequence
<220> FEATURE:
<223> OTHER INFORMATION: Trigonal agonist
<220> FEATURE:
```

```
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 37

His Xaa Gln Gly Thr Phe Thr Ser Asp Tyr Ser Lys Tyr Leu Asp Glu
1               5                   10                  15

Cys Arg Gln Lys Glu Phe Val Gln Trp Leu Leu Asn Gly Gly Pro Ser
            20                  25                  30

Ser Gly Ala Pro Pro Pro Ser Gly
        35                  40

<210> SEQ ID NO 38
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 38

Xaa Xaa Gln Gly Thr Phe Thr Ser Asp Lys Ser Ser Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser Ser
        35                  40

<210> SEQ ID NO 39
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 39

His Xaa Gln Gly Thr Phe Thr Ser Asp Tyr Ser Lys Tyr Leu Asp Gly
1               5                   10                  15

Gln His Ala Gln Cys Phe Val Ala Trp Leu Leu Ala Gly Gly Gly Pro
            20                  25                  30

Ser Ser Gly Ala Pro Pro Pro Ser
        35                  40

<210> SEQ ID NO 40
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
```

<223> OTHER INFORMATION: Xaa is aminoisobutyric acid (Aib)

<400> SEQUENCE: 40

His Xaa Gln Gly Thr Phe Thr Ser Asp Lys Ser Lys Tyr Leu Asp Glu
1               5                   10                  15

Arg Ala Cys Gln Asp Phe Val Gln Trp Leu Leu Asp Gly Gly Pro Ser
            20                  25                  30

Ser Gly Ala Pro Pro Pro Ser
        35

<210> SEQ ID NO 41
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 41

His Xaa Gln Gly Thr Phe Thr Ser Asp Lys Ser Lys Tyr Leu Asp Glu
1               5                   10                  15

Cys Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 42
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 42

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser Cys
        35                  40

<210> SEQ ID NO 43
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

```
<400> SEQUENCE: 43

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His His Cys Ser
            20                  25                  30

Ser Gly Gln Pro Pro Pro Ser
        35

<210> SEQ ID NO 44
<211> LENGTH: 39
<212> TYPE: PRT
<213> ORGANISM: Artificial Sequence
<220> FEATURE:
<223> OTHER INFORMATION: Trigonal agonist

<400> SEQUENCE: 44

His Gly Gln Gly Thr Phe Thr Ser Asp Cys Ser Lys Gln Leu Asp Gly
1               5                   10                  15

Gln Ala Ala Gln Glu Phe Val Ala Trp Leu Leu Ala Gly Gly Pro Ser
            20                  25                  30

Ser Gly Ala Pro Pro Pro Ser
        35

<210> SEQ ID NO 45
<211> LENGTH: 39
<212> TYPE: PRT
<213> ORGANISM: Artificial Sequence
<220> FEATURE:
<223> OTHER INFORMATION: Trigonal agonist

<400> SEQUENCE: 45

His Gly Gln Gly Thr Phe Thr Ser Asp Cys Ser Lys Tyr Met Asp Gly
1               5                   10                  15

Gln Ala Ala Gln Asp Phe Val Ala Trp Leu Leu Ala Gly Gly Pro Ser
            20                  25                  30

Ser Gly Ala Pro Pro Pro Ser
        35

<210> SEQ ID NO 46
<211> LENGTH: 39
<212> TYPE: PRT
<213> ORGANISM: Artificial Sequence
<220> FEATURE:
<223> OTHER INFORMATION: Trigonal agonist

<400> SEQUENCE: 46

His Gly Gln Gly Thr Phe Thr Ser Asp Cys Ser Lys Tyr Leu Asp Glu
1               5                   10                  15

Gln His Ala Gln Glu Phe Val Ala Trp Leu Leu Ala Gly Gly Pro Ser
            20                  25                  30

Ser Gly Ala Pro Pro Pro Ser
        35

<210> SEQ ID NO 47
<211> LENGTH: 39
<212> TYPE: PRT
<213> ORGANISM: Artificial Sequence
<220> FEATURE:
<223> OTHER INFORMATION: Trigonal agonist

<400> SEQUENCE: 47

His Gly Gln Gly Thr Phe Thr Ser Asp Cys Ser Lys Tyr Leu Asp Gly
```

```
                 1               5                  10                  15
Gln Arg Ala Gln Glu Phe Val Ala Trp Leu Leu Ala Gly Gly Pro Ser
                20                  25                  30

Ser Gly Ala Pro Pro Ser
            35

<210> SEQ ID NO 48
<211> LENGTH: 39
<212> TYPE: PRT
<213> ORGANISM: Artificial Sequence
<220> FEATURE:
<223> OTHER INFORMATION: Trigonal agonist

<400> SEQUENCE: 48

His Gly Gln Gly Thr Phe Thr Ser Asp Cys Ser Lys Tyr Leu Asp Gly
1               5                  10                  15

Gln Arg Ala Gln Asp Phe Val Asn Trp Leu Leu Ala Gly Gly Pro Ser
                20                  25                  30

Ser Gly Ala Pro Pro Ser
            35

<210> SEQ ID NO 49
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 49

Xaa Xaa Gln Gly Thr Phe Thr Ser Asp Tyr Ser Ile Cys Met Asp Glu
1               5                  10                  15

Ile His Gln Lys Asp Phe Val Asn Trp Leu Leu Asn Thr Lys
                20                  25                  30

<210> SEQ ID NO 50
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 50

His Xaa Gln Gly Thr Phe Thr Ser Asp Tyr Ser Lys Tyr Leu Asp Glu
1               5                  10                  15

Lys Arg Ala Lys Glu Phe Val Gln Trp Leu Leu Asp His His Pro Ser
                20                  25                  30
```

Ser Gly Gln Pro Pro Ser Cys
         35                  40

<210> SEQ ID NO 51
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 51

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 52

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 53

His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 54
<211> LENGTH: 30
<212> TYPE: PRT

```
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 54

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 55

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 56

His Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Cys
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
```

```
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 57

His Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Cys
            20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 58

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Lys Cys
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 59

Xaa Xaa Gln Gly Thr Phe Thr Ser Asp Tyr Ser Ile Cys Met Asp Glu
1               5                   10                  15

Lys His Gln Lys Asp Phe Val Asn Trp Leu Leu Asn Thr Lys
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
```

<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 60

Xaa Xaa Gln Gly Thr Phe Thr Ser Asp Tyr Ser Ile Ala Met Asp Glu
1               5                   10                  15

Lys His Cys Lys Asp Phe Val Asn Trp Leu Leu Asn Thr Lys
            20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 61

Xaa Xaa Gln Gly Thr Phe Thr Ser Asp Tyr Ser Ile Ala Met Asp Glu
1               5                   10                  15

Ile Ala Cys Lys Asp Phe Val Asn Trp Leu Leu Asn Thr Lys
            20                  25                  30

<210> SEQ ID NO 62
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 62

Xaa Xaa Gln Gly Thr Phe Thr Ser Asp Lys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)

<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)

<400> SEQUENCE: 63

Xaa Xaa Gln Gly Thr Phe Thr Ser Asp Cys Ser Lys Tyr Leu Asp Glu
1               5                   10                  15

Arg Ala Ala Gln Asp Phe Val Gln Trp Leu Leu Asp Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 64

Tyr Xaa Gln Gly Thr Phe Thr Ser Asp Tyr Ser Lys Tyr Leu Asp Glu
1               5                   10                  15

Cys Ala Ala Lys Glu Phe Val Gln Trp Leu Leu Asp His His Pro Ser
            20                  25                  30

Ser Gly Gln Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 65

His Xaa Gln Gly Thr Phe Thr Ser Asp Tyr Ser Lys Cys Leu Asp Glu
1               5                   10                  15

Lys Arg Ala Lys Glu Phe Val Gln Trp Leu Leu Asp His His Pro Ser
            20                  25                  30

Ser Gly Gln Pro Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Trigonal agonist
<220> FEATURE:

-continued

```
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 66

Tyr Xaa Gln Gly Thr Phe Thr Ser Asp Tyr Ser Lys Tyr Leu Asp Glu
1               5                   10                  15

Cys Arg Ala Lys Asp Phe Val Gln Trp Leu Leu Asp His His Pro Ser
            20                  25                  30

Ser Gly Gln Pro Pro Pro Ser
            35

<210> SEQ ID NO 67
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 67

Tyr Xaa Gln Gly Thr Phe Thr Ser Asp Tyr Ser Lys Tyr Leu Asp Glu
1               5                   10                  15

Cys Ala Ala Lys Asp Phe Val Gln Trp Leu Leu Asp His His Pro Ser
            20                  25                  30

Ser Gly Gln Pro Pro Pro Ser
            35

<210> SEQ ID NO 68
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 68

Tyr Xaa Gln Gly Thr Phe Thr Ser Asp Tyr Ser Lys Cys Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser
            35

<210> SEQ ID NO 69
<211> LENGTH: 39
<212> TYPE: PRT
<213> ORGANISM: Artificial Sequence
<220> FEATURE:
```

<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 69

Tyr Xaa Gln Gly Thr Phe Thr Ser Asp Tyr Ser Lys Cys Leu Asp Glu
1               5                   10                  15

Arg Ala Ala Lys Glu Phe Val Gln Trp Leu Leu Asp His His Pro Ser
            20                  25                  30

Ser Gly Gln Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 70

Tyr Xaa Gln Gly Thr Phe Thr Ser Asp Tyr Ser Lys Cys Leu Asp Glu
1               5                   10                  15

Lys Arg Ala Lys Asp Phe Val Gln Trp Leu Leu Asp His His Pro Ser
            20                  25                  30

Ser Gly Gln Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 71

Tyr Xaa Gln Gly Thr Phe Thr Ser Asp Tyr Ser Lys Tyr Leu Asp Glu
1               5                   10                  15

Arg Ala Cys Lys Asp Phe Val Gln Trp Leu Leu Asp His His Pro Ser
            20                  25                  30

Ser Gly Gln Pro Pro Ser
        35

<210> SEQ ID NO 72
<211> LENGTH: 39
<212> TYPE: PRT

```
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 72

Tyr Xaa Gln Gly Thr Phe Thr Ser Asp Cys Ser Lys Tyr Leu Asp Glu
1               5                   10                  15

Arg Ala Ala Lys Asp Phe Val Gln Trp Leu Leu Asp His His Pro Ser
                20                  25                  30

Ser Gly Gln Pro Pro Pro Ser
            35

<210> SEQ ID NO 73
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 73

Xaa Xaa Gln Gly Thr Phe Thr Ser Asp Tyr Ser Lys Tyr Leu Asp Glu
1               5                   10                  15

Cys Arg Ala Lys Glu Phe Val Gln Trp Leu Leu Asp His His Pro Ser
                20                  25                  30

Ser Gly Gln Pro Pro Pro Ser
            35

<210> SEQ ID NO 74
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 74

Xaa Xaa Gln Gly Thr Phe Thr Ser Asp Tyr Ser Lys Cys Leu Asp Glu
1               5                   10                  15
```

```
Lys Arg Ala Lys Glu Phe Val Gln Trp Leu Leu Asp His His Pro Ser
            20                  25                  30

Ser Gly Gln Pro Pro Pro Ser
        35
```

<210> SEQ ID NO 75
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 75

```
Tyr Xaa Gln Gly Thr Phe Thr Ser Asp Tyr Ser Lys Tyr Leu Asp Glu
1               5                   10                  15

Lys Ala Ala Lys Glu Phe Val Gln Trp Leu Leu Asp His His Pro Ser
            20                  25                  30

Ser Gly Gln Pro Pro Pro Ser Cys
        35                  40
```

<210> SEQ ID NO 76
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 76

```
Tyr Xaa Gln Gly Thr Phe Thr Ser Asp Tyr Ser Lys Tyr Leu Asp Glu
1               5                   10                  15

Lys Arg Ala Lys Asp Phe Val Gln Trp Leu Leu Asp His His Pro Ser
            20                  25                  30

Ser Gly Gln Pro Pro Pro Ser Cys
        35                  40
```

<210> SEQ ID NO 77
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 77

```
Tyr Xaa Gln Gly Thr Phe Thr Ser Asp Tyr Ser Lys Tyr Leu Asp Glu
```

```
                1               5                  10                 15
Lys Ala Ala Lys Asp Phe Val Gln Trp Leu Leu Asp His His Pro Ser
                20                 25                 30

Ser Gly Gln Pro Pro Pro Ser Cys
            35                  40

<210> SEQ ID NO 78
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 78

His Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 79

His Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30

<210> SEQ ID NO 80
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 80

His Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30
```

<210> SEQ ID NO 81
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 81

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asn Thr Cys
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 82

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Cys
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 83

```
Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 84

Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Cys
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 85

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Cys
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
```

<222> LOCATION: (16)..(20)
<223> OTHER INFORMATION: amino acids at positions 16 and 20 form a ring

<400> SEQUENCE: 86

Xaa Xaa Gln Gly Thr Phe Thr Ser Asp Tyr Ser Lys Tyr Leu Asp Glu
1               5                   10                  15
Lys Arg Gln Lys Glu Phe Val Asn Trp Leu Leu Ala Gln Cys
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 87

Xaa Xaa Gln Gly Thr Phe Thr Ser Asp Tyr Ser Ile Ala Met Asp Glu
1               5                   10                  15
Ile His Gln Lys Asp Phe Val Asn Trp Leu Leu Asn Thr Cys
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 88

Xaa Xaa Gln Gly Thr Phe Thr Ser Asp Tyr Ser Lys Tyr Leu Asp Glu
1               5                   10                  15
Lys Arg Gln Lys Glu Phe Val Gln Trp Leu Leu Asn Thr Lys Cys
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:

```
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 89

Xaa Xaa Gln Gly Thr Phe Thr Ser Asp Tyr Ser Lys Tyr Leu Asp Glu
1               5                   10                  15

Lys Arg Gln Lys Glu Phe Val Gln Trp Leu Leu Asp Thr Lys Cys
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 90

Xaa Xaa Glu Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 91

Xaa Xaa Glu Gly Thr Phe Thr Ser Asp Tyr Ser Ile Ala Met Asp Glu
1               5                   10                  15

Ile His Gln Lys Asp Phe Val Asp Trp Leu Leu Ala Glu Lys Cys
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Trigonal agonist
```

```
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 92

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Ala Gln Lys Cys
                20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 93

Xaa Xaa Gln Gly Thr Phe Thr Ser Asp Tyr Ser Lys Tyr Leu Asp Glu
1               5                   10                  15

Lys Arg Gln Lys Glu Phe Val Asn Trp Leu Leu Ala Gln Lys Cys
                20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (1)
<223> OTHER INFORMATION: Xaa is 4-imidazoacetyl (CA)
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 94

Xaa Xaa Gln Gly Thr Phe Thr Ser Asp Tyr Ser Ile Ala Met Asp Glu
1               5                   10                  15

Ile His Gln Lys Asp Phe Val Asn Trp Leu Leu Asn Thr Lys Cys
                20                  25                  30

<210> SEQ ID NO 95
```

```
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 95

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Cys His His Pro Ser
            20                  25                  30

Ser Gly Gln Pro Pro Pro Ser
        35

<210> SEQ ID NO 96
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 96

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp His Cys Pro Ser
            20                  25                  30

Ser Gly Gln Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 97

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Leu Asp Cys His Pro Ser
            20                  25                  30

Ser Gly Gln Pro Pro Pro Ser
        35
```

```
<210> SEQ ID NO 98
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 98

Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp His His Pro Ser
            20                  25                  30

Ser Gly Gln Pro Pro Pro Ser Cys
        35                  40

<210> SEQ ID NO 99
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 99

Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp His His Pro Ser
            20                  25                  30

Ser Gly Gln Pro Pro Pro Ser Cys
        35                  40

<210> SEQ ID NO 100
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 100

Tyr Xaa Gln Gly Thr Phe Thr Ser Asp Tyr Ser Lys Ala Leu Asp Glu
1               5                   10                  15

Lys Ala Ala Lys Glu Phe Val Gln Trp Leu Leu Asp Gln His Pro Ser
            20                  25                  30

Ser Gly Gln Pro Pro Pro Ser Cys
```

-continued

```
<210> SEQ ID NO 101
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 101

Tyr Xaa Gln Gly Thr Phe Thr Ser Asp Tyr Ser Lys Ala Leu Asp Glu
1               5                   10                  15

Lys Ala Ala Lys Glu Phe Val Asn Trp Leu Leu Asp Gln His Pro Ser
            20                  25                  30

Ser Gly Gln Pro Pro Pro Ser Cys
        35                  40

<210> SEQ ID NO 102
<211> LENGTH: 40
<212> TYPE: PRT
<213> ORGANISM: Artificial Sequence
<220> FEATURE:
<223> OTHER INFORMATION: Trigonal agonist
<220> FEATURE:
<221> NAME/KEY: MISC_FEATURE
<222> LOCATION: (2)
<223> OTHER INFORMATION: Xaa is aminoisobutyric acid (Aib)
<220> FEATURE:
<221> NAME/KEY: MISC_FEATURE
<222> LOCATION: (16)..(20)
<223> OTHER INFORMATION: amino acids at positions 16 and 20 form a ring

<400> SEQUENCE: 102

Tyr Xaa Gln Gly Thr Phe Thr Ser Asp Tyr Ser Lys Ala Leu Asp Glu
1               5                   10                  15

Lys Ala Ala Lys Asp Phe Val Asn Trp Leu Leu Asp Gln His Pro Ser
            20                  25                  30

Ser Gly Gln Pro Pro Pro Ser Cys
        35                  40

<210> SEQ ID NO 103
<211> LENGTH: 30
<212> TYPE: PRT
<213> ORGANISM: Artificial Sequence
<220> FEATURE:
<223> OTHER INFORMATION: General Formula 1
<220> FEATURE:
<221> NAME/KEY: MISC_FEATURE
<222> LOCATION: (1)
<223> OTHER INFORMATION: Xaa is His (H), 4-imidazoacetyl (CA), or Tyr
      (Y)
<220> FEATURE:
<221> NAME/KEY: MISC_FEATURE
<222> LOCATION: (2)
<223> OTHER INFORMATION: Xaa is Gly (G), alpha-methyl-glutamic acid, or
      Aib (aminoisobutyric acid)
<220> FEATURE:
<221> NAME/KEY: MISC_FEATURE
<222> LOCATION: (3)
<223> OTHER INFORMATION: Xaa is Glu (E) or Gln (Q)
<220> FEATURE:
<221> NAME/KEY: MISC_FEATURE
```

-continued

```
<222> LOCATION: (7)
<223> OTHER INFORMATION: Xaa is Thr (T) or Ile (I)
<220> FEATURE:
<221> NAME/KEY: MISC_FEATURE
<222> LOCATION: (10)
<223> OTHER INFORMATION: Xaa is Leu (L), Tyr (Y), Lys (K), Cys (C), or
      Val (V)
<220> FEATURE:
<221> NAME/KEY: MISC_FEATURE
<222> LOCATION: (12)
<223> OTHER INFORMATION: Xaa is Lys (K), Ser (S), or Ile (I)
<220> FEATURE:
<221> NAME/KEY: MISC_FEATURE
<222> LOCATION: (13)
<223> OTHER INFORMATION: Xaa is Gln (Q), Tyr (Y), Ala (A), or Cys (C)
<220> FEATURE:
<221> NAME/KEY: MISC_FEATURE
<222> LOCATION: (14)
<223> OTHER INFORMATION: Xaa is Leu (L), Met (M), or Tyr (Y)
<220> FEATURE:
<221> NAME/KEY: MISC_FEATURE
<222> LOCATION: (15)
<223> OTHER INFORMATION: Xaa is Cys (C), Asp (D), Glu (E), or Leu (L)
<220> FEATURE:
<221> NAME/KEY: MISC_FEATURE
<222> LOCATION: (16)
<223> OTHER INFORMATION: Xaa is Gly (G), Glu (E), or Ser (S)
<220> FEATURE:
<221> NAME/KEY: MISC_FEATURE
<222> LOCATION: (17)
<223> OTHER INFORMATION: Xaa is Gln (Q), Arg (R), Ile (I), Glu (E), Cys
      (C), or Lys (K)
<220> FEATURE:
<221> NAME/KEY: MISC_FEATURE
<222> LOCATION: (18)
<223> OTHER INFORMATION: Xaa is Ala (A), Gln (Q), Arg (R), or His (H)
<220> FEATURE:
<221> NAME/KEY: MISC_FEATURE
<222> LOCATION: (19)
<223> OTHER INFORMATION: Xaa is Ala (A), Gln (Q), Cys (C), or Val (V)
<220> FEATURE:
<221> NAME/KEY: MISC_FEATURE
<222> LOCATION: (20)
<223> OTHER INFORMATION: Xaa is Lys (K), Gln (Q), or Arg (R)
<220> FEATURE:
<221> NAME/KEY: MISC_FEATURE
<222> LOCATION: (21)
<223> OTHER INFORMATION: Xaa is Glu (E), Gln (Q), Leu (L), Cys (C), or
      Asp (D)
<220> FEATURE:
<221> NAME/KEY: MISC_FEATURE
<222> LOCATION: (23)
<223> OTHER INFORMATION: Xaa is Ile (I) or Val (V)
<220> FEATURE:
<221> NAME/KEY: MISC_FEATURE
<222> LOCATION: (24)
<223> OTHER INFORMATION: Xaa is Ala (A), Gln (Q), Cys (C), Asn (N), Asp
      (D), or Glu (E)
<220> FEATURE:
<221> NAME/KEY: MISC_FEATURE
<222> LOCATION: (27)
<223> OTHER INFORMATION: Xaa is Val (V), Leu (L), Lys (K), or Met (M)
<220> FEATURE:
<221> NAME/KEY: MISC_FEATURE
<222> LOCATION: (28)
<223> OTHER INFORMATION: Xaa is Cys (C), Lys (K), Ala (A), Asn (N), or
      Asp (D)
<220> FEATURE:
<221> NAME/KEY: MISC_FEATURE
<222> LOCATION: (29)
<223> OTHER INFORMATION: Xaa is Cys (C), Gly (G), Gln (Q), Thr (T), Glu
      (E), or His (H)
<220> FEATURE:
<221> NAME/KEY: MISC_FEATURE
<222> LOCATION: (30)
<223> OTHER INFORMATION: Xaa is Cys, Gly, Lys or His, or absent; and Xaa
      can be further linked to R1, wherein R1 is Cys, GKKNDWKHNIT,
      m-SSGAPPPS-n, or m-SSGQPPPS-n, or absent; m is -Cys-, -Pro-,
      or -Gly-Pro-; n is -Cys-, -Gly-, -Ser-, or -His-Gly, or absent
```

The invention claimed is:

1. A polyethylene glycol compound of Formula 1 below, a stereoisomer thereof, or a pharmaceutically acceptable salt thereof:

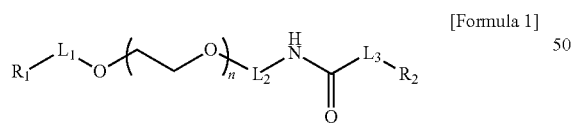

[Formula 1]

wherein, in Formula 1 above,

R₁ is aldehyde;

each of $L_1$ to $L_3$ is independently a linear or branched $C_{1-6}$ alkylene;

$R_2$ is thiol or halogen; and n is an integer of 200 to 2400.

2. The polyethylene glycol compound, stereoisomer thereof, or pharmaceutically acceptable salt of claim 1, wherein $R_2$ is thiol or iodine.

3. The polyethylene glycol compound, stereoisomer thereof, or pharmaceutically acceptable salt of claim 1, wherein the polyethylene glycol compound is selected from the group consisting of the compounds represented by Formula 7, 8, 10, or 11 below:

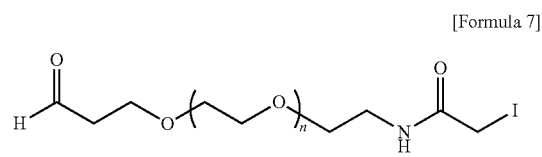

[Formula 7]

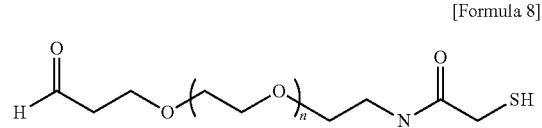

[Formula 8]

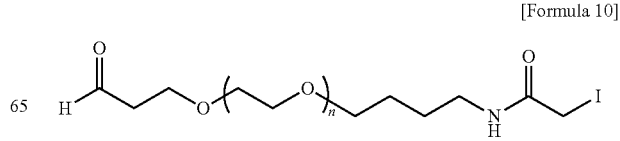

[Formula 10]

[Formula 11]

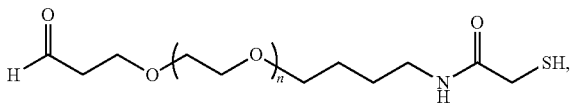

wherein, in Formula 7, 8, 10, or 11, n is an integer of 200 to 2400.

4. A method for preparing a complex comprising a physiologically active polypeptide and a polyethylene glycol compound, in which the polyethylene glycol compound is attached to the physiologically active polypeptide,
said method comprising reacting the polyethylene glycol compound, stereoisomer thereof, or pharmaceutically acceptable salt according to claim 1 with a physiologically active polypeptide to obtain the complex.

5. The method of claim 4, wherein the thiol or halogen as $R_2$ reacts with a thiol group of a cysteine residue of the physiologically active polypeptide.

6. The method of claim 4, further comprising purifying the complex.

7. The method of claim 4, wherein the physiologically active polypeptide is selected from the group consisting of a hormone, a cytokine, an enzyme, an antibody, a growth factor, a transcription factor, a blood factor, a vaccine, an insulinotropic peptide, a neuropeptide, a pituitary hormone, an anti-obesity peptide, an antiviral peptide, a non-native peptide derivative having a physiological activity, a structural protein, a ligand protein, and a receptor.

8. The method of claim 4, wherein the physiologically active polypeptide is selected from the group consisting of glucagon; insulin; somatostatin; peptide YY (PYY); neuropeptide Y (NPY); glucagon-like peptide-1 (GLP-1), glucagon-like peptide-2 (GLP-2); exendin-3; exendin-4; oxyntomodulin; a peptide having an activity on a glucagon receptor, a GLP-1 receptor, and a GIP receptor; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); a growth hormone-releasing peptide; a granulocyte-colony-stimulating factor (GCSF); an interferon (IFN); an interleukin; a prolactin-releasing peptide; orexin; a thyroid-releasing peptide; cholecystokinin; a gastrin inhibitory peptide; calmodulin; a gastric-releasing peptide; motilin; a vasoactive intestinal peptide; an atrial natriuretic peptide (ANP); a B-type natriuretic peptide (BNP); a C-type natriuretic peptide (CNP); neurokinin A; neuromedin; renin; endothelin; sarafotoxin peptide; carsomorphin peptide; dermorphin; dynorphin; endorphin; enkepalin; a T cell factor; tumor necrosis factor; a tumor necrosis factor receptor; a urokinase receptor; a tumor inhibitory factor; a collagenase inhibitor; thymopoietin; thymulin; thymopentin; thymosin; thymic humoral factor; adrenomedullin; allatostatin; an amyloid β-protein fragment; an antibacterial peptide; an antioxidant peptide; bombesin; osteocalcin; a CART (cocaine- and amphetamine-regulated transcript) peptide; E-selectin; ICAM-1 (intercellular adhesion molecule 1); VCAM-1 (vascular cell adhesion molecule 1); leucokine; kringle-5; laminin; inhibin; galanin; fibronectin; pancreastatin; fuzeon; an interferon receptor; a G protein-coupled receptor; an interleukin receptor; an enzyme; an interleukin-binding protein; a cytokine-binding protein; a macrophage-activating factor; a macrophage peptide; B cell factor; protein A; an allergy inhibitor; cell necrosis glycoprotein; immunotoxin; lymphotoxin; a tumor inhibitory factor; a metastasis growth factor; α-1-antitrypsin; albumin; α-lactalbumin; apolipoprotein-E; erythropoietin; highly glycosylated erythropoietin; angiopoietin; hemoglobin; thrombin; a thrombin receptor-activating peptide; thrombomodulin; blood factors VII, VIIa, VIII, IX, and XIII; a plasminogen-activating factor; a fibrin-binding peptide; urokinase; streptokinase; hirudin; protein C; C-reactive protein; a renin inhibitor; superoxide dismutase; a platelet-derived growth factor; an epidermal growth factor; an epithelial cell growth factor; angiostatin; angiotensin; an osteogenic growth factor; an osteogenesis-promoting protein; atriopeptin; a cartilage-inducing factor; elcatonin; a connective tissue-activating factor; a tissue factor pathway inhibitor; luteinizing hormone-releasing hormone; a nerve growth factor; relaxin; somatomedin; insulin-like growth factor; adrenocortical hormone; a pancreatic polypeptide; a gastrin-releasing peptide; corticotropin-releasing factor; thyroid-stimulating hormone; autotoxin; lactoferrin; myostatin; a cell surface antigen; a virus-derived vaccine antigen; monoclonal antibody; polyclonal antibody; an antibody fragment; an erythropoietic growth factor; leukopoietin; amylin; and an analog thereof.

9. A method for preparing a conjugate in which a physiologically active polypeptide and a carrier protein are linked via a polyethylene glycol compound, comprising:
(a) reacting the polyethylene glycol compound, a stereoisomer thereof, or a pharmaceutically acceptable salt thereof according to claim 1 with any one of a physiologically active polypeptide or the carrier protein, thereby preparing a polyethylene glycol compound complex, wherein the physiologically active polypeptide or the carrier protein is attached to one end of the polyethylene glycol compound and the other end of the polyethylene glycol compound has a reactive end group; and
(b) reacting the polyethylene glycol compound complex prepared in step (a) above, wherein the physiologically active polypeptide or the carrier protein is attached to one end of the polyethylene glycol compound and the other end of the polyethylene glycol compound has a reactive end group, with the other one between the physiologically active polypeptide or carrier protein, so as to link the carrier protein or physiologically active polypeptide to the reactive end group of the polyethylene glycol compound complex, thereby preparing the conjugate in which the physiologically active polypeptide and the carrier protein are linked via a polyethylene glycol compound,
wherein the polyethylene glycol compound of step (a) above has a structure of Formula 1 below:

[Formula 1]

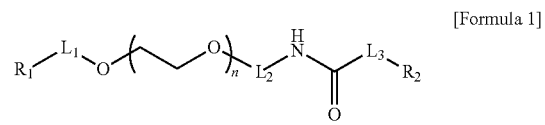

wherein, in Formula 1 above,
$R_1$ is an aldehyde group;
each of $L_1$ to $L_3$ is independently a linear or branched $C_{1-6}$ alkylene;
$R_2$ is thiol or halogen; and
n is an integer of 200 to 2400.

10. The method of claim 9, wherein the physiologically active polypeptide is selected from the group consisting of =a hormone, a cytokine, an enzyme, an antibody, a growth factor, a transcription factor, a blood factor, a vaccine, an insulinotropic peptide, a neuropeptide, a pituitary hormone, an anti-obesity peptide, an antiviral peptide, a non-native peptide derivative having a physiological activity, a structural protein, a ligand protein, and a receptor.

11. The method of claim 9, wherein step (a) is to react $R_2$ of the polyethylene glycol compound having the structure of Formula 1 above with a thiol group located at the cysteine residue of the physiologically active polypeptide.

12. The method of claim 11, wherein step (b) is to react an aldehyde end group of the polyethylene glycol compound with an amine group of the carrier protein.

13. The method of claim 9, further comprising purifying the conjugate, wherein the physiologically active polypeptide and the carrier protein are linked via a polyethylene glycol compound.

14. The method of claim 9, wherein the carrier protein is albumin and a fragment thereof, a polymer of a repeating unit of a particular amino acid sequence, antibody, an antibody fragment, an FcRn-binding material, fibronectin, transferrin, saccharide, or elastin.

15. The method of claim 14, wherein the FcRn-binding material is an immunoglobulin Fc fragment.

16. A method for preparing the polyethylene glycol compound of claim 1, comprising:
 (a) introducing an aldehyde as $R_1$ to one end of a polyethylene glycol; and
 (b) introducing the structure of —NH(CO)$L_3$-$R_2$ to the other end of the polyethylene glycol, wherein $R_2$ is thiol or halogen; and $L_3$ is a linear or branched $C_{1-6}$ alkylene.

17. The polyethylene glycol compound, stereoisomer thereof, or pharmaceutically acceptable salt of claim 1, which is capable of linking a physiologically active polypeptide and a carrier protein.

* * * * *